United States Patent
Kadomatsu et al.

(10) Patent No.: US 9,840,552 B2
(45) Date of Patent: Dec. 12, 2017

(54) MONOCLONAL ANTIBODY AGAINST HUMAN MIDKINE

(71) Applicants: NATIONAL UNIVERSITY CORPORATION NAGOYA UNIVERSITY, Nagoya-shi, Aichi (JP); MEDICAL & BIOLOGICAL LABORATORIES CO., LTD., Nagoya-shi, Aichi (JP)

(72) Inventors: Kenji Kadomatsu, Nagoya (JP); Satoshi Kishida, Nagoya (JP); Kenichiro Ono, Nagoya (JP); Kasumi Yagi, Aichi (JP)

(73) Assignees: NATIONAL UNIVERSITY CORPORATION NAGOYA UNIVERSITY, Nagoya-shi (JP); MEDICAL & BIOLOGICAL LABORATORIES CO., LTD., Nagoya-shi (JP)

( * ) Notice: Subject to any disclaimer, the term of this patent is extended or adjusted under 35 U.S.C. 154(b) by 0 days.

(21) Appl. No.: 14/417,980

(22) PCT Filed: Jul. 30, 2013

(86) PCT No.: PCT/JP2013/070642
§ 371 (c)(1),
(2) Date: Jan. 28, 2015

(87) PCT Pub. No.: WO2014/021339
PCT Pub. Date: Feb. 6, 2014

(65) Prior Publication Data
US 2015/0203573 A1    Jul. 23, 2015

(30) Foreign Application Priority Data
Jul. 30, 2012    (JP) .................. 2012-168637

(51) Int. Cl.
*C07K 16/22*    (2006.01)
*A61K 39/395*   (2006.01)

(52) U.S. Cl.
CPC .......... *C07K 16/22* (2013.01); *C07K 2317/24* (2013.01); *C07K 2317/34* (2013.01); *C07K 2317/55* (2013.01); *C07K 2317/565* (2013.01); *C07K 2317/73* (2013.01); *C07K 2317/76* (2013.01); *C07K 2317/90* (2013.01)

(58) Field of Classification Search
None
See application file for complete search history.

(56) References Cited

U.S. PATENT DOCUMENTS

| | | |
|---|---|---|
| 2003/0072739 A1 | 4/2003 | Takada et al. |
| 2004/0077579 A1 | 4/2004 | Kadomatsu et al. |
| 2006/0148738 A1 | 7/2006 | Muramatsu et al. |
| 2010/0092488 A1 | 4/2010 | Suzumura et al. |
| 2010/0311187 A1 | 12/2010 | Matsui et al. |
| 2011/0086906 A1 | 4/2011 | Suzumura et al. |

FOREIGN PATENT DOCUMENTS

| | | |
|---|---|---|
| EP | 2088159 A1 | 8/2009 |
| JP | 200285058 A | 3/2002 |
| JP | 2007137771 A | 6/2007 |
| JP | 2007297282 A | 11/2007 |
| WO | 9903493 A1 | 1/1999 |
| WO | 0010608 A1 | 3/2000 |
| WO | 2004078210 A1 | 9/2004 |
| WO | 2004085642 A1 | 10/2004 |
| WO | 2007055378 A1 | 5/2007 |
| WO | 2008059616 A1 | 5/2008 |
| WO | 2010074218 A1 | 7/2010 |

OTHER PUBLICATIONS

Muramatsu et al., Current Pharmaceutical Design, 17:410-423, Feb. 2011.*
Maehara H. et al., "Midkine as a novel target for antibody therapy in osteosarcoma", Biochem. Biophys. Res. Commun., 2007, 358(3), pp. 757-762.
Cernkovich E. et al., "Midkine is an autocrine activator of signal transducer and activator of transcription 3 in 3T3-L1 cells", Endocrinology, 2007, 148(4), pp. 1598-1604.
Vilar J et al., "Midkine is involved in kidney development and in its regulation by Retinoids", J. Am. Soc. Nephrol., 2002, 13(3), pp. 668-676.
Sueyoshi T. et al., "Therapeutic approaches targeting midkine suppress tumor growth and lung metastasis in osteosarcoma", Cancer Lett., 2012, 316(1), pp. 23-30 (Epub Oct. 20, 2011).
Iwasaki W. et al., "Solution structure of midkine, a new heparin-binding growth factor", EMBO J., 1997, 16(23), pp. 6936-6946.
Asai T et al., "Identification of heparin-binding sites in midkine and their role in neurite-promotion", Biochem. Biophys. Res. Commun., 1997, 236(1), pp. 66-70.
Foote J et al., "Antibody framework residues affecting the conformation of the hypervariable Loops", J. Mol. Biol., 1992, 224(2), pp. 487-499.
Kadomatsu K. et al., "cDNA Cloning and Sequencing of a New Gene Intensely Expressed in Early Differentiation Stages of Embryonal Carcinoma Cells and in Mid-Gestation Period of Mouse Embryogenesis", (1988) Biochem . Biophys .Res . Commun., 151. 1312-1318 [PMID: 3355557].
Tomomura M. et al., "A Retinoic Acid-responsive Gene, MK, Found in the Teratocarcinoma System", (1990) J. Biol. Chem, 265 , 10765-10770. [PMID: 2355021].

(Continued)

*Primary Examiner* — Marianne P Allen
(74) *Attorney, Agent, or Firm* — Sughrue Mion, PLLC

(57) ABSTRACT

A monoclonal antibody, which recognizes at least two amino acids among amino acids located at position 69, position 79, position 81 and position 102 of human midkine, has been found to have excellent reactivity with and excellent neutralizing activity against human midkine. Moreover, the activity of suppressing the proliferation of tumor has been observed in the antibody having excellent neutralizing activity. The use of the antibody of the present invention makes it possible to treat cancer effectively and to detect or purify midkine efficiently.

6 Claims, 21 Drawing Sheets

(56) References Cited

OTHER PUBLICATIONS

Tsutsui J et al., "A new Family of Heparin Growth/ Differentiation Factors: Increased Midkine Expression in Wilms' Tumor and Other Human Carcinomas", (1993) Cancer Res. 53, 1281-1285. [PMID:8383007].
Michikawa M et al., "Retinoic Acid Responsive Gene Product, Midkine, Has Neurotrophic Functions for Mouse Spinal Cord and Dorsal Root Ganglion Neurons in Culture", (1993) J. Neurosci. Res., 35, 530-539. [PMID:8377224].
Kadomatsu K. et al., "A Retinoic Acid Responsive Gene MK Found in the Teratocarcinoma System is Expressed in Spatially and Temporally Controlled Manner during Mouse Embryogenesis", (1990) J. Cell Biol. 110, 607-616. [PMID:1689730].
Garver R. I. et al., "Reciprocal Expression of Pleiotrophin and Midkine in Normal Versus Malignant Lung Tissues", (1993) Am. J. Respir. Cell Mol. Biol. 9, 463-466. [PMID:8217186].
Aridome K. et al., "Increased Midkine Gene Expression in Human Gastrointestinal Cancers", (1995) Jap. J. Cancer Res. 86, 655-661. [PMID:7559083].
O'Brien T. et al., "The Angiogenic Factor Midkine is Expressed in Bladder Cancer, and Overexpression Correlates with a Poor Outcome in Patients with Invasive Cancers", (1996) Cancer Res. 56, 2515-2518. [PMID: 8653688].
Muramatsu T., "Midkine and Pleiotrophin: Two Related Proteins Involved in Development, Survival, Inflammation and Tumorigenesis", (2002) J Biochem 132 (3) 359-371.
Kohl NE et al., "Transposition and Amplification of Oncogene-Related Sequences in Human Neuroblastomas", (1983) Cell 35, 359-367.

Brodeur GM et al., "Amplification of N-myc in Untreated Human Neuroblastomas Correlates with Advanced Disease Stage", (1984) Science (New York, NY) 224, 1121-1124.
Seeger RC et al., "Association of Multiple Copies of the N-myc Oncogene With Rapid Progression of Neuroblastomas",(1985) The New England journal of medicine 313. 1111-1116.
Ikematsu S. et al., "Correlation of elevated level of blood midkine with poor prognostic factors of human neuroblastomas", (2003) Br. J. Cancer 88, 1522-1526. [PMID: 12771916].
Ikematsu S et al., "Plasma midkine level is a prognostic factor for human neuroblastoma", (Oct. 2008) Cancer Science 99 (10), 2070-2074.
Muramatsu H. et al., "Midkine, A Retinoic Acid-inducible Growth/ Differentiation Factor: Immunochemical Evidence for the Function and Distribution", (1993) Dev. Biol. 159. 392-402. [PMID:8405666].
Kaneda N. et al., "Midkine, a Heparin-Binding Growth/Differentiation Factor, Exhibits Nerve Cell Adhesion and Guidance Activity for Neurite Outgrowth In Vitro", (1996) J Biochem 119 (6)1150-1156.
Yoshida Y. et al., "Midkine is present in the early stage of cerebral infarct",(1995) Dev. Brain Res. 85, 25-30. [PMID:7781164].
Horiba M. et al., "Midkine Plays a Protective Role Against Cardiac Ischemia/Reperfusion Injury Through a Reduction of Apoptotic Reaction", (2006) Circulation. 114, 1713-1720. [PMID:17015789].
Iwasaki W. et al., "Solution structure of midkine, a new heparin-binding growth factor", (1997) EMBO J. 16, 6936-6946. [PMID: 9384573].
Kojima S. et al., "Synthetic Peptides Derived From Midkine Enhance Plasminogen Activator Activity in Bovine Aortic Endothelial Cells", (1995) Biochem. Biophys. Res Commun. 206, 468-473.

* cited by examiner

```
                        SEQUENCE LISTING

<160> NUMBER OF SEQ IDS: 145

<210> SEQ ID NO 1
<211> LENGTH: 11
<212> TYPE: PRT
<213> ORGANISM: Mus musculus
<220> FEATURE:
<221> NAME/KEY: misc_feature
<222> LOCATION: (1)..(11)
<223> OTHER INFORMATION: CDR1 of Light Chain(FB54)

<400> SEQUENCE: 1

Ile Thr Ser Thr Asp Ile Asp Asp Glu Met Asn
1               5                   10

<210> SEQ ID NO 2
<211> LENGTH: 7
<212> TYPE: PRT
<213> ORGANISM: Mus musculus
<220> FEATURE:
<221> NAME/KEY: misc_feature
<222> LOCATION: (1)..(7)
<223> OTHER INFORMATION: CDR2 of Light Chain(FB54)

<400> SEQUENCE: 2

Glu Gly Asn Thr Leu Arg Pro
1               5

<210> SEQ ID NO 3
<211> LENGTH: 9
<212> TYPE: PRT
<213> ORGANISM: Mus musculus
<220> FEATURE:
<221> NAME/KEY: misc_feature
<222> LOCATION: (1)..(9)
<223> OTHER INFORMATION: CDR3 of Light Chain(FB54)

<400> SEQUENCE: 3

Leu Gln Ser Asp Asn Leu Pro Tyr Thr
1               5

<210> SEQ ID NO 4
<211> LENGTH: 5
<212> TYPE: PRT
<213> ORGANISM: Mus musculus
<220> FEATURE:
<221> NAME/KEY: misc_feature
<222> LOCATION: (1)..(5)
<223> OTHER INFORMATION: CDR1 of Heavy Chain(FB54)

<400> SEQUENCE: 4

Ser Tyr Ala Met Ser
1               5

<210> SEQ ID NO 5
<211> LENGTH: 17
<212> TYPE: PRT
<213> ORGANISM: Mus musculus
<220> FEATURE:
<221> NAME/KEY: misc_feature
```

<222> LOCATION: (1)..(17)
<223> OTHER INFORMATION: CDR2 of Heavy Chain(FB54)

<400> SEQUENCE: 5

Thr Ile Ser Ser Gly Gly Ser Tyr Thr Tyr Tyr Pro Asp Ser Val Lys
1               5                   10                  15

Gly

<210> SEQ ID NO 6
<211> LENGTH: 14
<212> TYPE: PRT
<213> ORGANISM: Mus musculus
<220> FEATURE:
<221> NAME/KEY: misc_feature
<222> LOCATION: (1)..(14)
<223> OTHER INFORMATION: CDR3 of Heavy Chain(FB54)

<400> SEQUENCE: 6

His Asn Tyr Arg Tyr Asp Glu Tyr Tyr Tyr Ala Met Asp Tyr
1               5                   10

<210> SEQ ID NO 7
<211> LENGTH: 107
<212> TYPE: PRT
<213> ORGANISM: Mus musculus
<220> FEATURE:
<221> NAME/KEY: misc_feature
<222> LOCATION: (1)..(107)
<223> OTHER INFORMATION: Variable Region of Light Chain(FB54)

<400> SEQUENCE: 7

Glu Thr Thr Val Thr Gln Ser Pro Thr Ser Leu Ser Met Ala Ile Gly
1               5                   10                  15

Glu Lys Val Thr Ile Arg Cys Ile Thr Ser Thr Asp Ile Asp Asp Glu
            20                  25                  30

Met Asn Trp Tyr Gln Gln Lys Pro Gly Glu Pro Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Tyr
                85                  90                  95

Thr Phe Gly Gly Gly Thr Lys Leu Glu Ile Lys
            100                 105

<210> SEQ ID NO 8
<211> LENGTH: 123
<212> TYPE: PRT
<213> ORGANISM: Mus musculus
<220> FEATURE:
<221> NAME/KEY: misc_feature
<222> LOCATION: (1)..(123)
<223> OTHER INFORMATION: Variable Region of Heavy Chain(FB54)

<400> SEQUENCE: 8

Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
            20                  25                  30

Ala Met Ser Trp Val Arg Gln Thr Pro Glu Lys Arg Leu Glu Trp Val
        35                  40                  45

```
Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Phe Cys
                85                  90                  95

Ala Arg His Asn Tyr Arg Tyr Asp Glu Tyr Tyr Tyr Ala Met Asp Tyr
                    100                 105                 110

Trp Gly Gln Gly Thr Ser Val Thr Val Ser Ser
            115                 120
```

<210> SEQ ID NO 9
<211> LENGTH: 107
<212> TYPE: PRT
<213> ORGANISM: Artificial Sequence
<220> FEATURE:
<223> OTHER INFORMATION: Artificially Humanized Variable Region of Light
      Chain
<220> FEATURE:
<221> NAME/KEY: misc_feature
<222> LOCATION: (1)..(107)
<223> OTHER INFORMATION: Variable Region of Light Chain(FB54-rKa)

<400> SEQUENCE: 9

```
Asp Ile Gln Met Thr Gln Ser Pro Ser Ser Leu Ser Ala Ser Val Gly
1               5                   10                  15

Asp Arg Val Thr Ile Thr Cys Ile Thr Ser Thr Asp Ile Asp Asp Glu
                20                  25                  30

Met Asn Trp Tyr Gln Gln Lys Pro Gly Lys Gly Pro Lys Leu Leu Ile
            35                  40                  45

Ser Glu Gly Asn Thr Leu Arg Pro Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Ser Asp Asn Leu Pro Tyr
                85                  90                  95

Thr Phe Gly Gln Gly Thr Lys Leu Glu Ile Lys
            100                 105
```

<210> SEQ ID NO 10
<211> LENGTH: 107
<212> TYPE: PRT
<213> ORGANISM: Artificial Sequence
<220> FEATURE:
<223> OTHER INFORMATION: Artificially Humanized Variable Region of Light
      Chain
<220> FEATURE:
<221> NAME/KEY: misc_feature
<222> LOCATION: (1)..(107)
<223> OTHER INFORMATION: Variable Region of Light Chain(FB54-rKb)

<400> SEQUENCE: 10

```
Asp Thr Gln Val Thr Gln Ser Pro Ser Ser Leu Ser Ala Ser Val Gly
1               5                   10                  15

Asp Arg Val Thr Ile Thr Cys Ile Thr Ser Thr Asp Ile Asp Asp Glu
                20                  25                  30

Met Asn Trp Tyr Gln Gln Lys Pro Gly Lys Gly Pro Lys Leu Leu Ile
            35                  40                  45

Ser Glu Gly Asn Thr Leu Arg Pro Gly Val Pro Ser Arg Phe Ser Ser
    50                  55                  60

Ser Gly Ser Gly Thr Asp Phe Thr Leu Thr Ile Ser Ser Leu Gln Pro
```

```
                65                  70                  75                  80
Glu Asp Phe Ala Thr Tyr Tyr Cys Leu Gln Ser Asp Asn Leu Pro Tyr
                    85                  90                  95

Thr Phe Gly Gln Gly Thr Lys Leu Glu Ile Lys
                100                 105

<210> SEQ ID NO 11
<211> LENGTH: 107
<212> TYPE: PRT
<213> ORGANISM: Artificial Sequence
<220> FEATURE:
<223> OTHER INFORMATION: Artificially Humanized Variable Region of Light
      Chain
<220> FEATURE:
<221> NAME/KEY: misc_feature
<222> LOCATION: (1)..(107)
<223> OTHER INFORMATION: Variable Region of Light Chain(FB54-rKc)

<400> SEQUENCE: 11

Glu Thr Thr Val Thr Gln Ser Pro Ser Ser Leu Ser Ala Ser Val Gly
1               5                   10                  15

Asp Arg Val Thr Ile Arg Cys Ile Thr Ser Thr Asp Ile Asp Asp Glu
                20                  25                  30

Met Asn Trp Tyr Gln Gln Lys Pro Gly Lys Gly Pro Lys Leu Leu Ile
            35                  40                  45

Ser Glu Gly Asn Thr Leu Arg Pro Gly Val Pro Ser Arg Phe Ser Ser
        50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Leu Gln Ser Asp Asn Leu Pro Tyr
                    85                  90                  95

Thr Phe Gly Gln Gly Thr Lys Leu Glu Ile Lys
                100                 105

<210> SEQ ID NO 12
<211> LENGTH: 123
<212> TYPE: PRT
<213> ORGANISM: Artificial Sequence
<220> FEATURE:
<223> OTHER INFORMATION: Artificially Humanized Variable Region of Heavy
      Chain
<220> FEATURE:
<221> NAME/KEY: misc_feature
<222> LOCATION: (1)..(123)
<223> OTHER INFORMATION: Variable Region of Heavy Chain(FB54-rHa)

<400> SEQUENCE: 12

Glu Val Gln Leu Val Glu Ser Gly Gly Gly Leu Val Lys Pro Gly Gly
1               5                   10                  15

Tyr Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Asp Trp Val
            35                  40                  45

Ala Thr Ile Ser Ser Gly Gly Ser Tyr Thr Tyr Tyr Pro Asp Ser Val
        50                  55                  60

Lys Gly Arg Phe Thr Ile Ser Arg Asp Asn Ala Lys Asn Ser Leu Tyr
65                  70                  75                  80

Leu Gln Met Asn Ser Leu Thr Asp Asp Thr Ala Val Tyr Phe Cys
                    85                  90                  95

Ala Arg His Asn Tyr Arg Tyr Asp Glu Tyr Tyr Tyr Ala Met Asp Tyr
                100                 105                 110
```

Trp Gly Gln Gly Thr Leu Val Thr Val Ser Ser
        115                 120

<210> SEQ ID NO 13
<211> LENGTH: 11
<212> TYPE: PRT
<213> ORGANISM: Artificial Sequence
<220> FEATURE:
<223> OTHER INFORMATION: CDR1 of Artificially Mutated Variable Region of
      Light Chain
<220> FEATURE:
<221> NAME/KEY: misc_feature
<222> LOCATION: (1)..(11)
<223> OTHER INFORMATION: CDR1 of Light Chain(matu002)

<400> SEQUENCE: 13

Thr Thr Ser Ile Asp Ile Asp Asp Glu Met Asn
1               5                   10

<210> SEQ ID NO 14
<211> LENGTH: 7
<212> TYPE: PRT
<213> ORGANISM: Mus musculus
<220> FEATURE:
<221> NAME/KEY: misc_feature
<222> LOCATION: (1)..(7)
<223> OTHER INFORMATION: CDR2 of Light Chain(matu002)

<400> SEQUENCE: 14

Glu Gly Asn Thr Leu Arg Pro
1               5

<210> SEQ ID NO 15
<211> LENGTH: 9
<212> TYPE: PRT
<213> ORGANISM: Mus musculus
<220> FEATURE:
<221> NAME/KEY: misc_feature
<222> LOCATION: (1)..(9)
<223> OTHER INFORMATION: CDR3 of Light Chain(matu002)

<400> SEQUENCE: 15

Leu Gln Ser Asp Asn Leu Pro Tyr Thr
1               5

<210> SEQ ID NO 16
<211> LENGTH: 5
<212> TYPE: PRT
<213> ORGANISM: Mus musculus
<220> FEATURE:
<221> NAME/KEY: misc_feature
<222> LOCATION: (1)..(5)
<223> OTHER INFORMATION: CDR1 of Heavy Chain(matu002)

<400> SEQUENCE: 16

Ser Tyr Ala Met Ser
1               5

<210> SEQ ID NO 17
<211> LENGTH: 17
<212> TYPE: PRT
<213> ORGANISM: Mus musculus
<220> FEATURE:
<221> NAME/KEY: misc_feature
<222> LOCATION: (1)..(17)
<223> OTHER INFORMATION: CDR2 of Heavy Chain(matu002)

<400> SEQUENCE: 17

```
Thr Ile Ser Ser Gly Gly Ser Tyr Thr Tyr Tyr Pro Asp Ser Val Lys
1               5                   10                  15

Gly
```

<210> SEQ ID NO 18
<211> LENGTH: 14
<212> TYPE: PRT
<213> ORGANISM: Mus musculus
<220> FEATURE:
<221> NAME/KEY: misc_feature
<222> LOCATION: (1)..(14)
<223> OTHER INFORMATION: CDR3 of Heavy Chain(matu002)

<400> SEQUENCE: 18

```
His Asn Tyr Arg Tyr Asp Glu Tyr Tyr Tyr Ala Met Asp Tyr
1               5                   10
```

<210> SEQ ID NO 19
<211> LENGTH: 107
<212> TYPE: PRT
<213> ORGANISM: Artificial Sequence
<220> FEATURE:
<223> OTHER INFORMATION: Artificially Mutated Variable Region of Light
      Chain
<220> FEATURE:
<221> NAME/KEY: misc_feature
<222> LOCATION: (1)..(107)
<223> OTHER INFORMATION: Variable Region of Light Chain(matu002)

<400> SEQUENCE: 19

```
Glu Thr Thr Val Thr Gln Ser Pro Thr Ser Leu Ser Met Ala Ile Gly
1               5                   10                  15

Glu Lys Val Thr Ile Arg Cys Thr Thr Ser Ile Asp Ile Asp Asp Glu
                20                  25                  30

Met Asn Trp Tyr Gln Gln Met Pro Gly Glu Pro Pro Lys Leu Leu Ile
            35                  40                  45

Ser Glu Gly Asn Thr Leu Arg Pro Gly Val Pro Ser Arg Phe Ser Ser
50                  55                  60

Ser Gly Tyr Gly Thr Asp Phe Val Phe Thr Ile Glu Asn Met Leu Ser
65                  70                  75                  80

Glu Asp Val Ala Asp Tyr Tyr Cys Leu Gln Ser Asp Asn Leu Pro Tyr
                85                  90                  95

Thr Phe Gly Gly Gly Thr Lys Leu Glu Ile Lys
            100                 105
```

<210> SEQ ID NO 20
<211> LENGTH: 123
<212> TYPE: PRT
<213> ORGANISM: Mus musculus
<220> FEATURE:
<221> NAME/KEY: misc_feature
<222> LOCATION: (1)..(123)
<223> OTHER INFORMATION: Variable Region of Heavy Chain(matu002)

<400> SEQUENCE: 20

```
Glu Val Met Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Tyr
                20                  25                  30

Ala Met Ser Trp Val Arg Gln Thr Pro Glu Lys Arg Leu Glu Trp Val
            35                  40                  45

Ala Thr Ile Ser Ser Gly Gly Ser Tyr Thr Tyr Tyr Pro Asp Ser Val
50                  55                  60
```

-continued

```
Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Phe Cys
                85                  90                  95

Ala Arg His Asn Tyr Arg Tyr Asp Glu Tyr Tyr Tyr Ala Met Asp Tyr
            100                 105                 110

Trp Gly Gln Gly Thr Ser Val Thr Val Ser Ser
        115                 120

<210> SEQ ID NO 21
<211> LENGTH: 11
<212> TYPE: PRT
<213> ORGANISM: Artificial Sequence
<220> FEATURE:
<223> OTHER INFORMATION: CDR1 of Artificially Mutated Variable Region of
      Light Chain
<220> FEATURE:
<221> NAME/KEY: misc_feature
<222> LOCATION: (1)..(11)
<223> OTHER INFORMATION: CDR1 of Light Chain(matu089)

<400> SEQUENCE: 21

Ile Thr Ser Ile Asp Ile Asp Asp Glu Met Asn
1               5                   10

<210> SEQ ID NO 22
<211> LENGTH: 7
<212> TYPE: PRT
<213> ORGANISM: Mus musculus
<220> FEATURE:
<221> NAME/KEY: misc_feature
<222> LOCATION: (1)..(7)
<223> OTHER INFORMATION: CDR2 of Light Chain(matu089)

<400> SEQUENCE: 22

Glu Gly Asn Thr Leu Arg Pro
1               5

<210> SEQ ID NO 23
<211> LENGTH: 9
<212> TYPE: PRT
<213> ORGANISM: Mus musculus
<220> FEATURE:
<221> NAME/KEY: misc_feature
<222> LOCATION: (1)..(9)
<223> OTHER INFORMATION: CDR3 of Light Chain(matu089)

<400> SEQUENCE: 23

Leu Gln Ser Asp Asn Leu Pro Tyr Thr
1               5

<210> SEQ ID NO 24
<211> LENGTH: 5
<212> TYPE: PRT
<213> ORGANISM: Mus musculus
<220> FEATURE:
<221> NAME/KEY: misc_feature
<222> LOCATION: (1)..(5)
<223> OTHER INFORMATION: CDR1 of Heavy Chain(matu089)

<400> SEQUENCE: 24

Ser Tyr Ala Met Ser
1               5

<210> SEQ ID NO 25
<211> LENGTH: 17
```

```
<212> TYPE: PRT
<213> ORGANISM: Mus musculus
<220> FEATURE:
<221> NAME/KEY: misc_feature
<222> LOCATION: (1)..(17)
<223> OTHER INFORMATION: CDR2 of Heavy Chain(matu089)

<400> SEQUENCE: 25

Thr Ile Ser Ser Gly Gly Ser Tyr Thr Tyr Tyr Pro Asp Ser Val Lys
1               5                   10                  15
Gly

<210> SEQ ID NO 26
<211> LENGTH: 14
<212> TYPE: PRT
<213> ORGANISM: Mus musculus
<220> FEATURE:
<221> NAME/KEY: misc_feature
<222> LOCATION: (1)..(14)
<223> OTHER INFORMATION: CDR3 of Heavy Chain(matu089)

<400> SEQUENCE: 26

His Asn Tyr Arg Tyr Asp Glu Tyr Tyr Tyr Ala Met Asp Tyr
1               5                   10

<210> SEQ ID NO 27
<211> LENGTH: 107
<212> TYPE: PRT
<213> ORGANISM: Artificial Sequence
<220> FEATURE:
<223> OTHER INFORMATION: Artificially Mutated Variable Region of Light
      Chain
<220> FEATURE:
<221> NAME/KEY: misc_feature
<222> LOCATION: (1)..(107)
<223> OTHER INFORMATION: Variable Region of Light Chain(matu089)

<400> SEQUENCE: 27

Glu Thr Thr Val Thr Gln Ser Pro Thr Ser Leu Ser Met Ala Ile Gly
1               5                   10                  15

Glu Lys Val Thr Ile Arg Cys Ile Thr Ser Ile Asp Ile Asp Asp Glu
                20                  25                  30

Met Asn Trp Tyr Gln Gln Lys Pro Gly Glu Pro Pro Lys Leu Leu Ile
            35                  40                  45

Ser Glu Gly Asn Thr Leu Arg Pro Gly Val Pro Ser Arg Phe Ser Ser
        50                  55                  60

Ser Gly Tyr Gly Thr Asp Phe Val Phe Thr Ile Glu Asn Val Leu Ser
65                  70                  75                  80

Glu Asp Val Ala Asp Tyr Tyr Cys Leu Gln Ser Asp Asn Leu Pro Tyr
                85                  90                  95

Thr Phe Gly Gly Gly Thr Lys Leu Glu Ile Lys
            100                 105

<210> SEQ ID NO 28
<211> LENGTH: 123
<212> TYPE: PRT
<213> ORGANISM: Artificial Sequence
<220> FEATURE:
<223> OTHER INFORMATION: Artificially Mutated Variable Region of Heavy
      Chain
<220> FEATURE:
<221> NAME/KEY: misc_feature
<222> LOCATION: (1)..(123)
<223> OTHER INFORMATION: Variable Region of Heavy Chain(matu089)

<400> SEQUENCE: 28
```

```
Glu Val Met Leu Val Glu Ser Gly Gly Gly Leu Val Glu Pro Gly Gly
1               5                   10                  15

Ser Leu Lys Leu Ser Cys Thr Val Ser Gly Phe Thr Phe Ser Ser Tyr
                20                  25                  30

Ala Met Ser Trp Val Arg Gln Thr Pro Glu Lys Arg Leu Glu Trp Val
            35                  40                  45

Ala Thr Ile Ser Ser Gly Gly Ser Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Phe Cys
                85                  90                  95

Ala Arg His Asn Tyr Arg Tyr Asp Glu Tyr Tyr Tyr Ala Met Asp Tyr
            100                 105                 110

Trp Gly His Gly Thr Ser Val Thr Val Ser Ser
            115                 120

<210> SEQ ID NO 29
<211> LENGTH: 11
<212> TYPE: PRT
<213> ORGANISM: Artificial Sequence
<220> FEATURE:
<223> OTHER INFORMATION: CDR1 of Artificially Mutated Variable Region of
      Light Chain
<220> FEATURE:
<221> NAME/KEY: misc_feature
<222> LOCATION: (1)..(11)
<223> OTHER INFORMATION: CDR1 of Light Chain(matu014)

<400> SEQUENCE: 29

Ile Thr Asn Ile Asp Ile Asp Asp Glu Met Asn
1               5                   10

<210> SEQ ID NO 30
<211> LENGTH: 7
<212> TYPE: PRT
<213> ORGANISM: Mus musculus
<220> FEATURE:
<221> NAME/KEY: misc_feature
<222> LOCATION: (1)..(7)
<223> OTHER INFORMATION: CDR2 of Light Chain(matu014)

<400> SEQUENCE: 30

Glu Gly Asn Thr Leu Arg Pro
1               5

<210> SEQ ID NO 31
<211> LENGTH: 9
<212> TYPE: PRT
<213> ORGANISM: Mus musculus
<220> FEATURE:
<221> NAME/KEY: misc_feature
<222> LOCATION: (1)..(9)
<223> OTHER INFORMATION: CDR3 of Light Chain(matu014)

<400> SEQUENCE: 31

Leu Gln Ser Asp Asn Leu Pro Tyr Thr
1               5

<210> SEQ ID NO 32
<211> LENGTH: 5
<212> TYPE: PRT
<213> ORGANISM: Mus musculus
<220> FEATURE:
```

```
<221> NAME/KEY: misc_feature
<222> LOCATION: (1)..(5)
<223> OTHER INFORMATION: CDR1 of Heavy Chain(matu014)

<400> SEQUENCE: 32

Ser Tyr Ala Met Ser
1               5

<210> SEQ ID NO 33
<211> LENGTH: 17
<212> TYPE: PRT
<213> ORGANISM: Mus musculus
<220> FEATURE:
<221> NAME/KEY: misc_feature
<222> LOCATION: (1)..(17)
<223> OTHER INFORMATION: CDR2 of Heavy Chain(matu014)

<400> SEQUENCE: 33

Thr Ile Ser Ser Gly Gly Ser Tyr Thr Tyr Tyr Pro Asp Ser Val Lys
1               5                   10                  15

Gly

<210> SEQ ID NO 34
<211> LENGTH: 14
<212> TYPE: PRT
<213> ORGANISM: Mus musculus
<220> FEATURE:
<221> NAME/KEY: misc_feature
<222> LOCATION: (1)..(14)
<223> OTHER INFORMATION: CDR3 of Heavy Chain(matu014)

<400> SEQUENCE: 34

His Asn Tyr Arg Tyr Asp Glu Tyr Tyr Tyr Ala Met Asp Tyr
1               5                   10

<210> SEQ ID NO 35
<211> LENGTH: 107
<212> TYPE: PRT
<213> ORGANISM: Artificial Sequence
<220> FEATURE:
<223> OTHER INFORMATION: Artificially Mutated Variable Region of Light
      Chain
<220> FEATURE:
<221> NAME/KEY: misc_feature
<222> LOCATION: (1)..(107)
<223> OTHER INFORMATION: Variable Region of Light Chain(matu014)

<400> SEQUENCE: 35

Glu Thr Thr Val Thr Gln Ser Pro Ser Ser Leu Ser Ala Ser Val Gly
1               5                   10                  15

Asp Arg Val Thr Ile Arg Cys Ile Thr Asn Ile Asp Ile Asp Asp Glu
                20                  25                  30

Met Asn Trp Tyr Gln Gln Lys Pro Gly Lys Gly Pro Lys Leu Leu Ile
            35                  40                  45

Ser Glu Gly Asn Thr Leu Arg Pro Gly Val Pro Ser Arg Phe Ser Ser
        50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Leu Gln Ser Asp Asn Leu Pro Tyr
                85                  90                  95

Thr Phe Gly Arg Gly Thr Lys Leu Glu Ile Lys
            100                 105

<210> SEQ ID NO 36
```

```
<211> LENGTH: 123
<212> TYPE: PRT
<213> ORGANISM: Artificial Sequence
<220> FEATURE:
<223> OTHER INFORMATION: Artificially Mutated Variable Region of Heavy
      Chain
<220> FEATURE:
<221> NAME/KEY: misc_feature
<222> LOCATION: (1)..(123)
<223> OTHER INFORMATION: Variable Region of Heavy Chain(matu014)

<400> SEQUENCE: 36

Glu Val Gln Leu Val Glu Ser Gly Gly Gly Leu Val Lys Pro Gly Gly
1               5                   10                  15

Tyr Leu Arg Leu Ser Cys Ala Ala Ser Gly Phe Thr Phe Ser Ser Tyr
            20                  25                  30

Ala Met Ser Trp Val Arg Gln Thr Pro Gly Lys Gly Leu Asp Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Val Lys Asn Ser Leu Tyr
65                  70                  75                  80

Leu Gln Met Asn Ser Leu Thr Asp Asp Thr Ala Val Tyr Phe Cys
                85                  90                  95

Ala Arg His Asn Tyr Arg Tyr Asp Glu Tyr Tyr Tyr Ala Met Asp Tyr
            100                 105                 110

Trp Gly Gln Gly Thr Leu Val Thr Val Ser Ser
        115                 120

<210> SEQ ID NO 37
<211> LENGTH: 11
<212> TYPE: PRT
<213> ORGANISM: Artificial Sequence
<220> FEATURE:
<223> OTHER INFORMATION: CDR1 of Artificially Mutated Variable Region of
      Light Chain
<220> FEATURE:
<221> NAME/KEY: misc_feature
<222> LOCATION: (1)..(11)
<223> OTHER INFORMATION: CDR1 of Light Chain(matu020)

<400> SEQUENCE: 37

Ile Thr Ser Ile Asp Ile Asp Asp Glu Met Asn
1               5                   10

<210> SEQ ID NO 38
<211> LENGTH: 7
<212> TYPE: PRT
<213> ORGANISM: Mus musculus
<220> FEATURE:
<221> NAME/KEY: misc_feature
<222> LOCATION: (1)..(7)
<223> OTHER INFORMATION: CDR2 of Light Chain(matu020)

<400> SEQUENCE: 38

Glu Gly Asn Thr Leu Arg Pro
1               5

<210> SEQ ID NO 39
<211> LENGTH: 9
<212> TYPE: PRT
<213> ORGANISM: Mus musculus
<220> FEATURE:
<221> NAME/KEY: misc_feature
<222> LOCATION: (1)..(9)
<223> OTHER INFORMATION: CDR3 of Light Chain(matu020)
```

```
<400> SEQUENCE: 39

Leu Gln Ser Asp Asn Leu Pro Tyr Thr
1               5

<210> SEQ ID NO 40
<211> LENGTH: 5
<212> TYPE: PRT
<213> ORGANISM: Mus musculus
<220> FEATURE:
<221> NAME/KEY: misc_feature
<222> LOCATION: (1)..(5)
<223> OTHER INFORMATION: CDR1 of Heavy Chain(matu020)

<400> SEQUENCE: 40

Ser Tyr Ala Met Ser
1               5

<210> SEQ ID NO 41
<211> LENGTH: 17
<212> TYPE: PRT
<213> ORGANISM: Mus musculus
<220> FEATURE:
<221> NAME/KEY: misc_feature
<222> LOCATION: (1)..(17)
<223> OTHER INFORMATION: CDR2 of Heavy Chain(matu020)

<400> SEQUENCE: 41

Thr Ile Ser Ser Gly Gly Ser Tyr Thr Tyr Tyr Pro Asp Ser Val Lys
1               5                   10                  15

Gly

<210> SEQ ID NO 42
<211> LENGTH: 14
<212> TYPE: PRT
<213> ORGANISM: Artificial Sequence
<220> FEATURE:
<223> OTHER INFORMATION: CDR3 of Artificially Mutated Variable Region of
      Heavy Chain
<220> FEATURE:
<221> NAME/KEY: misc_feature
<222> LOCATION: (1)..(14)
<223> OTHER INFORMATION: CDR3 of Heavy Chain(matu020)

<400> SEQUENCE: 42

His Asn Tyr Arg Tyr Asp Glu Tyr Tyr His Ala Met Asp Tyr
1               5                   10

<210> SEQ ID NO 43
<211> LENGTH: 107
<212> TYPE: PRT
<213> ORGANISM: Artificial Sequence
<220> FEATURE:
<223> OTHER INFORMATION: Artificially Mutated Variable Region of Light
      Chain
<220> FEATURE:
<221> NAME/KEY: misc_feature
<222> LOCATION: (1)..(107)
<223> OTHER INFORMATION: Variable Region of Light Chain(matu020)

<400> SEQUENCE: 43

Glu Thr Thr Val Thr Gln Ser Pro Ser Ser Leu Ser Ala Ser Val Gly
1               5                   10                  15

Asp Arg Val Thr Ile Arg Cys Ile Thr Ser Ile Asp Ile Asp Asp Glu
                20                  25                  30

Met Asn Trp Tyr Gln Gln Lys Pro Gly Lys Gly Pro Lys Leu Leu Ile
            35                  40                  45
```

Ser Glu Gly Asn Thr Leu Arg Pro Gly Val Pro Ser Arg Phe Ser Ser
            50                  55                  60

Ser Gly Tyr Gly Thr Asp Phe Thr Leu Thr Ile Ser Ser Leu Gln Pro
 65                  70                  75                  80

Glu Asp Phe Ala Thr Tyr Tyr Cys Leu Gln Ser Asp Asn Leu Pro Tyr
                 85                  90                  95

Thr Phe Gly Gln Gly Thr Lys Leu Glu Ile Lys
            100                 105

<210> SEQ ID NO 44
<211> LENGTH: 123
<212> TYPE: PRT
<213> ORGANISM: Artificial Sequence
<220> FEATURE:
<223> OTHER INFORMATION: Artificially Mutated Variable Region of Heavy
      Chain
<220> FEATURE:
<221> NAME/KEY: misc_feature
<222> LOCATION: (1)..(123)
<223> OTHER INFORMATION: Variable Region of Heavy Chain(matu020)

<400> SEQUENCE: 44

Glu Val Gln Leu Val Glu Ser Gly Gly Gly Leu Val Lys Pro Gly Gly
1               5                   10                  15

Tyr Gln Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Asp Trp Val
        35                  40                  45

Ala Thr Ile Ser Ser Gly Gly Ser Tyr Thr Tyr Tyr Pro Asp Ser Val
 50                  55                  60

Lys Gly Arg Phe Thr Ile Ser Arg Asp Asn Ala Lys Asn Ser Leu Tyr
 65                  70                  75                  80

Leu Gln Met Asn Asn Leu Thr Asp Asp Thr Ala Val Tyr Phe Cys
                 85                  90                  95

Ala Arg His Asn Tyr Arg Tyr Asp Glu Tyr Tyr His Ala Met Asp Tyr
            100                 105                 110

Trp Gly Gln Gly Thr Leu Val Thr Val Ser Ser
        115                 120

<210> SEQ ID NO 45
<211> LENGTH: 11
<212> TYPE: PRT
<213> ORGANISM: Artificial Sequence
<220> FEATURE:
<223> OTHER INFORMATION: CDR1 of Artificially Mutated Variable Region of
      Light Chain
<220> FEATURE:
<221> NAME/KEY: misc_feature
<222> LOCATION: (1)..(11)
<223> OTHER INFORMATION: CDR1 of Light Chain(matu024)

<400> SEQUENCE: 45

Ile Thr Ser Ile Asp Ile Asp Asp Glu Met Asn
1               5                   10

<210> SEQ ID NO 46
<211> LENGTH: 7
<212> TYPE: PRT
<213> ORGANISM: Mus musculus
<220> FEATURE:
<221> NAME/KEY: misc_feature
<222> LOCATION: (1)..(7)
<223> OTHER INFORMATION: CDR2 of Light Chain(matu024)

<400> SEQUENCE: 46

Glu Gly Asn Thr Leu Arg Pro
1               5

<210> SEQ ID NO 47
<211> LENGTH: 9
<212> TYPE: PRT
<213> ORGANISM: Mus musculus
<220> FEATURE:
<221> NAME/KEY: misc_feature
<222> LOCATION: (1)..(9)
<223> OTHER INFORMATION: CDR3 of Light Chain(matu024)

<400> SEQUENCE: 47

Leu Gln Ser Asp Asn Leu Pro Tyr Thr
1               5

<210> SEQ ID NO 48
<211> LENGTH: 5
<212> TYPE: PRT
<213> ORGANISM: Mus musculus
<220> FEATURE:
<221> NAME/KEY: misc_feature
<222> LOCATION: (1)..(5)
<223> OTHER INFORMATION: CDR1 of Heavy Chain(matu024)

<400> SEQUENCE: 48

Ser Tyr Ala Met Ser
1               5

<210> SEQ ID NO 49
<211> LENGTH: 17
<212> TYPE: PRT
<213> ORGANISM: Mus musculus
<220> FEATURE:
<221> NAME/KEY: misc_feature
<222> LOCATION: (1)..(17)
<223> OTHER INFORMATION: CDR2 of Heavy Chain(matu024)

<400> SEQUENCE: 49

Thr Ile Ser Ser Gly Gly Ser Tyr Thr Tyr Tyr Pro Asp Ser Val Lys
1               5                   10                  15

Gly

<210> SEQ ID NO 50
<211> LENGTH: 14
<212> TYPE: PRT
<213> ORGANISM: Artificial Sequence
<220> FEATURE:
<223> OTHER INFORMATION: CDR3 of Artificially Mutated Variable Region of
      Heavy Chain
<220> FEATURE:
<221> NAME/KEY: misc_feature
<222> LOCATION: (1)..(14)
<223> OTHER INFORMATION: CDR3 of Heavy Chain(matu024)

<400> SEQUENCE: 50

His Asn Tyr Arg Tyr Gly Glu Tyr Tyr Tyr Ala Met Asp Tyr
1               5                   10

<210> SEQ ID NO 51
<211> LENGTH: 107
<212> TYPE: PRT
<213> ORGANISM: Artificial Sequence
<220> FEATURE:
<223> OTHER INFORMATION: Artificially Mutated Variable Region of Light
      Chain

```
<220> FEATURE:
<221> NAME/KEY: misc_feature
<222> LOCATION: (1)..(107)
<223> OTHER INFORMATION: Variable Region of Light Chain(matu024)

<400> SEQUENCE: 51
```

Glu Thr Thr Val Thr Gln Ser Pro Ser Ser Leu Ser Ala Ser Val Gly
1               5                   10                  15

Asp Arg Val Thr Ile Arg Cys Ile Thr Ser Ile Asp Ile Asp Asp Glu
            20                  25                  30

Met Asn Trp Tyr Gln Gln Lys Ser Gly Lys Gly Pro Lys Leu Leu Ile
        35                  40                  45

Ser Glu Gly Asn Thr Leu Arg Pro Gly Val Pro Ser Arg Phe Ser Ser
50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Leu Gln Ser Asp Asn Leu Pro Tyr
                85                  90                  95

Thr Phe Gly Gln Gly Thr Lys Leu Glu Ile Lys
            100                 105

```
<210> SEQ ID NO 52
<211> LENGTH: 123
<212> TYPE: PRT
<213> ORGANISM: Artificial Sequence
<220> FEATURE:
<223> OTHER INFORMATION: Artificially Mutated Variable Region of Heavy
      Chain
<220> FEATURE:
<221> NAME/KEY: misc_feature
<222> LOCATION: (1)..(123)
<223> OTHER INFORMATION: Variable Region of Heavy Chain(matu024)

<400> SEQUENCE: 52
```

Glu Val Gln Leu Val Glu Ser Gly Gly Gly Leu Val Lys Pro Gly Gly
1               5                   10                  15

Tyr Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Asp Trp Val
        35                  40                  45

Ala Thr Ile Ser Ser Gly Gly Ser Tyr Thr Tyr Tyr Pro Asp Ser Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Thr Asp Asp Asp Thr Ala Val Tyr Phe Cys
                85                  90                  95

Ala Arg His Asn Tyr Arg Tyr Gly Glu Tyr Tyr Tyr Ala Met Asp Tyr
            100                 105                 110

Trp Gly Gln Gly Thr Leu Val Thr Val Ser Ser
        115                 120

```
<210> SEQ ID NO 53
<211> LENGTH: 11
<212> TYPE: PRT
<213> ORGANISM: Artificial Sequence
<220> FEATURE:
<223> OTHER INFORMATION: CDR1 of Artificially Mutated Variable Region of
      Light Chain
<220> FEATURE:
<221> NAME/KEY: misc_feature
<222> LOCATION: (1)..(11)
<223> OTHER INFORMATION: CDR1 of Light Chain(matu039)
```

```
<400> SEQUENCE: 53

Lys Thr Ser Ile Asp Ile Asp Asp Glu Met Asn
1               5                   10

<210> SEQ ID NO 54
<211> LENGTH: 7
<212> TYPE: PRT
<213> ORGANISM: Mus musculus
<220> FEATURE:
<221> NAME/KEY: misc_feature
<222> LOCATION: (1)..(7)
<223> OTHER INFORMATION: CDR2 of Light Chain(matu039)

<400> SEQUENCE: 54

Glu Gly Asn Thr Leu Arg Pro
1               5

<210> SEQ ID NO 55
<211> LENGTH: 9
<212> TYPE: PRT
<213> ORGANISM: Mus musculus
<220> FEATURE:
<221> NAME/KEY: misc_feature
<222> LOCATION: (1)..(9)
<223> OTHER INFORMATION: CDR3 of Light Chain(matu039)

<400> SEQUENCE: 55

Leu Gln Ser Asp Asn Leu Pro Tyr Thr
1               5

<210> SEQ ID NO 56
<211> LENGTH: 5
<212> TYPE: PRT
<213> ORGANISM: Mus musculus
<220> FEATURE:
<221> NAME/KEY: misc_feature
<222> LOCATION: (1)..(5)
<223> OTHER INFORMATION: CDR1 of Heavy Chain(matu039)

<400> SEQUENCE: 56

Ser Tyr Ala Met Ser
1               5

<210> SEQ ID NO 57
<211> LENGTH: 17
<212> TYPE: PRT
<213> ORGANISM: Artificial Sequence
<220> FEATURE:
<223> OTHER INFORMATION: CDR2 of Artificially Mutated Variable Region of
      Heavy Chain
<220> FEATURE:
<221> NAME/KEY: misc_feature
<222> LOCATION: (1)..(17)
<223> OTHER INFORMATION: CDR2 of Heavy Chain(matu039)

<400> SEQUENCE: 57

Thr Ile Ser Ser Gly Gly Ser Tyr Thr Tyr Tyr Pro Asp Ser Val Lys
1               5                   10                  15

Glu

<210> SEQ ID NO 58
<211> LENGTH: 14
<212> TYPE: PRT
<213> ORGANISM: Artificial Sequence
<220> FEATURE:
<223> OTHER INFORMATION: CDR3 of Artificially Mutated Variable Region of
      Heavy Chain
```

```
<220> FEATURE:
<221> NAME/KEY: misc_feature
<222> LOCATION: (1)..(14)
<223> OTHER INFORMATION: CDR3 of Heavy Chain(matu039)

<400> SEQUENCE: 58

His Asn Tyr Arg Tyr Asp Glu Tyr Tyr Tyr Gly Met Asp Tyr
1               5                   10

<210> SEQ ID NO 59
<211> LENGTH: 107
<212> TYPE: PRT
<213> ORGANISM: Artificial Sequence
<220> FEATURE:
<223> OTHER INFORMATION: Artificially Mutated Variable Region of Light
      Chain
<220> FEATURE:
<221> NAME/KEY: misc_feature
<222> LOCATION: (1)..(107)
<223> OTHER INFORMATION: Variable Region of Light Chain(matu039)

<400> SEQUENCE: 59

Glu Thr Thr Val Thr Gln Ser Pro Ser Ser Leu Ser Ala Ser Val Gly
1               5                   10                  15

Asp Arg Val Thr Ile Arg Cys Lys Thr Ser Ile Asp Ile Asp Asp Glu
            20                  25                  30

Met Asn Trp Tyr Gln Gln Lys Pro Gly Lys Gly Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Leu Gln Ser Asp Asn Leu Pro Tyr
                85                  90                  95

Thr Phe Gly Gln Gly Thr Lys Leu Gly Ile Lys
            100                 105

<210> SEQ ID NO 60
<211> LENGTH: 123
<212> TYPE: PRT
<213> ORGANISM: Artificial Sequence
<220> FEATURE:
<223> OTHER INFORMATION: Artificially Mutated Variable Region of Heavy
      Chain
<220> FEATURE:
<221> NAME/KEY: misc_feature
<222> LOCATION: (1)..(123)
<223> OTHER INFORMATION: Variable Region of Heavy Chain(matu039)

<400> SEQUENCE: 60

Glu Val Arg Leu Val Glu Ser Gly Gly Gly Leu Val Lys Pro Gly Gly
1               5                   10                  15

Tyr Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Asp Trp Val
        35                  40                  45

Ala Thr Ile Ser Ser Gly Gly Ser Tyr Thr Tyr Tyr Pro Asp Ser Val
    50                  55                  60

Lys Glu Arg Phe Thr Ile Ser Arg Asp Asn Ala Lys Asn Ser Leu Tyr
65                  70                  75                  80

Leu Gln Met Asn Ser Leu Thr Asp Asp Thr Ala Val Tyr Phe Cys
                85                  90                  95
```

Ala Arg His Asn Tyr Arg Tyr Asp Glu Tyr Tyr Tyr Gly Met Asp Tyr
                100                 105                 110

Trp Gly Gln Gly Thr Leu Val Thr Val Ser Ser
        115                 120

<210> SEQ ID NO 61
<211> LENGTH: 11
<212> TYPE: PRT
<213> ORGANISM: Artificial Sequence
<220> FEATURE:
<223> OTHER INFORMATION: CDR1 of Artificially Mutated Variable Region of
      Light Chain
<220> FEATURE:
<221> NAME/KEY: misc_feature
<222> LOCATION: (1)..(11)
<223> OTHER INFORMATION: CDR1 of Light Chain(matu054)

<400> SEQUENCE: 61

Ile Thr Ser Ile Asp Ile Glu Asp Glu Met Asn
1               5                   10

<210> SEQ ID NO 62
<211> LENGTH: 7
<212> TYPE: PRT
<213> ORGANISM: Mus musculus
<220> FEATURE:
<221> NAME/KEY: misc_feature
<222> LOCATION: (1)..(7)
<223> OTHER INFORMATION: CDR2 of Light Chain(matu054)

<400> SEQUENCE: 62

Glu Gly Asn Thr Leu Arg Pro
1               5

<210> SEQ ID NO 63
<211> LENGTH: 9
<212> TYPE: PRT
<213> ORGANISM: Mus musculus
<220> FEATURE:
<221> NAME/KEY: misc_feature
<222> LOCATION: (1)..(9)
<223> OTHER INFORMATION: CDR3 of Light Chain(matu054)

<400> SEQUENCE: 63

Leu Gln Ser Asp Asn Leu Pro Tyr Thr
1               5

<210> SEQ ID NO 64
<211> LENGTH: 5
<212> TYPE: PRT
<213> ORGANISM: Mus musculus
<220> FEATURE:
<221> NAME/KEY: misc_feature
<222> LOCATION: (1)..(5)
<223> OTHER INFORMATION: CDR1 of Heavy Chain(matu054)

<400> SEQUENCE: 64

Ser Tyr Ala Met Ser
1               5

<210> SEQ ID NO 65
<211> LENGTH: 17
<212> TYPE: PRT
<213> ORGANISM: Mus musculus
<220> FEATURE:
<221> NAME/KEY: misc_feature
<222> LOCATION: (1)..(17)
<223> OTHER INFORMATION: CDR2 of Heavy Chain(matu054)

<400> SEQUENCE: 65

Thr Ile Ser Ser Gly Gly Ser Tyr Thr Tyr Tyr Pro Asp Ser Val Lys
1               5                   10                  15

Gly

<210> SEQ ID NO 66
<211> LENGTH: 14
<212> TYPE: PRT
<213> ORGANISM: Mus musculus
<220> FEATURE:
<221> NAME/KEY: misc_feature
<222> LOCATION: (1)..(14)
<223> OTHER INFORMATION: CDR3 of Heavy Chain(matu054)

<400> SEQUENCE: 66

His Asn Tyr Arg Tyr Asp Glu Tyr Tyr Tyr Ala Met Asp Tyr
1               5                   10

<210> SEQ ID NO 67
<211> LENGTH: 107
<212> TYPE: PRT
<213> ORGANISM: Artificial Sequence
<220> FEATURE:
<223> OTHER INFORMATION: Artificially Mutated Variable Region of Light
      Chain
<220> FEATURE:
<221> NAME/KEY: misc_feature
<222> LOCATION: (1)..(107)
<223> OTHER INFORMATION: Variable Region of Light Chain(matu054)

<400> SEQUENCE: 67

Glu Thr Thr Val Thr Gln Ser Pro Ser Ser Leu Ser Ala Ser Val Gly
1               5                   10                  15

Asp Arg Val Thr Ile Arg Cys Ile Thr Ser Ile Asp Ile Glu Asp Glu
            20                  25                  30

Met Asn Trp Tyr Gln Gln Lys Pro Gly Lys Gly Pro Lys Leu Leu Ile
        35                  40                  45

Ser Glu Gly Asn Thr Leu Arg Pro Gly Val Pro Ser Arg Phe Ser Ser
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Leu Gln Ser Asp Asn Leu Pro Tyr
                85                  90                  95

Thr Phe Gly Gln Gly Thr Lys Leu Glu Ile Lys
            100                 105

<210> SEQ ID NO 68
<211> LENGTH: 123
<212> TYPE: PRT
<213> ORGANISM: Artificial Sequence
<220> FEATURE:
<223> OTHER INFORMATION: Artificially Mutated Variable Region of Heavy
      Chain
<220> FEATURE:
<221> NAME/KEY: misc_feature
<222> LOCATION: (1)..(123)
<223> OTHER INFORMATION: Variable Region of Heavy Chain(matu054)

<400> SEQUENCE: 68

Glu Val Gln Leu Val Glu Ser Gly Gly Gly Leu Val Lys Pro Gly Gly
1               5                   10                  15

Tyr Leu Arg Leu Ser Cys Ala Ala Ser Gly Phe Thr Phe Ser Ser Tyr
            20                  25                  30

```
Ala Met Ser Trp Val Arg Gln Ala Pro Gly Lys Gly Leu Asp Trp Val
             35                  40                  45
Ala Thr Ile Ser Ser Gly Gly Ser Tyr Thr Tyr Tyr Pro Asp Ser Val
 50                  55                  60
Lys Gly Arg Phe Thr Ile Ser Arg Asp Asn Thr Lys Asn Thr Leu Tyr
 65                  70                  75                  80
Leu Gln Met Asn Ser Leu Thr Asp Asp Thr Ala Val Tyr Phe Cys
                 85                  90                  95
Ala Arg His Asn Tyr Arg Tyr Asp Glu Tyr Tyr Tyr Ala Met Asp Tyr
             100                 105                 110
Trp Gly Gln Gly Thr Leu Val Thr Val Ser Ser
        115                 120
```

<210> SEQ ID NO 69
<211> LENGTH: 11
<212> TYPE: PRT
<213> ORGANISM: Artificial Sequence
<220> FEATURE:
<223> OTHER INFORMATION: CDR1 of Artificially Mutated Variable Region of
      Light Chain
<220> FEATURE:
<221> NAME/KEY: misc_feature
<222> LOCATION: (1)..(11)
<223> OTHER INFORMATION: CDR1 of Light Chain(matu062)

<400> SEQUENCE: 69

```
Ile Thr Asn Ile Asp Ile Asp Asp Glu Met Asn
 1               5                  10
```

<210> SEQ ID NO 70
<211> LENGTH: 7
<212> TYPE: PRT
<213> ORGANISM: Mus musculus
<220> FEATURE:
<221> NAME/KEY: misc_feature
<222> LOCATION: (1)..(7)
<223> OTHER INFORMATION: CDR2 of Light Chain(matu062)

<400> SEQUENCE: 70

```
Glu Gly Asn Thr Leu Arg Pro
 1               5
```

<210> SEQ ID NO 71
<211> LENGTH: 9
<212> TYPE: PRT
<213> ORGANISM: Artificial Sequence
<220> FEATURE:
<223> OTHER INFORMATION: CDR3 of Artificially Mutated Variable Region of
      Light Chain
<220> FEATURE:
<221> NAME/KEY: misc_feature
<222> LOCATION: (1)..(9)
<223> OTHER INFORMATION: CDR3 of Light Chain(matu062)

<400> SEQUENCE: 71

```
Met Gln Ser Asp Asn Leu Pro Tyr Thr
 1               5
```

<210> SEQ ID NO 72
<211> LENGTH: 5
<212> TYPE: PRT
<213> ORGANISM: Mus musculus
<220> FEATURE:
<221> NAME/KEY: misc_feature
<222> LOCATION: (1)..(5)
<223> OTHER INFORMATION: CDR1 of Heavy Chain(matu062)

```
<400> SEQUENCE: 72

Ser Tyr Ala Met Ser
1               5

<210> SEQ ID NO 73
<211> LENGTH: 17
<212> TYPE: PRT
<213> ORGANISM: Mus musculus
<220> FEATURE:
<221> NAME/KEY: misc_feature
<222> LOCATION: (1)..(17)
<223> OTHER INFORMATION: CDR2 of Heavy Chain(matu062)

<400> SEQUENCE: 73

Thr Ile Ser Ser Gly Gly Ser Tyr Thr Tyr Tyr Pro Asp Ser Val Lys
1               5                   10                  15

Gly

<210> SEQ ID NO 74
<211> LENGTH: 14
<212> TYPE: PRT
<213> ORGANISM: Mus musculus
<220> FEATURE:
<221> NAME/KEY: misc_feature
<222> LOCATION: (1)..(14)
<223> OTHER INFORMATION: CDR3 of Heavy Chain(matu062)

<400> SEQUENCE: 74

His Asn Tyr Arg Tyr Asp Glu Tyr Tyr Tyr Ala Met Asp Tyr
1               5                   10

<210> SEQ ID NO 75
<211> LENGTH: 107
<212> TYPE: PRT
<213> ORGANISM: Artificial Sequence
<220> FEATURE:
<223> OTHER INFORMATION: Artificially Mutated Variable Region of Light
      Chain
<220> FEATURE:
<221> NAME/KEY: misc_feature
<222> LOCATION: (1)..(107)
<223> OTHER INFORMATION: Variable Region of Light Chain(matu062)

<400> SEQUENCE: 75

Glu Thr Thr Val Thr Gln Ser Pro Ser Ser Leu Ser Ala Phe Val Gly
1               5                   10                  15

Gly Arg Val Ala Ile Arg Cys Ile Thr Asn Ile Asp Ile Asp Asp Glu
                20                  25                  30

Met Asn Trp Tyr Gln Gln Lys Pro Gly Lys Pro Lys Leu Leu Ile
            35                  40                  45

Ser Glu Gly Asn Thr Leu Arg Pro Gly Val Pro Ser Arg Phe Ser Ser
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Met Gln Ser Asp Asn Leu Pro Tyr
                85                  90                  95

Thr Phe Gly Gln Gly Thr Lys Leu Glu Ile Lys
            100                 105

<210> SEQ ID NO 76
<211> LENGTH: 123
<212> TYPE: PRT
<213> ORGANISM: Artificial Sequence
<220> FEATURE:
```

<223> OTHER INFORMATION: Artificially Mutated Variable Region of Heavy
      Chain
<220> FEATURE:
<221> NAME/KEY: misc_feature
<222> LOCATION: (1)..(123)
<223> OTHER INFORMATION: Variable Region of Heavy Chain(matu062)

<400> SEQUENCE: 76

Glu Val Gln Leu Val Glu Ser Gly Gly Gly Leu Val Lys Pro Gly Gly
1               5                   10                  15

Tyr Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Asp Trp Val
        35                  40                  45

Ala Thr Ile Ser Ser Gly Gly Ser Tyr Thr Tyr Tyr Pro Asp Ser Val
    50                  55                  60

Lys Gly Arg Phe Thr Ile Ser Arg Asp Asn Ala Glu Asn Thr Leu Tyr
65                  70                  75                  80

Leu Gln Met Asn Ser Leu Thr Asn Asp Asp Thr Ala Val Tyr Phe Cys
                85                  90                  95

Ala Arg His Asn Tyr Arg Tyr Asp Glu Tyr Tyr Tyr Ala Met Asp Tyr
            100                 105                 110

Trp Gly Gln Gly Thr Leu Val Thr Val Ser Ser
        115                 120

<210> SEQ ID NO 77
<211> LENGTH: 11
<212> TYPE: PRT
<213> ORGANISM: Artificial Sequence
<220> FEATURE:
<223> OTHER INFORMATION: CDR1 of Artificially Mutated Variable Region of
      Light Chain
<220> FEATURE:
<221> NAME/KEY: misc_feature
<222> LOCATION: (1)..(11)
<223> OTHER INFORMATION: CDR1 of Light Chain(matu072)

<400> SEQUENCE: 77

Ile Thr Ser Ile Asp Ile Asp Asp Glu Met Asn
1               5                   10

<210> SEQ ID NO 78
<211> LENGTH: 7
<212> TYPE: PRT
<213> ORGANISM: Mus musculus
<220> FEATURE:
<221> NAME/KEY: misc_feature
<222> LOCATION: (1)..(7)
<223> OTHER INFORMATION: CDR2 of Light Chain(matu072)

<400> SEQUENCE: 78

Glu Gly Asn Thr Leu Arg Pro
1               5

<210> SEQ ID NO 79
<211> LENGTH: 9
<212> TYPE: PRT
<213> ORGANISM: Mus musculus
<220> FEATURE:
<221> NAME/KEY: misc_feature
<222> LOCATION: (1)..(9)
<223> OTHER INFORMATION: CDR3 of Light Chain(matu072)

<400> SEQUENCE: 79

Leu Gln Ser Asp Asn Leu Pro Tyr Thr

-continued

```
<210> SEQ ID NO 80
<211> LENGTH: 5
<212> TYPE: PRT
<213> ORGANISM: Mus musculus
<220> FEATURE:
<221> NAME/KEY: misc_feature
<222> LOCATION: (1)..(5)
<223> OTHER INFORMATION: CDR1 of Heavy Chain(matu072)

<400> SEQUENCE: 80

Ser Tyr Ala Met Ser
1               5

<210> SEQ ID NO 81
<211> LENGTH: 17
<212> TYPE: PRT
<213> ORGANISM: Artificial Sequence
<220> FEATURE:
<223> OTHER INFORMATION: CDR2 of Artificially Mutated Variable Region of
      Heavy Chain
<220> FEATURE:
<221> NAME/KEY: misc_feature
<222> LOCATION: (1)..(17)
<223> OTHER INFORMATION: CDR2 of Heavy Chain(matu072)

<400> SEQUENCE: 81

Thr Ile Ser Ser Gly Gly Ser Tyr Thr Tyr Tyr Pro Asp Asn Val Lys
1               5                   10                  15

Gly

<210> SEQ ID NO 82
<211> LENGTH: 14
<212> TYPE: PRT
<213> ORGANISM: Artificial Sequence
<220> FEATURE:
<223> OTHER INFORMATION: CDR3 of Artificially Mutated Variable Region of
      Heavy Chain
<220> FEATURE:
<221> NAME/KEY: misc_feature
<222> LOCATION: (1)..(14)
<223> OTHER INFORMATION: CDR3 of Heavy Chain(matu072)

<400> SEQUENCE: 82

His Asn Tyr Arg Tyr Asp Glu Tyr Tyr His Ala Met Asp Tyr
1               5                   10

<210> SEQ ID NO 83
<211> LENGTH: 107
<212> TYPE: PRT
<213> ORGANISM: Artificial Sequence
<220> FEATURE:
<223> OTHER INFORMATION: Artificially Mutated Variable Region of Light
      Chain
<220> FEATURE:
<221> NAME/KEY: misc_feature
<222> LOCATION: (1)..(107)
<223> OTHER INFORMATION: Variable Region of Light Chain(matu072)

<400> SEQUENCE: 83

Glu Thr Thr Val Thr Gln Ser Pro Ser Ser Leu Phe Ala Ser Val Gly
1               5                   10                  15

Asp Lys Val Thr Ile Arg Cys Ile Thr Ser Ile Asp Ile Asp Asp Glu
                20                  25                  30

Met Asn Trp Tyr Gln Gln Lys Pro Gly Lys Pro Lys Leu Leu Ile
            35                  40                  45
```

```
Ser Glu Gly Asn Thr Leu Arg Pro Gly Val Pro Ser Arg Phe Ser Ser
    50                  55                  60

Ser Gly Tyr Gly Thr Asp Phe Thr Leu Thr Ile Ser Ser Leu Gln Pro
65                  70                  75                  80

Glu Asp Phe Ala Thr Tyr Tyr Cys Leu Gln Ser Asp Asn Leu Pro Tyr
                85                  90                  95

Thr Phe Gly Gln Gly Thr Lys Leu Glu Ile Lys
            100                 105
```

<210> SEQ ID NO 84
<211> LENGTH: 123
<212> TYPE: PRT
<213> ORGANISM: Artificial Sequence
<220> FEATURE:
<223> OTHER INFORMATION: Artificially Mutated Variable Region of Heavy
      Chain
<220> FEATURE:
<221> NAME/KEY: misc_feature
<222> LOCATION: (1)..(123)
<223> OTHER INFORMATION: Variable Region of Heavy Chain(matu072)

<400> SEQUENCE: 84

```
Glu Val Gln Leu Val Glu Ser Gly Gly Leu Val Lys Pro Gly Gly
1               5                   10                  15

Tyr Leu Arg Leu Ser Cys Ala Ala Ser Gly Phe Thr Phe Ser Ser Tyr
                20                  25                  30

Ala Met Ser Trp Val Arg Gln Ala Pro Gly Lys Gly Leu Asp Trp Val
            35                  40                  45

Ala Thr Ile Ser Ser Gly Gly Ser Tyr Thr Tyr Tyr Pro Asp Asn Val
50                  55                  60

Lys Gly Arg Phe Thr Ile Ser Arg Asp Asn Ala Lys Asn Ser Leu Tyr
65                  70                  75                  80

Leu Gln Met Asn Ser Leu Thr Asp Asp Asp Thr Ala Val Tyr Phe Cys
                85                  90                  95

Ala Arg His Asn Tyr Arg Tyr Asp Glu Tyr Tyr His Ala Met Asp Tyr
                100                 105                 110

Trp Gly Gln Gly Thr Leu Val Thr Val Ser Ser
        115                 120
```

<210> SEQ ID NO 85
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 85
gagtcgcctc ttagcggatg c                                              21

<210> SEQ ID NO 86
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 86
gctccttggc atccaggctt g                                              21

<210> SEQ ID NO 87
<211> LENGTH: 21
<212> TYPE: DNA

```
<213> ORGANISM: Artificial Sequence
<220> FEATURE:
<223> OTHER INFORMATION: Artificially Synthesized Primer Sequence

<400> SEQUENCE: 87
cggatgcagc accgaggctt c                                           21

<210> SEQ ID NO 88
<211> LENGTH: 22
<212> TYPE: DNA
<213> ORGANISM: Artificial Sequence
<220> FEATURE:
<223> OTHER INFORMATION: Artificially Synthesized Primer Sequence

<400> SEQUENCE: 88
ggcttggcgt ctagtccttt cc                                          22

<210> SEQ ID NO 89
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 89
aagcatcgag cagtgagcga gatg                                        24

<210> SEQ ID NO 90
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 90
aacaagtatc agggtgggga gaac                                        24

<210> SEQ ID NO 91
<211> LENGTH: 22
<212> TYPE: DNA
<213> ORGANISM: Artificial Sequence
<220> FEATURE:
<223> OTHER INFORMATION: Artificially Synthesized Primer Sequence

<400> SEQUENCE: 91
gatgcagcac cgaggcttct tc                                          22

<210> SEQ ID NO 92
<211> LENGTH: 22
<212> TYPE: DNA
<213> ORGANISM: Artificial Sequence
<220> FEATURE:
<223> OTHER INFORMATION: Artificially Synthesized Primer Sequence

<400> SEQUENCE: 92
tatggggagg ctcactttcc ag                                          22

<210> SEQ ID NO 93
<211> LENGTH: 36
<212> TYPE: DNA
<213> ORGANISM: Artificial Sequence
<220> FEATURE:
<223> OTHER INFORMATION: Artificially Synthesized Primer Sequence

<400> SEQUENCE: 93
aatagcggcc gcaccatgca gcaccgaggc ttcctc                           36
```

<210> SEQ ID NO 94
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 94
cgggatccgt cctttccctt ccctttcttg                              30

<210> SEQ ID NO 95
<211> LENGTH: 31
<212> TYPE: DNA
<213> ORGANISM: Artificial Sequence
<220> FEATURE:
<223> OTHER INFORMATION: Artificially Synthesized Primer Sequence

<400> SEQUENCE: 95
aatagcggcc gcggagtttg gagccgactg c                            31

<210> SEQ ID NO 96
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 96
cgggatccgt cctttccctt ccctttcttg                              30

<210> SEQ ID NO 97
<211> LENGTH: 36
<212> TYPE: DNA
<213> ORGANISM: Artificial Sequence
<220> FEATURE:
<223> OTHER INFORMATION: Artificially Synthesized Primer Sequence

<400> SEQUENCE: 97
aatagcggcc gcaccatgca gcaccgaggc ttcttc                       36

<210> SEQ ID NO 98
<211> LENGTH: 32
<212> TYPE: DNA
<213> ORGANISM: Artificial Sequence
<220> FEATURE:
<223> OTHER INFORMATION: Artificially Synthesized Primer Sequence

<400> SEQUENCE: 98
cgggatccgt cctttccttt tcctttcttg gc                           32

<210> SEQ ID NO 99
<211> LENGTH: 32
<212> TYPE: DNA
<213> ORGANISM: Artificial Sequence
<220> FEATURE:
<223> OTHER INFORMATION: Artificially Synthesized Primer Sequence

<400> SEQUENCE: 99
cgggatccaa aaagaaagat aaggtgaaga ag                           32

<210> SEQ ID NO 100
<211> LENGTH: 31
<212> TYPE: DNA
<213> ORGANISM: Artificial Sequence
<220> FEATURE:

<223> OTHER INFORMATION: Artificially Synthesized Primer Sequence

<400> SEQUENCE: 100
ccgctcgagg tcctttccct tccctttctt g                    31

<210> SEQ ID NO 101
<211> LENGTH: 29
<212> TYPE: DNA
<213> ORGANISM: Artificial Sequence
<220> FEATURE:
<223> OTHER INFORMATION: Artificially Synthesized Primer Sequence

<400> SEQUENCE: 101
cgggatccga gtttggagcc gactgcaag                       29

<210> SEQ ID NO 102
<211> LENGTH: 31
<212> TYPE: DNA
<213> ORGANISM: Artificial Sequence
<220> FEATURE:
<223> OTHER INFORMATION: Artificially Synthesized Primer Sequence

<400> SEQUENCE: 102
ccgctcgagg tcctttccct tccctttctt g                    31

<210> SEQ ID NO 103
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 103
ctcgagaaaa agaaagataa ggtg                            24

<210> SEQ ID NO 104
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 104
tctagactag tcctttccct tccc                            24

<210> SEQ ID NO 105
<211> LENGTH: 23
<212> TYPE: DNA
<213> ORGANISM: Artificial Sequence
<220> FEATURE:
<223> OTHER INFORMATION: Artificially Synthesized Primer Sequence

<400> SEQUENCE: 105
gagacgccat ccacgctgtt ttg                             23

<210> SEQ ID NO 106
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 106
cacgcacccg cgttctcaaa c                               21

```
<210> SEQ ID NO 107
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 107
gtttgagaac gcgggtgcgt g                                              21

<210> SEQ ID NO 108
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 108
gaggggcgga taaactcaat ggtg                                           24

<210> SEQ ID NO 109
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 109
cttggcggac ttgggtgcct g                                              21

<210> SEQ ID NO 110
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 110
caggcaccca agtccgccaa g                                              21

<210> SEQ ID NO 111
<211> LENGTH: 22
<212> TYPE: DNA
<213> ORGANISM: Artificial Sequence
<220> FEATURE:
<223> OTHER INFORMATION: Artificially Synthesized Primer Sequence

<400> SEQUENCE: 111
ggtgccttgc tggactttgg tg                                             22

<210> SEQ ID NO 112
<211> LENGTH: 22
<212> TYPE: DNA
<213> ORGANISM: Artificial Sequence
<220> FEATURE:
<223> OTHER INFORMATION: Artificially Synthesized Primer Sequence

<400> SEQUENCE: 112
caccaaagtc cagcaaggca cc                                             22

<210> SEQ ID NO 113
<211> LENGTH: 20
<212> TYPE: DNA
<213> ORGANISM: Artificial Sequence
<220> FEATURE:
<223> OTHER INFORMATION: Artificially Synthesized Primer Sequence
```

```
<400> SEQUENCE: 113
cagggctggg tgacgcggat                                        20

<210> SEQ ID NO 114
<211> LENGTH: 21
<212> TYPE: DNA
<213> ORGANISM: Artificial Sequence
<220> FEATURE:
<223> OTHER INFORMATION: Artificially Synthesized Primer Sequence

<400> SEQUENCE: 114
catccgcgtc acccagccct g                                      21

<210> SEQ ID NO 115
<211> LENGTH: 23
<212> TYPE: DNA
<213> ORGANISM: Artificial Sequence
<220> FEATURE:
<223> OTHER INFORMATION: Artificially Synthesized Primer Sequence

<400> SEQUENCE: 115
cgactggagc acgaggacac tga                                    23

<210> SEQ ID NO 116
<211> LENGTH: 19
<212> TYPE: DNA
<213> ORGANISM: Artificial Sequence
<220> FEATURE:
<223> OTHER INFORMATION: Artificially Synthesized Primer Sequence

<400> SEQUENCE: 116
aattttcttg tccacctgg                                         19

<210> SEQ ID NO 117
<211> LENGTH: 26
<212> TYPE: DNA
<213> ORGANISM: Artificial Sequence
<220> FEATURE:
<223> OTHER INFORMATION: Artificially Synthesized Primer Sequence

<400> SEQUENCE: 117
ctaacactca ttcctgttga agctct                                 26

<210> SEQ ID NO 118
<211> LENGTH: 57
<212> TYPE: DNA
<213> ORGANISM: Artificial Sequence
<220> FEATURE:
<223> OTHER INFORMATION: Artificially Synthesized Primer Sequence

<400> SEQUENCE: 118
gttctttctg tccgtgacca caggcgtgca ttctgaagtg atgctggtgg agtctgg    57

<210> SEQ ID NO 119
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 119
atatactcga gacggtgact gagg                                   24

<210> SEQ ID NO 120
<211> LENGTH: 66
```

```
<212> TYPE: DNA
<213> ORGANISM: Artificial Sequence
<220> FEATURE:
<223> OTHER INFORMATION: Artificially Synthesized Primer Sequence

<400> SEQUENCE: 120
atataaagct taccatggaa tggagctggg tgttcctgtt ctttctgtcc gtgaccacag      60
gcgtgc                                                                66

<210> SEQ ID NO 121
<211> LENGTH: 60
<212> TYPE: DNA
<213> ORGANISM: Artificial Sequence
<220> FEATURE:
<223> OTHER INFORMATION: Artificially Synthesized Primer Sequence

<400> SEQUENCE: 121
gggactgctg ctgctgtggc tgacagacgc ccgctgtgaa caactgtga cccagtctcc      60

<210> SEQ ID NO 122
<211> LENGTH: 32
<212> TYPE: DNA
<213> ORGANISM: Artificial Sequence
<220> FEATURE:
<223> OTHER INFORMATION: Artificially Synthesized Primer Sequence

<400> SEQUENCE: 122
atatacgtac gtttgatttc cagcttggtg cc                                   32

<210> SEQ ID NO 123
<211> LENGTH: 68
<212> TYPE: DNA
<213> ORGANISM: Artificial Sequence
<220> FEATURE:
<223> OTHER INFORMATION: Artificially Synthesized Primer Sequence

<400> SEQUENCE: 123
atataaagct taccatgtct gtgcctaccc aggtgctggg actgctgctg ctgtggctga      60
cagacgcc                                                              68

<210> SEQ ID NO 124
<211> LENGTH: 120
<212> TYPE: PRT
<213> ORGANISM: Homo sapiens
<220> FEATURE:
<221> NAME/KEY: misc_feature
<222> LOCATION: (1)..(120)
<223> OTHER INFORMATION: Variable Region of Heavy Chain(AF471493)

<400> SEQUENCE: 124

Glu Val Gln Leu Val Glu Ser Gly Gly Gly Leu Val Lys Pro Gly Gly
1               5                   10                  15

Tyr Leu Arg Leu Ser Cys Ala Ala Ser Gly Phe Thr Phe Ser Leu His
            20                  25                  30

Ser Met Ser Trp Val Arg Gln Ala Pro Gly Lys Gly Leu Asp Trp Val
        35                  40                  45

Ala Tyr Ile Thr Gly Ser Ser Asn Thr Ile Tyr Tyr Gly Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Thr Asp Asp Asp Thr Ala Val Tyr Phe Cys
                85                  90                  95
```

Ala Arg Gly Pro Ile Ser Ala Ala Asn Thr Phe Asp Leu Trp Gly Gln
            100                 105                 110

Gly Thr Leu Val Thr Val Ser Ser
        115                 120

<210> SEQ ID NO 125
<211> LENGTH: 29
<212> TYPE: PRT
<213> ORGANISM: Homo sapiens
<220> FEATURE:
<221> NAME/KEY: misc_feature
<222> LOCATION: (1)..(29)
<223> OTHER INFORMATION: FR1 of Heavy Chain(AF471493)

<400> SEQUENCE: 125

Glu Val Gln Leu Val Glu Ser Gly Gly Gly Leu Val Lys Pro Gly Gly
1               5                   10                  15

Tyr Leu Arg Leu Ser Cys Ala Ala Ser Gly Phe Thr Phe
            20                  25

<210> SEQ ID NO 126
<211> LENGTH: 14
<212> TYPE: PRT
<213> ORGANISM: Homo sapiens
<220> FEATURE:
<221> NAME/KEY: misc_feature
<222> LOCATION: (1)..(14)
<223> OTHER INFORMATION: FR2 of Heavy Chain(AF471493)

<400> SEQUENCE: 126

Trp Val Arg Gln Ala Pro Gly Lys Gly Leu Asp Trp Val Ala
1               5                   10

<210> SEQ ID NO 127
<211> LENGTH: 32
<212> TYPE: PRT
<213> ORGANISM: Homo sapiens
<220> FEATURE:
<221> NAME/KEY: misc_feature
<222> LOCATION: (1)..(32)
<223> OTHER INFORMATION: FR3 of Heavy Chain(AF471493)

<400> SEQUENCE: 127

Arg Phe Thr Ile Ser Arg Asp Asn Ala Lys Asn Ser Leu Tyr Leu Gln
1               5                   10                  15

Met Asn Ser Leu Thr Asp Asp Thr Ala Val Tyr Phe Cys Ala Arg
            20                  25                  30

<210> SEQ ID NO 128
<211> LENGTH: 11
<212> TYPE: PRT
<213> ORGANISM: Homo sapiens
<220> FEATURE:
<221> NAME/KEY: misc_feature
<222> LOCATION: (1)..(11)
<223> OTHER INFORMATION: FR4 of Heavy Chain(AF471493)

<400> SEQUENCE: 128

Trp Gly Gln Gly Thr Leu Val Thr Val Ser Ser
1               5                   10

<210> SEQ ID NO 129
<211> LENGTH: 107
<212> TYPE: PRT
<213> ORGANISM: Homo sapiens
<220> FEATURE:
<221> NAME/KEY: misc_feature
<222> LOCATION: (1)..(107)
<223> OTHER INFORMATION: Variable Region of Light Chain(X70463?j

<400> SEQUENCE: 129

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Gly Ser Phe
            20                  25                  30

Leu His Trp Tyr Gln Gln Lys Pro Gly Lys Pro Lys Leu Leu Ile
        35                  40                  45

Ser Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Ser Thr Leu Tyr
                85                  90                  95

Thr Phe Gly Gln Gly Thr Lys Leu Glu Ile Lys
            100                 105

<210> SEQ ID NO 130
<211> LENGTH: 23
<212> TYPE: PRT
<213> ORGANISM: Homo sapiens
<220> FEATURE:
<221> NAME/KEY: misc_feature
<222> LOCATION: (1)..(23)
<223> OTHER INFORMATION: FR1 of Light Chain(X70463)

<400> SEQUENCE: 130

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 131
<211> LENGTH: 15
<212> TYPE: PRT
<213> ORGANISM: Homo sapiens
<220> FEATURE:
<221> NAME/KEY: misc_feature
<222> LOCATION: (1)..(15)
<223> OTHER INFORMATION: FR2 of Light Chain(X70463)

<400> SEQUENCE: 131

Trp Tyr Gln Gln Lys Pro Gly Lys Gly Pro Lys Leu Leu Ile Ser
1               5                   10                  15

<210> SEQ ID NO 132
<211> LENGTH: 32
<212> TYPE: PRT
<213> ORGANISM: Homo sapiens
<220> FEATURE:
<221> NAME/KEY: misc_feature
<222> LOCATION: (1)..(32)
<223> OTHER INFORMATION: FR3 of Light Chain(X70463)

<400> SEQUENCE: 132

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 133

```
<211> LENGTH: 10
<212> TYPE: PRT
<213> ORGANISM: Homo sapiens
<220> FEATURE:
<221> NAME/KEY: misc_feature
<222> LOCATION: (1)..(10)
<223> OTHER INFORMATION: FR4 of Light Chain(X70463)

<400> SEQUENCE: 133

Phe Gly Gln Gly Thr Lys Leu Glu Ile Lys
1               5                   10

<210> SEQ ID NO 134
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 134
atataaagct taccatggaa tggagctggg                                    30

<210> SEQ ID NO 135
<211> LENGTH: 32
<212> TYPE: DNA
<213> ORGANISM: Artificial Sequence
<220> FEATURE:
<223> OTHER INFORMATION: Artificially Synthesized Primer Sequence

<400> SEQUENCE: 135
ccagctgcac ctcagaatgc acgcctgtgg tc                                 32

<210> SEQ ID NO 136
<211> LENGTH: 32
<212> TYPE: DNA
<213> ORGANISM: Artificial Sequence
<220> FEATURE:
<223> OTHER INFORMATION: Artificially Synthesized Primer Sequence

<400> SEQUENCE: 136
ccagccgcac ctcagaatgc acgcctgtgg tc                                 32

<210> SEQ ID NO 137
<211> LENGTH: 32
<212> TYPE: DNA
<213> ORGANISM: Artificial Sequence
<220> FEATURE:
<223> OTHER INFORMATION: Artificially Synthesized Primer Sequence

<400> SEQUENCE: 137
ccagcatcac ttcagaatgc acgcctgtgg tc                                 32

<210> SEQ ID NO 138
<211> LENGTH: 31
<212> TYPE: DNA
<213> ORGANISM: Artificial Sequence
<220> FEATURE:
<223> OTHER INFORMATION: Artificially Synthesized Primer Sequence

<400> SEQUENCE: 138
cgtgcattct gaggtgcagc tggtggagtc g                                  31

<210> SEQ ID NO 139
<211> LENGTH: 24
<212> TYPE: DNA
<213> ORGANISM: Artificial Sequence
<220> FEATURE:
```

<210> SEQ ID NO 139
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 139
atatactcga gacggtgacc aggg                                           24

<210> SEQ ID NO 140
<211> LENGTH: 31
<212> TYPE: DNA
<213> ORGANISM: Artificial Sequence
<220> FEATURE:
<223> OTHER INFORMATION: Artificially Synthesized Primer Sequence

<400> SEQUENCE: 140
cgtgcattct gaggtgcggc tggtggagtc g                                   31

<210> SEQ ID NO 141
<211> LENGTH: 33
<212> TYPE: DNA
<213> ORGANISM: Artificial Sequence
<220> FEATURE:
<223> OTHER INFORMATION: Artificially Synthesized Primer Sequence

<400> SEQUENCE: 141
cgtgcattct gaagtgatgc tggtggagtc tgg                                 33

<210> SEQ ID NO 142
<211> LENGTH: 24
<212> TYPE: DNA
<213> ORGANISM: Artificial Sequence
<220> FEATURE:
<223> OTHER INFORMATION: Artificially Synthesized Primer Sequence

<400> SEQUENCE: 142
atatactcga gacggtgact gagg                                           24

<210> SEQ ID NO 143
<211> LENGTH: 30
<212> TYPE: DNA
<213> ORGANISM: Artificial Sequence
<220> FEATURE:
<223> OTHER INFORMATION: Artificially Synthesized Primer Sequence

<400> SEQUENCE: 143
cagttgtttc acagcgggcg tctgtcagcc                                     30

<210> SEQ ID NO 144
<211> LENGTH: 27
<212> TYPE: DNA
<213> ORGANISM: Artificial Sequence
<220> FEATURE:
<223> OTHER INFORMATION: Artificially Synthesized Primer Sequence

<400> SEQUENCE: 144
acgcccgctg tgaaacaact gtgaccc                                        27

<210> SEQ ID NO 145
<211> LENGTH: 32
<212> TYPE: DNA
<213> ORGANISM: Artificial Sequence
<220> FEATURE:
<223> OTHER INFORMATION: Artificially Synthesized Primer Sequence

<400> SEQUENCE: 145
atatacgtac gtttgatccc cagcttggtt cc                                  32

MONOCLONAL ANTIBODY AGAINST HUMAN MIDKINE

CROSS REFERENCE TO RELATED APPLICATIONS

This is a National Stage of International Application No. PCT/JP2013/070642 filed Jul. 30, 2013, claiming priority based on Japanese Patent Application No. 2012-168637 filed Jul. 30, 2012, the contents of all of which are incorporated herein by reference in their entirety.

TECHNICAL FIELD

The present invention relates to a monoclonal antibody against human midkine, an anticancer drug containing the antibody, and an agent containing the antibody and intended for detecting or purifying midkine.

BACKGROUND ART

Midkine (MK) is a heparin binding growth factor of about 13 kDa rich in basic amino acids and cysteine which was discovered in 1988 by Kadomatsu et al. as a product of a gene expressed temporarily during the differentiation induction process of embryonal tumor cells by retinoic acid (NPLs 1 and 2).

Midkine is widely present in vertebrates, and is reported in humans, rats, mice, rabbits, cattle, fowls, *xenopus* and zebra fish. Its conservation is high and, for example, human midkine and mouse midkine have an amino acid homology of 87% in the entire molecule (NPL 3).

Activities such as heparin-binding capacity, neurite outgrowth, and neuronal migration are borne by a half molecule on the C-terminal side including a C-domain (NPL 4). The C-domain of human midkine and that of mouse midkine have an amino acid homology of 93% (40/43).

Midkine forms an independent family composed of pleiotrophin (PTN) as the only constituent. Pleiotrophin is a polypeptide of about 18 kDa, has an amino acid homology of about 45% to midkine, and promotes the elongation and growth of neurites, promotes transformation of cells, and promotes neovascularization.

Midkine is characterized by being expressed on the epithelium side of tissue where epithelial-stromal interaction occurs in the embryonal period (NPL 5). Its expression peaks in the middle of the embryonal period, then gradually decreases, is low at birth, and minimizes in an adult. However, strong expression is induced during the process of carcinogenesis, inflammation, or repair.

Midkine is known to have various biological functions. Broadly, midkine is important in three fields, cancer, inflammation, and nerve.

Midkine is considered to promote the survival and migration of cancer cells, trigger neovascularization, and assist in the progression of cancer. The manner of midkine expression in human cancer is characterized in that its expression is accelerated at an incidence exceeding 70%, regardless of the type of cancer. This is confirmed in a variety of cancers including esophageal carcinoma, thyroid carcinoma, bladder cancer, stomach cancer, pancreatic cancer, liver cancer, pulmonary cancer, breast cancer, neuroblastoma, glioblastoma, uterine cancer, ovarian cancer, and Wilms tumor (for example, NPLs 6 to 10).

Neuroblastoma is one of neuroendocrine tumors. It is extracranial solid cancer with the highest incidence in childhood. It is the fourth most frequent childhood malignant tumor following leukemia, central nervous system tumor, and lymphoma. Neuroblastoma is one of the three major causes of cancer deaths in children, and is the greatest cause of cancer deaths in infants. In the United States, about 650 new cases of neuroblastoma occur in a year. Approximately 50% of the neuroblastoma cases occur in children of less than 2 years of age. As a characteristic of neuroblastoma with a poor prognosis, N-myc gene is known to proliferate (NPLs 11 to 13).

There is a correlation between a neuroblastoma prognosticator, such as N-myc gene proliferation, and the blood midkine level (NPL 14). Furthermore, blood midkine can serve, alone, as a prognostic factor for neuroblastoma (NPL 15).

Midkine has the function of promoting inflammation. This is based mainly on findings obtained from the analysis of midkine knockout mice (Mdk−/−). In the knockout mouse, for example, the formation of a neointima at the time of injury to the blood vessel and the occurrence of nephritis associated with ischemic injury are alleviated. The condition of rheumatism models or postoperative adhesion is also relieved greatly. Moreover, midkine is known to promote the migration of inflammatory cells (chemotaxis), such as macrophages and neutrophils, or cause the differentiation of osteoclasts. Based on such findings, midkine is presumed to be involved in inflammatory diseases such as arthritis, autoimmune disease, articular rheumatism (rheumatoid arthritis (RA), osteoarthritis (OA)), multiple sclerosis, postoperative adhesion, inflammatory colitis, psoriasis, lupus, asthma, and neutrophil dysfunction (PTL 1, 2, 3).

Since midkine has intimal thickening action, moreover, it partakes in vascular obstructive diseases such as restenosis after revascularization, coronary vascular obstructive disease, cerebrovascular obstructive disease, renovascular obstructive disease, peripheral vessel obstructive disease, arteriosclerosis, and cerebral infarction (PTL 1).

An example of the function of midkine in the nerve is to assist in the survival of neurocytes and promote the outgrowth of neurites (NPLs 16, 17). For example, when coated with midkine in a lattice form on a culture dish, nerve cells survive in a lattice pattern along the midkine, and extend neurites. Also, midkine is temporarily induced around a lesion in the event of cerebral ischemia (NPL 18), and it is one of cytokines whose expression is induced most after injury in a rat spinal injury model. Midkine induced in this manner is assumed to prevent neuronal death.

The tissue protecting action of midkine during infarction is the same in the heart. On the occasion of acute myocardial infarction, midkine is expressed and induced around the infarct. In a midkine knockout mouse, enlargement of the infarct is observed compared with a wild type mouse, and when in infarction, direct injection of midkine protein into the myocardium preferentially shrinks the infarct and improves cardiac function (NPL 19). Such a protective effect is presumed to owe much to the anti-apoptotic activity of midkine.

Midkine is composed of an N-terminal side fragment (hereinafter, "N-fragment") comprising amino acids at the 1- to 52-positions, a C-terminal side fragment (hereinafter, "C-fragment") comprising amino acids at the 62- to 121-positions, and a loop region binding them together (amino acids at the 53- to 61-positions), and its stereostructure is analyzed by NMR (NPL 16). The N-fragment and the C-fragment are constituted, respectively, by a portion having a stereostructure comprising mainly three inverse β-sheets (hereinafter, "domain"), and a portion located outside the domain and having no particular stereostructure (hereinafter, "tail"). The N-fragment is composed of an N-domain comprising amino acids at the 15- to 52-positions and an N-tail comprising amino acids at the 1- to 14-positions, whereas the C-fragment is composed of a C-domain comprising amino acids at the 62- to 104-positions and a C-tail comprising amino acids at the 105- to 121-positions. On the surface of the C-domain, basic amino acids form two clusters. They are a cluster comprising lysine at the 79-position, arginine at the 81-position, and lysine at the 102-position (cluster I), and a cluster comprising lysine at the 86-position, lysine at the 87-position, and arginine at the 89-position (cluster II) (NPL 20). These clusters take part in the heparin-binding capacity of midkine (NPLs 20, 21).

Pharmaceuticals containing midkine inhibitors are disclosed in a plurality of patent gazettes (PTLs 4, 5, 6, 7). However, there are no midkine inhibitors marketed as pharmaceuticals.

CITATION LIST

Patent Literatures

[PTL 1] WO2000/10608
[PTL 2] WO2004/078210
[PTL 3] WO2004/085642
[PTL 4] WO99/03493
[PTL 5] JP-A-2002-85085
[PTL 6] JP-A-2007-297282
[PTL 7] JP-A-2007-137771

Non Patent Literatures

[NPL 1] Kadomatsu, K. et al. (1988) Biochem. Biophys. Res. Commun., 151, 1312-1318. [PMID:3355557]
[NPL 2] Tomomura, M. et al. (1990) J. Biol. Chem., 265, 10765-10770. [PMID: 2355021],
[NPL 3] Tsutsui, J. et al. (1993) Cancer Res. 53, 1281-1285. [PMID:8383007]
[NPL 4] Michikawa, M. et al. (1993) J. Neurosci. Res., 35, 530-539. [PMID:8377224]
[NPL 5] Kadomatsu, K. et al. (1990) J. Cell Biol. 110, 607-616. [PMID:1689730]
[NPL 6] Tsutsui, J. et al. (1993) Cancer Res. 53, 1281-1285. [PMID: 8383007]
[NPL 7] Garver, R. I. et al. (1993) Am. J. Respir. Cell Mol. Biol. 9, 463-466. [PMID:8217186]
[NPL 8] Aridome, K. et al. (1995) Jap. J. Cancer Res. 86, 655-661. [PMID:7559083]
[NPL 9] O'Brien, T. et al. (1996) Cancer Res. 56, 2515-2518. [PMID: 8653688]
[NPL 10] Muramatsu T. (2002) J Biochem 132, (3):359-371.
[NPL 11] Kohl N E et al. (1983) Cell 35, 359-67.
[NPL 12] Brodeur G M et al. (1984) Science (New York, N.Y.) 224, 1121-4.
[NPL 13] Seeger R C et al. (1985) The New England journal of medicine 313, 1111-6.
[NPL 14] Ikematsu, S. et al. (2003) Br. J. Cancer 88, 1522-1526. [PMID: 12771916]
[NPL 15] Ikematsu S et al. (October 2008) Cancer Science (10), 2070-2074.
[NPL 16] Muramatsu, H. et al. (1993) Dev. Biol. 159, 392-402. [PMID:8405666]
[NPL 17] Kaneda N. et al. (1996) J. Biochem., 119(6): 1150-1156.
[NPL 18] Yoshida, Y. et al. (1995) Dev. Brain Res. 85, 25-30. [PMID:7781164]
[NPL 19] Horiba, M. et al. (2006) Circulation. 114, 1713-1720. [PMID:17015789]
[NPL 20] Iwasaki, W. et al. (1997) EMBO J. 16, 6936-6946. [PMID: 9384573]
[NPL 21] Kojima, S. et al. (1995) Biochem. Biophys. Res. Commun., 206, 468-473.

SUMMARY OF INVENTION

Technical Problem

The present invention has been accomplished in the light of the above-described circumstances. It is an object of this invention to provide a monoclonal antibody having excellent reactivity with and high neutralizing activity against human midkine. It is another object of the invention to provide an anticancer drug containing such an antibody as an active principle. It is still another object of the invention to provide an agent for detecting or purifying midkine, the agent containing the antibody as an active ingredient.

Solution to Problem

In an attempt to attain the above objects, the present inventors prepared numerous monoclonal antibodies (mouse antibodies) against human midkine, evaluated their neutralizing activities against human midkine, and selected antibodies having excellent neutralizing activity. Using, as an index, reactivity with mutant peptides in which specific amino acids of human midkine have been substituted by other amino acids, they identified recognition sites for the selected antibodies on the human midkine. As a result, they found the antibodies having excellent neutralizing activity to recognize, in common, at least two amino acids among the amino acids located at position 69, position 79, position 81 and position 102 of human midkine. Of them, the antibodies exhibiting particularly high neutralizing activity were the antibodies recognizing all of the amino acids at the 69-, 79-, 81- and 102-positions of human midkine.

The present inventors also isolated the gene for FB54, the antibody shown to have the highest neutralizing activity, and prepared, based thereon, chimeric antibodies and humanized antibodies. They evaluated the reactivities of these antibodies with human midkine, and found these antibodies to have reactivity comparable to that of the original mouse antibodies. They further evaluated the humanized antibodies for antitumor activity with the use of a mouse xenograft, and found that these antibodies significantly inhibited the proliferation of tumor. In a control group without administration of the antibodies, all individuals died in about 90 days. In a group receiving administration of the humanized antibodies, as many as 30% of the individuals were alive even after 100 days. Thus, the life prolonging effect of the antibodies was also confirmed.

Furthermore, the present inventors prepared Fab antibodies having mutation introduced into the variable region of the mouse antibody or the humanized antibody for FB54, and evaluated their reactivities with human midkine and mouse midkine. As a result, they succeeded in acquiring a plurality of Fab antibodies increased in reactivity with these midkines as compared with the original mouse antibodies. They were also successful in converting the acquired Fab antibodies into IgGs to attain raised reactivity with and enhanced neutralizing activity against human midkine and mouse midkine.

The present inventors found that cancer could be treated effectively, and midkine could be detected or purified efficiently, by utilizing the characteristics of the acquired antibodies against midkine, such as excellent reactivity with and excellent neutralizing activity against midkine, and excellent activity of suppressing tumor proliferation. These findings have led them to accomplish the present invention.

That is, the present invention relates to a monoclonal antibody which recognizes at least two amino acids among amino acids at position 69, position 79, position 81 and position 102 of human midkine and which has neutralizing activity against human midkine; an anticancer drug containing the antibody as an active principle; and an agent for detecting or purifying midkine, the agent containing the antibody as an active ingredient. In detail, the present invention provides the following aspects of the invention:

[1] A monoclonal antibody which recognizes at least two amino acids among amino acids located at position 69, position 79, position 81 and position 102 of human midkine and which has neutralizing activity against human midkine.

[2] The antibody according to [1], which recognizes all amino acids among the amino acids located at position 69, position 79, position 81 and position 102 of human midkine.

[3] The antibody according to [1] or [2], which has an activity of suppressing proliferation of tumor.

[4] A monoclonal antibody having a feature described in one of following (a) to (e):
  (a) comprising
    a light chain variable region including complementarity-determining regions comprising amino acid sequences defined by SEQ ID NOs: 1 to 3, or complementarity-determining regions comprising amino acid sequences having one or more amino acids substituted, deleted, added and/or inserted in at least one of the amino acid sequences defined by SEQ ID NOs: 1 to 3; and
    a heavy chain variable region including complementarity-determining regions comprising amino acid sequences defined by SEQ ID NOs: 4 to 6, or complementarity-determining regions comprising amino acid sequences having one or more amino acids substituted, deleted, added and/or inserted in at least one of the amino acid sequences defined by SEQ ID NOs: 4 to 6;
  (b) comprising
    a light chain variable region including the amino acid sequence defined by SEQ ID NO: 7, or an amino acid sequence having one or more amino acids substituted, deleted, added and/or inserted at least anywhere in the amino acid sequence defined by SEQ ID NO: 7; and
    a heavy chain variable region including the amino acid sequence defined by SEQ ID NO: 8, or an amino acid sequence having one or more amino acids substituted, deleted, added and/or inserted at least anywhere in the amino acid sequence defined by SEQ ID NO: 8;
  (c) comprising
    a light chain variable region including the amino acid sequence defined by SEQ ID NO: 9, or an amino acid sequence having one or more amino acids substituted, deleted, added and/or inserted at least anywhere in the amino acid sequence defined by SEQ ID NO: 9; and
    a heavy chain variable region including the amino acid sequence defined by SEQ ID NO: 12, or an amino acid sequence having one or more amino acids substituted, deleted, added and/or inserted at least anywhere in the amino acid sequence defined by SEQ ID NO: 12;
  (d) comprising
    a light chain variable region including the amino acid sequence defined by SEQ ID NO: 10, or an amino acid sequence having one or more amino acids substituted, deleted, added and/or inserted at least anywhere in the amino acid sequence defined by SEQ ID NO: 10; and
    a heavy chain variable region including the amino acid sequence defined by SEQ ID NO: 12, or an amino acid sequence having one or more amino acids substituted, deleted, added and/or inserted at least anywhere in the amino acid sequence defined by SEQ ID NO: 12; and
  (e) comprising
    a light chain variable region including the amino acid sequence defined by SEQ ID NO: 11, or an amino acid sequence having one or more amino acids substituted, deleted, added and/or inserted at least anywhere in the amino acid sequence defined by SEQ ID NO: 11; and
    a heavy chain variable region including the amino acid sequence defined by SEQ ID NO: 12, or an amino acid sequence having one or more amino acids substituted, deleted, added and/or inserted at least anywhere in the amino acid sequence defined by SEQ ID NO: 12.

[5] The antibody according to [4], wherein the amino acid at position 4 of CDR1 of the complementarity-determining regions in the light chain variable region is isoleucine.

[6] A monoclonal antibody having a feature described in one of following (a) to (r):
  (a) comprising
    a light chain variable region including complementarity-determining regions comprising amino acid sequences defined by SEQ ID NOs: 13 to 15, and
    a heavy chain variable region including complementarity-determining regions comprising amino acid sequences defined by SEQ ID NOs: 16 to 18;
  (b) comprising
    a light chain variable region including complementarity-determining regions comprising amino acid sequences defined by SEQ ID NOs: 21 to 23, and
    a heavy chain variable region including complementarity-determining regions comprising amino acid sequences defined by SEQ ID NOs: 24 to 26;
  (c) comprising
    a light chain variable region including complementarity-determining regions comprising amino acid sequences defined by SEQ ID NOs: 29 to 31, and
    a heavy chain variable region including complementarity-determining regions comprising amino acid sequences defined by SEQ ID NOs: 32 to 34;
  (d) comprising
    a light chain variable region including complementarity-determining regions comprising amino acid sequences defined by SEQ ID NOs: 37 to 39, and
    a heavy chain variable region including complementarity-determining regions comprising amino acid sequences defined by SEQ ID NOs: 40 to 42;
  (e) comprising
    a light chain variable region including complementarity-determining regions comprising amino acid sequences defined by SEQ ID NOs: 45 to 47, and
    a heavy chain variable region including complementarity-determining regions comprising amino acid sequences defined by SEQ ID NOs: 48 to 50;
  (f) comprising
    a light chain variable region including complementarity-determining regions comprising amino acid sequences defined by SEQ ID NOs: 53 to 55, and
    a heavy chain variable region including complementarity-determining regions comprising amino acid sequences defined by SEQ ID NOs: 56 to 58;

(g) comprising
a light chain variable region including complementarity-determining regions comprising amino acid sequences defined by SEQ ID NOs: 61 to 63, and
a heavy chain variable region including complementarity-determining regions comprising amino acid sequences defined by SEQ ID NOs: 64 to 66;
(h) comprising
a light chain variable region including complementarity-determining regions comprising amino acid sequences defined by SEQ ID NOs: 69 to 71, and
a heavy chain variable region including complementarity-determining regions comprising amino acid sequences defined by SEQ ID NOs: 72 to 74;
(i) comprising
a light chain variable region including complementarity-determining regions comprising amino acid sequences defined by SEQ ID NOs: 77 to 79, and
a heavy chain variable region including complementarity-determining regions comprising amino acid sequences defined by SEQ ID NOs: 80 to 82;
(j) comprising
a light chain variable region including the amino acid sequence defined by SEQ ID NO: 19, and
a heavy chain variable region including the amino acid sequence defined by SEQ ID NO: 20;
(k) comprising
a light chain variable region including the amino acid sequence defined by SEQ ID NO: 27, and
a heavy chain variable region including the amino acid sequence defined by SEQ ID NO: 28;
(l) comprising
a light chain variable region including the amino acid sequence defined by SEQ ID NO: 35, and
a heavy chain variable region including the amino acid sequence defined by SEQ ID NO: 36;
(m) comprising
a light chain variable region including the amino acid sequence defined by SEQ ID NO: 43, and
a heavy chain variable region including the amino acid sequence defined by SEQ ID NO: 44;
(n) comprising
a light chain variable region including the amino acid sequence defined by SEQ ID NO: 51, and
a heavy chain variable region including the amino acid sequence defined by SEQ ID NO: 52;
(o) comprising
a light chain variable region including the amino acid sequence defined by SEQ ID NO: 59, and
a heavy chain variable region including the amino acid sequence defined by SEQ ID NO: 60;
(p) comprising
a light chain variable region including the amino acid sequence defined by SEQ ID NO: 67, and
a heavy chain variable region including the amino acid sequence defined by SEQ ID NO: 68;
(q) comprising
a light chain variable region including the amino acid sequence defined by SEQ ID NO: 75, and
a heavy chain variable region including the amino acid sequence defined by SEQ ID NO: 76; and
(r) comprising
a light chain variable region including the amino acid sequence defined by SEQ ID NO: 83, and
a heavy chain variable region including the amino acid sequence defined by SEQ ID NO: 84.

[7] A DNA encoding the monoclonal antibody according to any one of [1] to [6].
[8] A cell or an organism which produces the monoclonal antibody according to any one of [1] to [6], or which contains the DNA according to [7].
[9] A monoclonal antibody which recognizes at least two amino acids among amino acids located at position 69, position 79, position 81 and position 102 of human midkine.
[10] An anticancer drug containing the monoclonal antibody according to any one of [1] to [6] as an active principle.
[11] A method for treating or preventing cancer, comprising a step of administering the monoclonal antibody according to any one of [1] to [6] to a patient.
[12] An agent for detecting or purifying midkine, the agent containing the monoclonal antibody according to any one of [1] to [6] as an active ingredient.

Advantageous Effects of Invention

The present invention has provided a monoclonal antibody which recognizes at least two amino acids among amino acids at position 69, position 79, position 81 and position 102 of human midkine, and which has excellent reactivity with and excellent neutralizing activity against human midkine. In particular, the antibody recognizing all of the amino acids at the 69-, 79-, 81- and 102-positions of human midkine had the highest neutralizing activity. Moreover, the antibody having excellent neutralizing activity was observed to exhibit the activity of suppressing the proliferation of tumor. Hence, the use of the antibody according to the present invention permits effective treatment of cancer. Furthermore, the antibody of the present invention, because of its high reactivity with midkine, can be applied as an agent for detecting or purifying midkine.

DESCRIPTION OF EMBODIMENTS

The present invention provides a monoclonal antibody which recognizes at least two amino acids among amino acids at position 69, position 79, position 81 and position 102 of human midkine and which has neutralizing activity against human midkine.

The term "midkine" in the present invention refers to a protein, also called neurite growth promoting factor 2 (NEGF2), which is rich in basic amino acids and cysteine and has a molecular weight of about 13 KDa. Midkine has been shown to promote the survival and migration of cells and partake in the progression of cancer, the occurrence of inflammatory disease, and the preservation and repair of injured tissue. The substance "human midkine", to which the antibody of the present invention binds, refers to midkine derived from humans. Typically, human midkine is a protein comprising lysine at the 23-position to aspartic acid at the 143-position in a protein specified as RefSeq ID:NP_001012333 (a protein encoded by DNA specified as RefSeq ID:NM_001012333). The protein specified as RefSeq ID:NP_001012333 is a precursor including a signal peptide, and the "protein comprising lysine at the 23-position to aspartic acid at the 143-position" is a matured secretory human midkine deprived of the signal peptide. Normally, in human midkine, the 23-position lysine is defined as the 1-position amino acid, and thus such a definition is also given herein. That is, the "amino acids at position 69, position 79, position 81 and position 102 of human midkine" in the present invention correspond to 91-position tryptophan, 101-position lysine, 103-position arginine and 124-position lysine, respectively, in the protein (precursor) specified as RefSeq ID:NP_001012333.

Figure 6:
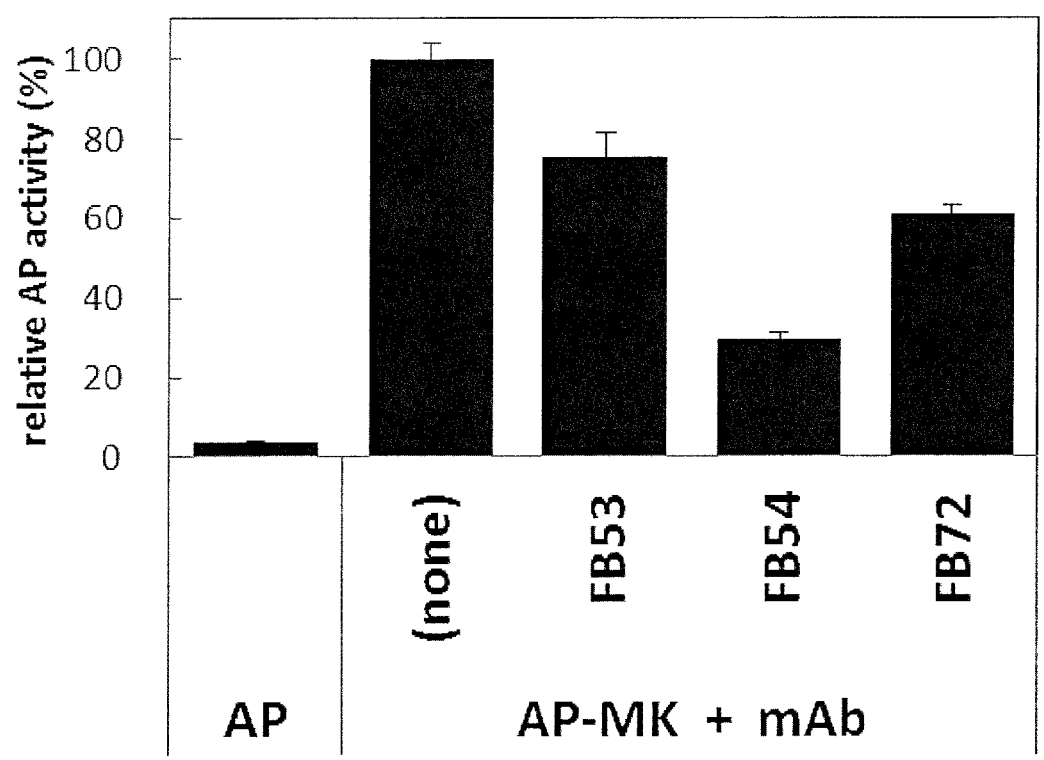
FIG. 6 is a graph showing the results of analyses of the neutralizing activity of the acquired anti-midkine monoclonal antibodies (FB53, FB54 and FB72) by evaluating the degree of inhibition of binding between alkaline phosphatase (AP)-labeled midkine (AP-MK) and the receptor on the cell surface. "AP" indicates a relative AP activity value (%) in an extract of cells incorporating only AP. "AP-MK+mAb" represents a relative AP activity value (%) in an extract of cells incorporating AP-MK and the anti-midkine monoclonal antibody. The term "none" denotes a relative AP activity value (%) in an extract of cells incorporating only AP-MK.
Figure 7:
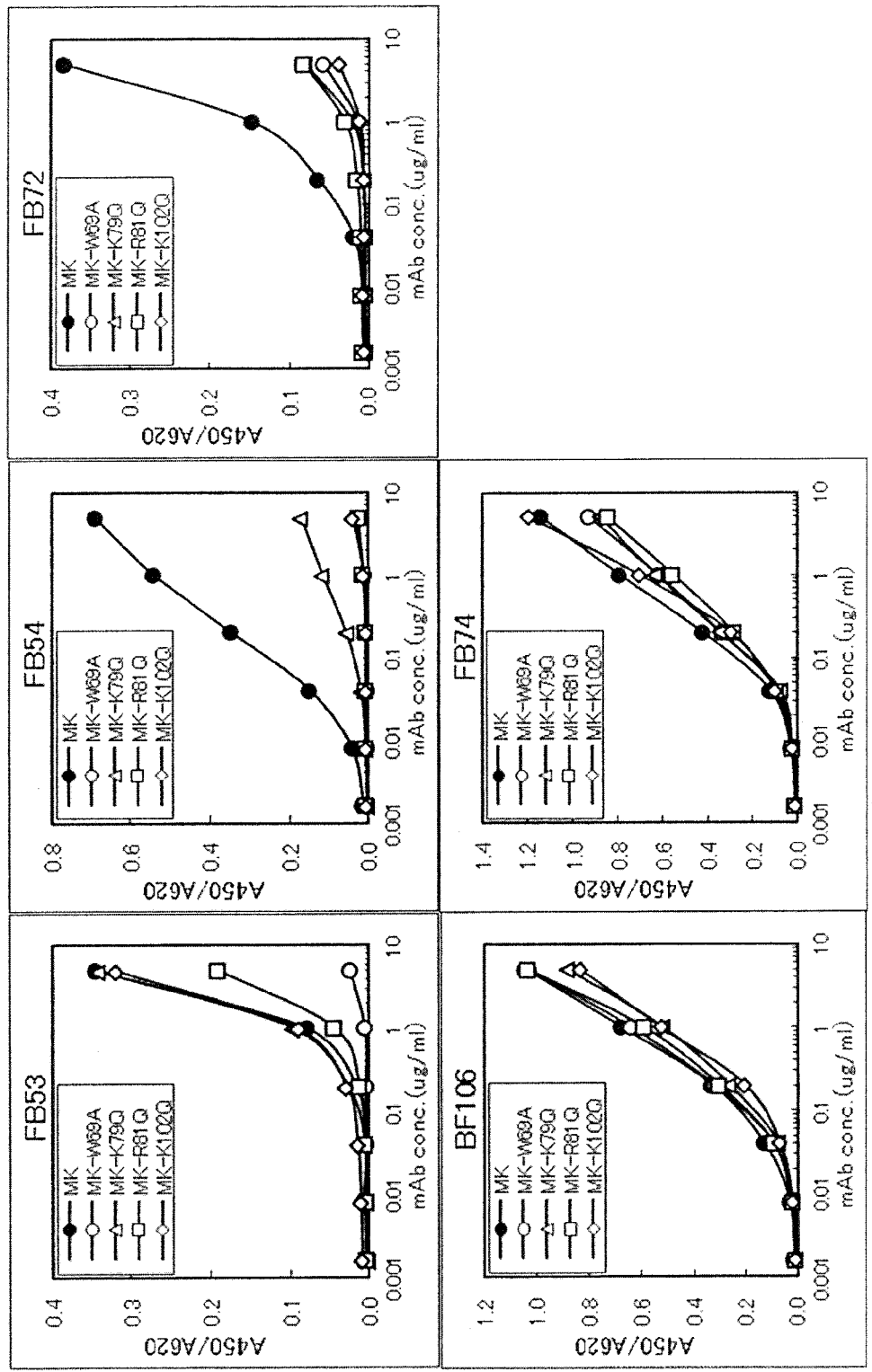
FIG. 7 is graphs showing the results of analyses by ELISA of the reactivities of the acquired anti-midkine monoclonal antibodies (FB53, FB54, FB72, BF106 and FB74) with mutant midkine recombinant proteins (MK-W69A, MK-K79Q, MK-R81Q and MK-K102Q). In these graphs, "MK" signifies the reactivity of each antibody with a wild type midkine recombinant protein.
Figure 21:
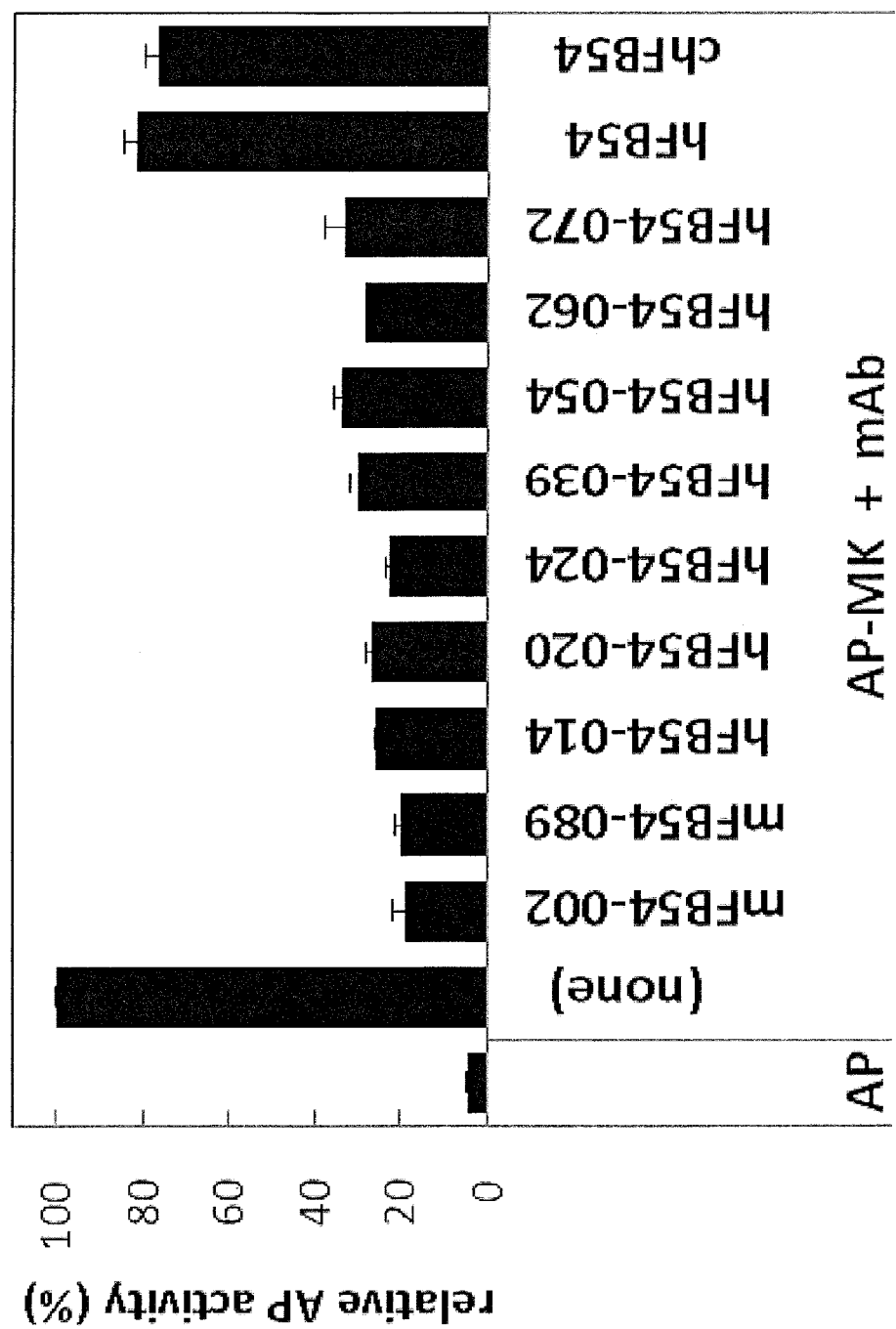
FIG. 21 is a graph showing the results of analyses of the neutralizing activities of the affinity-improved antibodies of mFB54, hFB54, the affinity-improved antibodies of hFB54, and chFB54 by evaluating the degree of inhibition of binding between AP-MK and the receptor on the cell surface. The symbol "AP" indicates a relative AP activity value (%) in an extract of cells incorporating only AP. The symbol "AP-MK+mAb" represents a relative AP activity value (%) in an extract of cells incorporating AP-MK and the anti-midkine monoclonal antibody. The designation "none" denotes a relative AP activity value (%) in an extract of cells incorporating only AP-MK.

The antibody of the present invention recognizes at least two amino acids among the amino acids at position 69, position 79, position 81 and position 102 of human midkine, and has neutralizing activity against human midkine. For example, FB53 described in the Examples herein recognizes the two amino acids at position 69 and position 81 of human midkine, and FB54 and FB72 recognize all of the amino acids at position 69, position 79, position 81 and position 102 of human midkine (FIG. 7). Such recognition specificity in the antibodies was found to correlate with the neutralizing activity against human midkine. In particular, FB54 and FB72 recognizing all of the amino acids at positions 69, 79, 81 and 102 of human midkine, and the amino acid sequence mutants of FB54 (the antibodies improved in reactivity with midkine) had excellent neutralizing activities (FIGS. 6, 21). Hence, a preferred embodiment of the antibody of the present invention is an antibody recognizing all of the amino acids at positions 69, 79, 81 and 102 of human midkine.

The recognition by the antibody of particular amino acids on human midkine can be evaluated, for example, by using, as an index, a decrease in reactivity with a peptide having the particular amino acids mutated, as described in Example 15. The "neutralizing activity against human midkine", which the antibody has, can be evaluated as the activity of the test antibody in inhibiting the binding of labeled midkine to the midkine receptor, as described in Examples 12 and 24. The activity of the present invention is an antibody which, as compared with a control (no antibody), lowers the binding of midkine, preferably to 80% or less, more preferably to 70% or less, still more preferably to 60% or less, still more preferably to 50% or less, still more preferably to 40% or less, even more preferably to 30% or less, most preferably to 20% or less.

Figure 11:
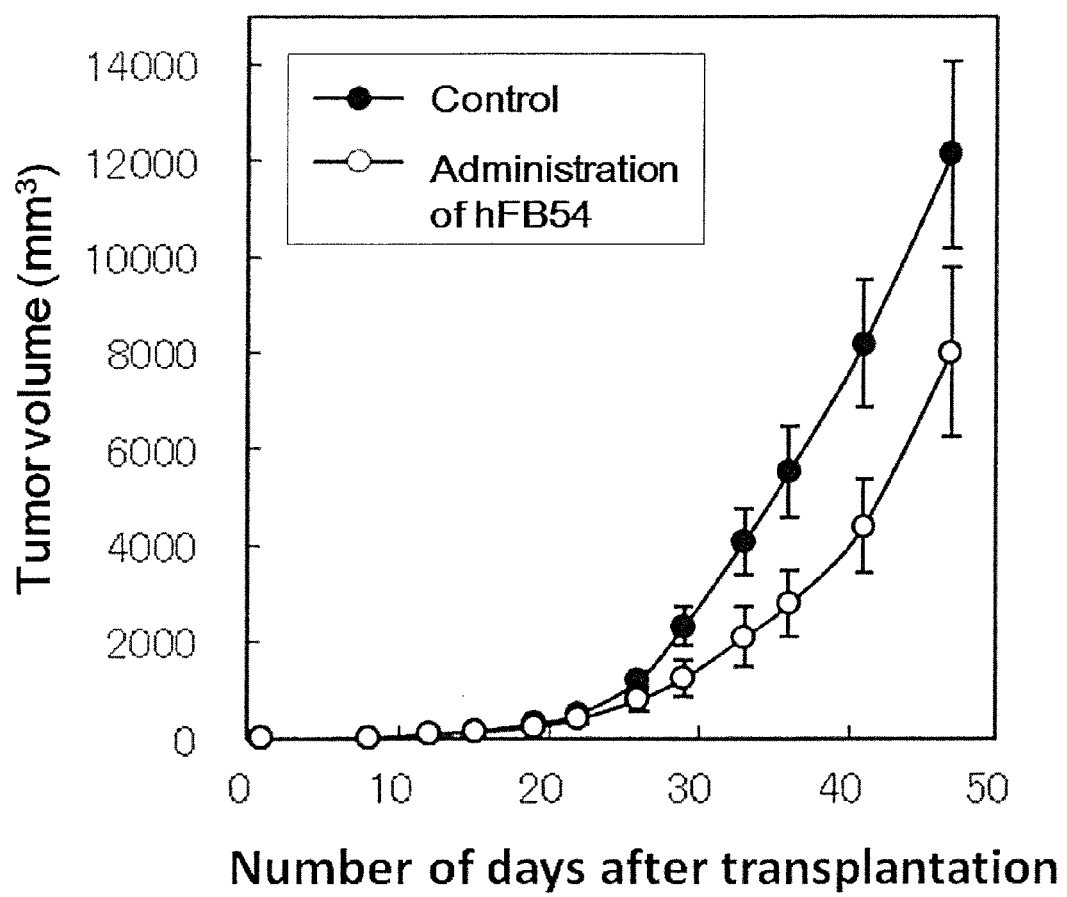
FIG. 11 is a graph showing the results of evaluation of the antitumor activity of hFB54 by use of a mouse xenograft transplanted with a human neuroblastoma.
Figure 12:
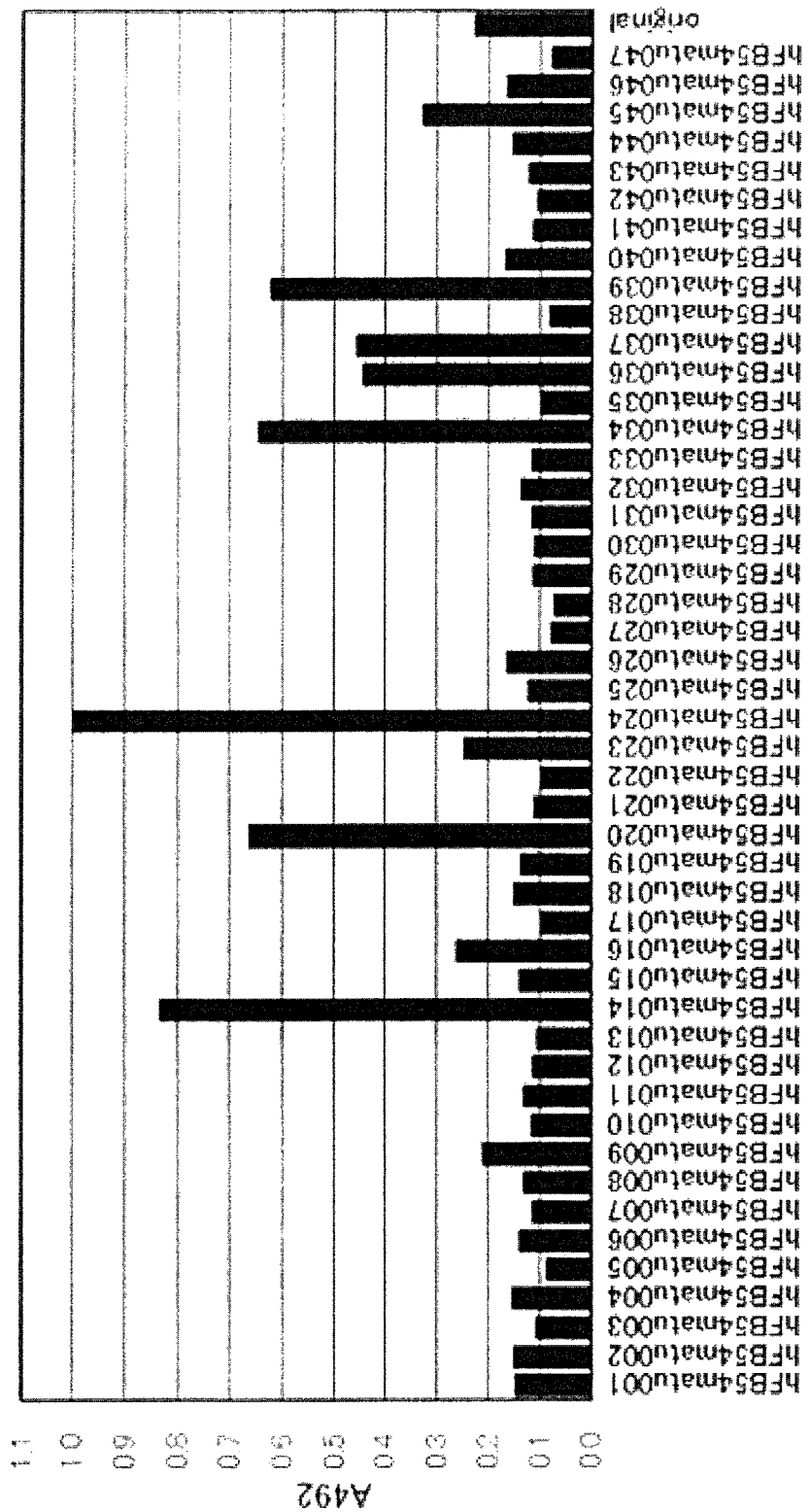
FIG. 12 is a graph showing the results of analyses by ELISA of the reactivities, with recombinant human midkine (MKver10), of Fab antibodies having random mutations introduced into the antibody variable region of hFB54 (i.e., hFB54matu001 to 047). The term "original" represents the reactivity of hFB54 with recombinant human midkine.
Figure 13:
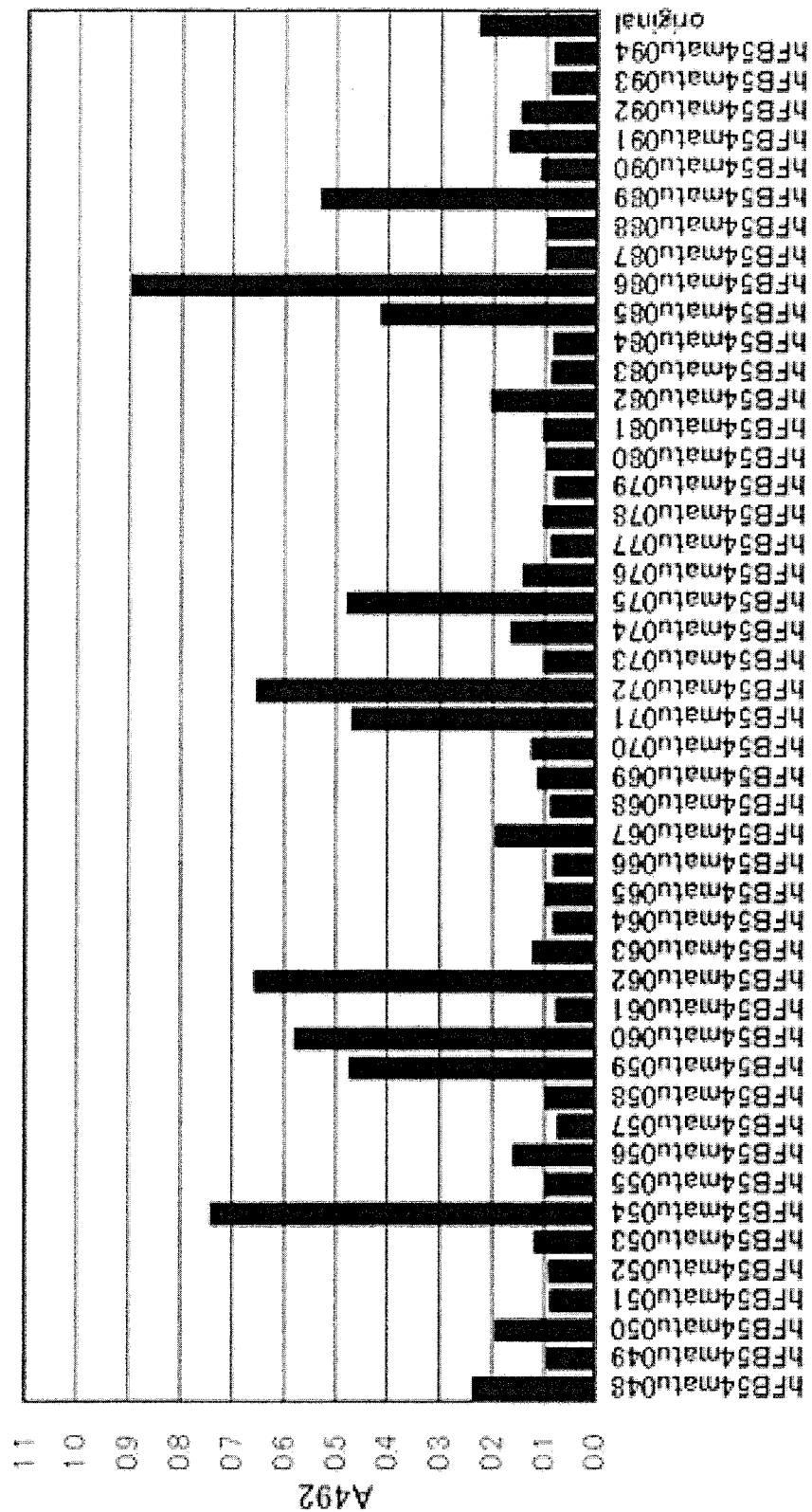
FIG. 13 is a graph showing the results of analyses by ELISA of the reactivities, with recombinant human midkine (MKver10), of Fab antibodies having random mutations introduced into the antibody variable region of hFB54 (i.e., hFB54matu048 to 094). The term "original" represents the reactivity of hFB54 with recombinant human midkine.
Figure 14:
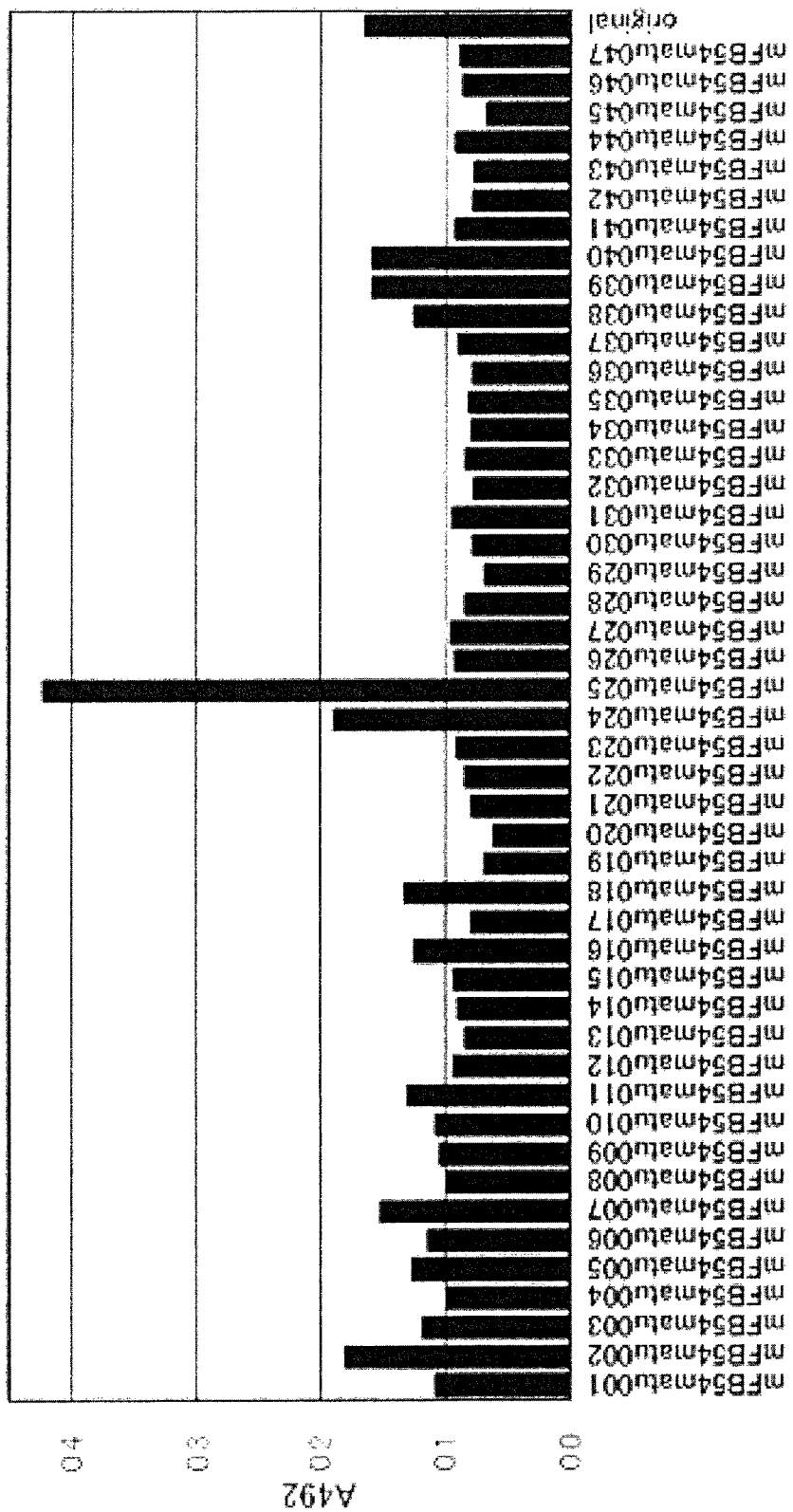
FIG. 14 is a graph showing the results of analyses by ELISA of the reactivities, with mouse midkine (mMK), of Fab antibodies having random mutations introduced into the antibody variable region of mFB54 (i.e., mFB54matu001 to 047). The designation "original" represents the reactivity of mFB54 with mouse midkine.
Figure 15:
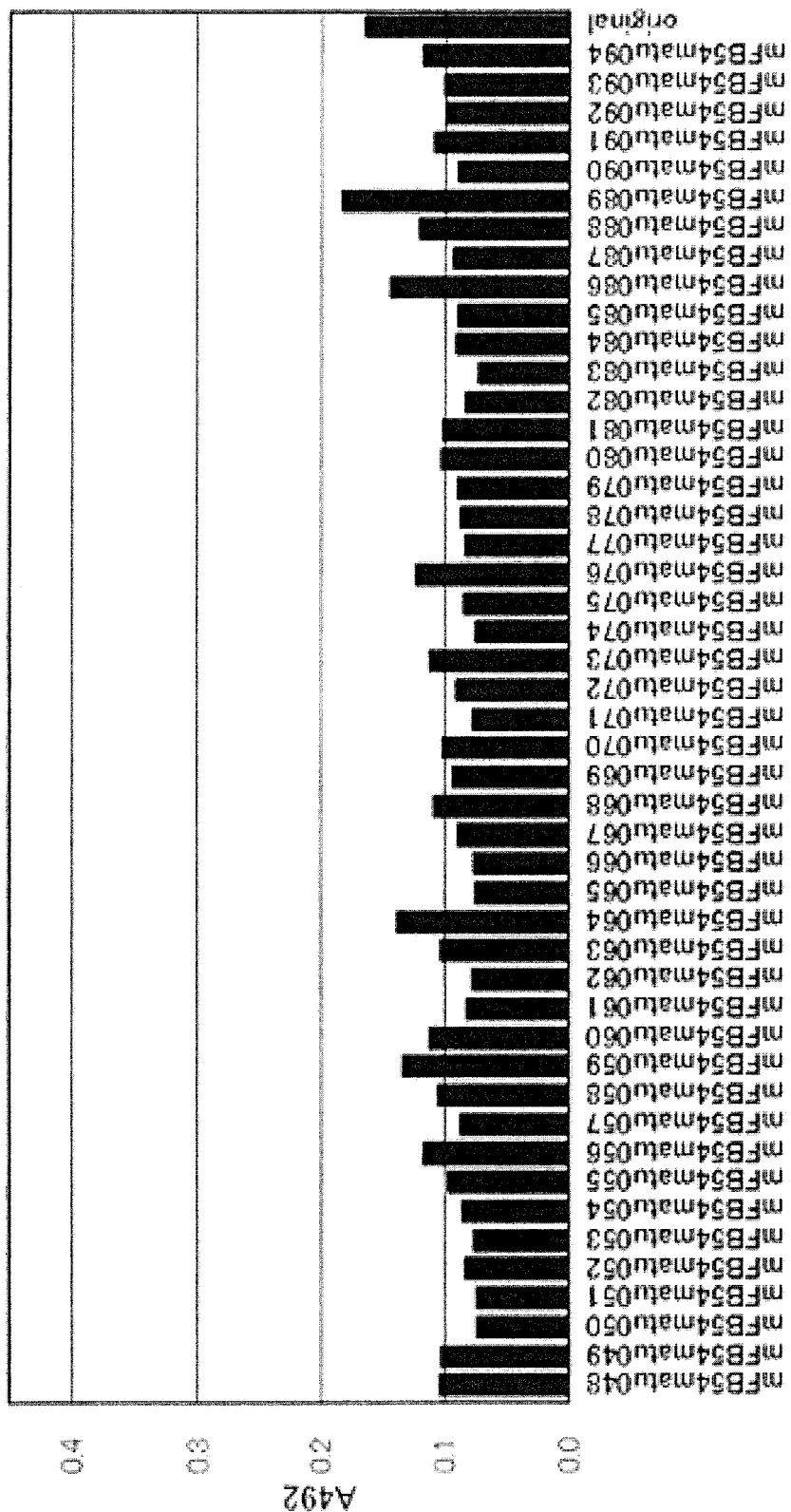
FIG. 15 is a graph showing the results of analyses by ELISA of the reactivities, with mouse midkine (mMK), of Fab antibodies having random mutations introduced into the antibody variable region of mFB54 (i.e., mFB54matu048 to 094). The designation "original" represents the reactivity of mFB54 with mouse midkine.

Another preferred embodiment of the antibody of the present invention is an antibody having tumor proliferation suppressing activity. The "tumor proliferation suppressing activity" of the antibody can be evaluated, for example, by measuring the volume of a tumor after administration of the test antibody in an experiment using a mouse xenograft, as described in Example 21. The antibody of the present invention is an antibody which decreases the tumor volume at 29 days or later after transplantation of tumor cells (for example, at 29, 33, 36 or 41 days) to preferably 80% or less, more preferably 75% or less, more preferably 70% or less, more preferably 65% or less, more preferably 60% or less, more preferably 55% or less, in comparison with a control (without antibody). For example, FB54 described in the present Examples had excellent activity of suppressing tumor proliferation (FIG. 11). Because of this tumor proliferation suppressing activity, the antibody of the present invention can also exhibit the effect of prolonging the life of an individual.

The antibody of the present invention is particularly preferably an antibody concurrently having a plurality of the above-mentioned activities.

Another preferred embodiment of the antibody of the present invention is an antibody comprising a light chain variable region including light chain CDR1 to CDR3 and a heavy chain variable region including heavy chain CDR1 to CDR3 of FB54 described in the present Examples, or amino acid sequence mutants thereof. That is, the inventive antibody is an antibody comprising a light chain variable region including complementarity-determining regions comprising amino acid sequences defined by SEQ ID NOs: 1 to 3, or complementarity-determining regions comprising amino acid sequences having one or more amino acids substituted, deleted, added and/or inserted in at least one of the above amino acid sequences; and a heavy chain variable region including complementarity-determining regions comprising amino acid sequences defined by SEQ ID NOs: 4 to 6, or complementarity-determining regions comprising amino acid sequences having one or more amino acids substituted, deleted, added and/or inserted in at least of the above amino acid sequences.

Figure 18:
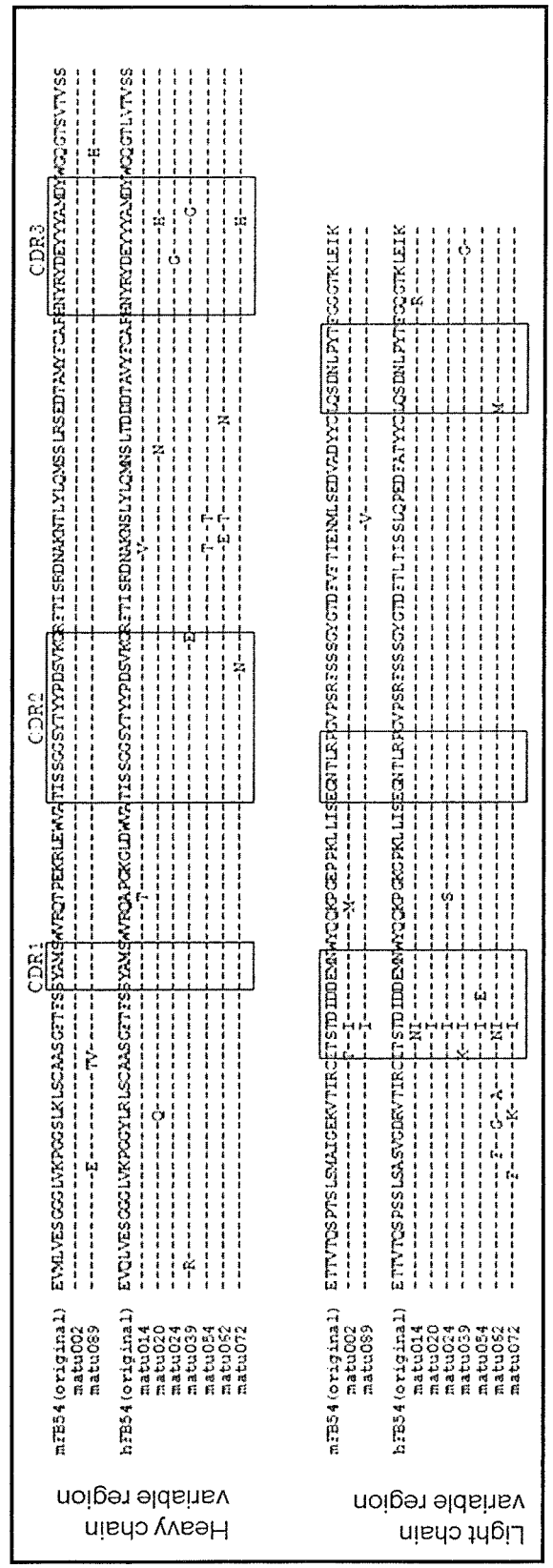
FIG. 18 is a graph showing the results of comparisons of the amino acid sequences of the heavy chain variable region and the light chain variable region between mFB54 and the affinity-improved antibodies of mFB54 (SEQ ID NOs: 7 and 8) (matu002 (SEQ ID NOs: 19 and 20), matu089 (SEQ ID NOs: 27 and 28)) and between hFB54 (SEQ ID NOs: 11 and 12) and the affinity-improved antibodies of hFB54 (matu014 (SEQ ID NOs: 35 and 36), matu020 (SEQ ID NOs: 43 and 44), matu024 (SEQ ID NOs: 51 and 52), matu039 (SEQ ID NOs: 59 and 60), matu054 (SEQ ID NOs: 67 and 68), matu062 (SEQ ID NOs: 75 and 76), and matu072 (SEQ ID NOs: 83 and 84)).

The preferred amino acid sequence mutants of FB54 are antibodies in which the amino acid at the 4-position of CDR1 of the light chain has been mutated from "T" into "I", namely, the antibodies in which the amino acid at the 4-position of CDR1 among the complementarity-determining regions in the light chain variable region is isoleucine. Such antibodies have in common excellent reactivity with human midkine and mouse midkine (FIG. 18). Concrete examples of such antibodies are antibodies having a feature described in one of (a) to (i) below.

<matu002>
(a) comprising
a light chain variable region including complementarity-determining regions comprising amino acid sequences defined by SEQ ID NOs: 13 to 15, and
a heavy chain variable region including complementarity-determining regions comprising amino acid sequences defined by SEQ ID NOs: 16 to 18.

<matu089>
(b) comprising
a light chain variable region including complementarity-determining regions comprising amino acid sequences defined by SEQ ID NOs: 21 to 23, and
a heavy chain variable region including complementarity-determining regions comprising amino acid sequences defined by SEQ ID NOs: 24 to 26.

<matu014>
(c) comprising
a light chain variable region including complementarity-determining regions comprising amino acid sequences defined by SEQ ID NOs: 29 to 31, and
a heavy chain variable region including complementarity-determining regions comprising amino acid sequences defined by SEQ ID NOs: 32 to 34.

<matu020>
(d) comprising
a light chain variable region including complementarity-determining regions comprising amino acid sequences defined by SEQ ID NOs: 37 to 39, and
a heavy chain variable region including complementarity-determining regions comprising amino acid sequences defined by SEQ ID NOs: 40 to 42.

<matu024>
(e) comprising
a light chain variable region including complementarity-determining regions comprising amino acid sequences defined by SEQ ID NOs: 45 to 47, and
a heavy chain variable region including complementarity-determining regions comprising amino acid sequences defined by SEQ ID NOs: 48 to 50.

<matu039>
(f) comprising
a light chain variable region including complementarity-determining regions comprising amino acid sequences defined by SEQ ID NOs: 53 to 55, and
a heavy chain variable region including complementarity-determining regions comprising amino acid sequences defined by SEQ ID NOs: 56 to 58.

<matu054>
(g) comprising
a light chain variable region including complementarity-determining regions comprising amino acid sequences defined by SEQ ID NOs: 61 to 63, and a heavy chain variable region including complementarity-determining regions comprising amino acid sequences defined by SEQ ID NOs: 64 to 66.

<matu062>

(h) comprising a light chain variable region including complementarity-determining regions comprising amino acid sequences defined by SEQ ID NOs: 69 to 71, and a heavy chain variable region including complementarity-determining regions comprising amino acid sequences defined by SEQ ID NOs: 72 to 74.

<matu072>

(i) comprising a light chain variable region including complementarity-determining regions comprising amino acid sequences defined by SEQ ID NOs: 77 to 79, and a heavy chain variable region including complementarity-determining regions comprising amino acid sequences defined by SEQ ID NOs: 80 to 82.

Another preferred embodiment of the antibody of the present invention is an antibody comprising a light chain variable region and a heavy chain variable region of FB54 (mouse antibody), or amino acid sequence mutants thereof. That is, the inventive antibody is an antibody comprising a light chain variable region including the amino acid sequence defined by SEQ ID NO: 7, or the amino acid sequence having one or more amino acids substituted, deleted, added and/or inserted in at least anywhere in the above amino acid sequence; and a heavy chain variable region including the amino acid sequence defined by SEQ ID NO: 8, or an amino acid sequence having one or more amino acids substituted, deleted, added and/or inserted in at least anywhere in the above amino acid sequence.

Another preferred embodiment of the antibody of the present invention is FB54 (humanized antibody), or an amino acid sequence mutant thereof. That is, the inventive antibody is a monoclonal antibody comprising a light chain variable region described in one of the following (a) to (c):

(a) a light chain variable region including the amino acid sequence defined by SEQ ID NO: 9, or the amino acid sequence having one or more amino acids substituted, deleted, added and/or inserted in at least anywhere in the above amino acid sequence, (b) a light chain variable region including the amino acid sequence defined by SEQ ID NO: 10, or an amino acid sequence having one or more amino acids substituted, deleted, added and/or inserted in at least anywhere in the above amino acid sequence, (c) a light chain variable region including the amino acid sequence defined by SEQ ID NO: 11, or the amino acid sequence having one or more amino acids substituted, deleted, added and/or inserted in at least anywhere in the above amino acid sequence;

and a heavy chain variable region including the amino acid sequence defined by SEQ ID NO: 12, or the amino acid sequence having one or more amino acids substituted, deleted, added and/or inserted in at least anywhere in the above amino acid sequence.

The preferred amino acid sequence mutant of FB54 (mouse antibody and humanized antibody) is an antibody in which the amino acid at the 4-position of CDR1 of its light chain has been mutated from "T" into "I", namely, the antibody in which the amino acid at the 4-position of CDR1 among the complementarity-determining regions in the light chain variable region is isoleucine. Concrete examples of such an antibody are antibodies having a feature described in any one of (a) to (i) below.

<matu002>

(a) comprising a light chain variable region including the amino acid sequence defined by SEQ ID NO: 19, and a heavy chain variable region including the amino acid sequence defined by SEQ ID NO: 20.

<matu089>

(b) comprising a light chain variable region including the amino acid sequence defined by SEQ ID NO:27, and a heavy chain variable region including the amino acid sequence defined by SEQ ID NO:28.

<matu014>

(c) comprising a light chain variable region including the amino acid sequence defined by SEQ ID NO:35, and a heavy chain variable region including the amino acid sequence defined by SEQ ID NO:36.

<matu020>

(d) comprising a light chain variable region including the amino acid sequence defined by SEQ ID NO:43, and a heavy chain variable region including the amino acid sequence defined by SEQ ID NO:44.

<matu024>

(e) comprising a light chain variable region including the amino acid sequence defined by SEQ ID NO:51, and a heavy chain variable region including the amino acid sequence defined by SEQ ID NO:52.

<matu039>

(f) comprising a light chain variable region including the amino acid sequence defined by SEQ ID NO:59, and a heavy chain variable region including the amino acid sequence defined by SEQ ID NO:60.

<matu054>

(g) comprising a light chain variable region including the amino acid sequence defined by SEQ ID NO:67, and a heavy chain variable region including the amino acid sequence defined by SEQ ID NO:68.

<matu062>

(h) comprising a light chain variable region including the amino acid sequence defined by SEQ ID NO:75, and a heavy chain variable region including the amino acid sequence defined by SEQ ID NO:76.

<matu072>

(i) comprising a light chain variable region including the amino acid sequence defined by SEQ ID NO:83, and a heavy chain variable region including the amino acid sequence defined by SEQ ID NO:84.

The "monoclonal antibody" in the present invention refers to an antibody (including an antibody fragment) obtained from a population of substantially homogeneous antibodies. As contrasted with a polyclonal antibody, the monoclonal antibody recognizes a single determinant on an antigen. The antibody of the present invention is an antibody separated and/or recovered (namely, isolated) from components in the natural environment.

The antibodies of the present invention include chimeric antibodies, humanized antibodies, human antibodies, and functional fragments of these antibodies. When the antibody of the present invention is administered to a human as a medicine, its form as a chimeric antibody, a humanized antibody or a human antibody is desirable from the viewpoint of reducing adverse reactions.

The "chimeric antibody" in the present invention refers to an antibody formed by joining a variable region of a certain type of antibody to a constant region of a different type of antibody. The chimeric antibody can be obtained, for example, by immunizing a mouse with an antigen, cutting an antibody variable region, which binds to the antigen, out of a gene of a monoclonal antibody from the mouse, bonding the antibody variable region to a human bone marrow-derived antibody constant region gene, integrating the bonding product into an expression vector, and transducing the expression vector into a host for production (for example, JP-A-7-194384, Japanese Patent No. 3238049, U.S. Pat. No. 4,816,397, U.S. Pat. No. 4,816,567, U.S. Pat. No. 5,807,715). The "humanized antibody" in the present invention is an antibody constructed by transplanting the genetic sequence of an antigen-binding site (CDR) of a nonhuman-derived antibody into a human antibody gene (CDR grafting), and methods for its preparation are publicly known (see, for example, Japanese Patent No. 2912618, Japanese Patent No. 2828340, Japanese Patent No. 3068507, European Patent No. 239400, European Patent No. 125023, and WO90/07861, WO96/02576). In the present invention, the "human antibody" refers to an antibody having all regions human-derived. For the preparation of the human antibody, it is possible to utilize a transgenic animal (e.g., mouse) which, when immunized, can produce a repertoire of human antibodies. Methods for preparation of the human antibody are publicly known (for example, Nature, 362:255-258 (1992), Intern. Rev. Immunol, 13:65-93 (1995), J. Mol. Biol, 222:581-597 (1991), Nature Genetics, 15:146-156 (1997), Proc. Natl. Acad. Sci. USA, 97:722-727 (2000), JP-A-10-146194, JP-A-10-155492, Japanese Patent No. 2938569, JP-A-11-206387, JP-T-8-509612, JP-T-11-505107). In the present Examples, success has been achieved in preparing chimeric antibodies and humanized antibodies having excellent reactivities with and excellent neutralizing activities against midkine on the basis of the FB54 gene (FIGS. 8 to 10, 19 to 21).

The "functional fragment" of the antibody in the present invention refers to a part of the antibody (partial fragment) which recognizes human midkine. Its concrete examples are Fab, Fab', F(ab')2, a variable region fragment (Fv), a disulfide bond Fv, single-stranded Fv (scFv), sc(Fv)2, and polymers of them.

The "Fab" refers to a monovalent antigen-binding fragment of an immunoglobulin which is composed of a light chain and a part of a heavy chain. The Fab can be obtained by papain digestion of the antibody, or by a recombination process. In the present Examples, the present invention has been successful in preparing Fab having excellent reactivity with midkine based on the FB54 gene (FIGS. 12 to 17). The "Fab'" is different from Fab because of the addition of limited amounts of residues at the carboxyl terminal of the heavy CH1 domain, including one or more cysteines of the hinge region of the antibody. The "F(ab')2" refers to a divalent antigen-binding fragment of an immunoglobulin composed of both light chains and portions of both heavy chains.

The "variable region fragment (Fv)" is the smallest antibody fragment having complete antigen recognizing and binding sites. Fv is a dimer having a heavy chain variable region and a light chain variable region joined more strongly by a noncovalent bond. The "single-stranded Fv (sFv)" includes the heavy chain variable region and the light chain variable region of the antibody, and these regions are present in a single polypeptide chain. The "sc(Fv)2" is in a single-stranded configuration composed of two heavy chain variable regions and two light chain variable regions bonded by a linker or the like.

The antibody of the present invention includes an antibody having an amino acid sequence modified without reductions in its desirable activities (for example, reactivity with human midkine and mouse midkine, neutralizing activity again human midkine, and tumor proliferation suppressing activity). Amino acid sequence mutants of the antibody of the present invention can be prepared by introduction of a mutation into DNA coding for the antibody chain of the present invention, or by peptide synthesis. Such a modification includes, for example, substitution, deletion, addition and/or insertion of the residue within the amino acid sequence of the antibody of the present invention. The site where the amino acid sequence of the antibody is altered may be the heavy chain or light chain constant region of the antibody, or may be the variable region (framework region or CDR), as long as the altered antibody has activity comparable to that of the antibody before alteration. The alteration of the amino acid in a portion other than CDR is assumed to exert relatively little influence on antigen-binding affinity. Nowadays, methods for screening for antibodies with affinity for antigens improved by alteration of the amino acid of CDR are publicly known (PNAS, 102:8466-8471 (2005), Protein Engineering, Design & Selection, 21:485-493(2008), WO2002/051870, J. Biol. Chem., 280: 24880-24887 (2005), Protein Engineering, Design & Selection, 21:345-351 (2008)). The amino acids to be altered are preferably 10 amino acids or less, more preferably 5 amino acids or less, most preferably 3 amino acids or less (for example, 2 amino acids or less, or 1 amino acid). Actually, in the present Examples, mutations were introduced into the variable regions of FB54 (framework regions and CDRs), and success was achieved in preparing a number of amino acid sequence mutants having excellent reactivities with human midkine and mouse midkine and excellent neutralizing activities against human midkine (Examples 22 to 24, FIG. 18).

In the present invention, moreover, an amino acid to be deamidated for the purpose of increasing the stability of the antibody, or an amino acid adjacent to the amino acid to be deamidated, may be substituted by other amino acid, whereby deamidation can be suppressed. Alternatively, glutamic acid can be substituted by other amino acid to increase the stability of the antibody. The present invention also provides an antibody stabilized in this manner.

The antibody of the present invention can be prepared by the hybridoma process or the recombinant DNA process. A typical example of the hybridoma process is the method of Kohler & Milstein (Nature, 256:495 (1975)). Antibody-producing cells used in the cell fusion step of this method are spleen cells, lymph node cells, peripheral blood leukocytes, etc. of an animal (e.g., mouse, rat, hamster, rabbit, monkey, goat) immunized with an antigen (human midkine, its partial peptide, or cells expressing them). It is also possible to use antibody-producing cells obtained by allowing an antigen to act in a culture medium on the above cells or lymphocytes isolated in advance from an unimmunized animal. As myeloma cells, publicly known various cell strains can be used. The antibody-producing cells and myeloma cells may originate in different animal species, if they are mutually fusible; preferably, however, they are of the same animal species origin. Hybridomas, for example, are produced by cell fusion between spleen cells obtained from an antigen-immunized mouse and mouse myeloma cells, and subsequent screening can obtain hybridomas producing a monoclonal antibody against human midkine. The monoclonal antibody against human midkine can be yielded from a culture of the hybridomas, or from an ascitic fluid of a mammal administered the hybridomas.

The recombinant DNA process is a method for producing the antibody of the present invention as a recombinant antibody by cloning DNA encoding the antibody or peptide of the present invention from hybridomas or B cells, integrating the clone into a suitable vector, and transducing the vector into host cells (e.g., mammalian cell line, E. coli, yeast cells, insect cells, plant cells, etc.) (for example, P. J. Delves, Antibody Production: Essential Techniques, 1997 WILEY, P. Shepherd and C. Dean Monoclonal Antibodies, 2000 OXFORD UNIVERSITY PRESS, Vandamme A. M. et al., Eur. J. Biochem. 192:767-775 (1990)). For the expression of DNA encoding the antibody of the present invention, DNA encoding the heavy chain and DNA encoding the light chain may be separately integrated into expression vectors to transform host cells, or DNA encoding the heavy chain and DNA encoding the light chain may be integrated into a single expression vector to transform host cells (see WO94/11523). The antibody of the present invention can be yielded in a substantially pure uniform shape by culturing the above host cells, and separating and purifying the product from within the host cells or from a culture broth. For the separation and purification of the antibody, a customary method used in polypeptide purification can be used. If a transgenic animal (cattle, goat, sheep or pig) incorporating the antibody gene is prepared using a transgenic animal preparation technology, monoclonal antibodies derived from the antibody gene can be yielded in large amounts from the milk of the transgenic animal.

The present invention provides a DNA coding for the antibody of the present invention, and a vector containing the DNA. The invention also provides a cell or an organism which produces the antibody of the present invention, or which contains the DNA of the present invention. Further, the present invention provides a method for producing the antibody, including the steps of culturing the cell, or breeding the organism, and recovering the antibody. Examples of the cell, which produces the antibody of the present invention or which contains the DNA of the present invention, are the aforementioned hybridomas and the aforesaid host cells. Examples of the organism, which produces the antibody of the present invention or which contains the DNA of the present invention, are the aforementioned transgenic animal and the aforementioned animal immunized with the antigen or the like.

Since the antibody of the present invention has neutralizing activity against human midkine, it can be used as a therapeutic drug and a prophylactic drug for a midkine-related disease. Examples of the midkine-related disease are diseases due to cell proliferation or neovascularization, such as cancer (neuroblastoma, glioblastoma, esophageal carcinoma, thyroid carcinoma, bladder cancer, large bowel cancer, stomach cancer, pancreatic cancer, breast cancer, liver cancer, pulmonary cancer, mammary carcinoma, uterine cancer, ovarian cancer, prostatic cancer, Wilms tumor), and endometriosis; inflammatory diseases or chemotaxis-associated diseases, such as arthritis, autoimmune diseases (organ-specific autoimmune disease, etc.), articular rheumatism (rheumatoid arthritis (RA), osteoarthrosis (OA)), multiple sclerosis (relapsing-remitting multiple sclerosis, etc.), inflammatory enteritis (Crohn disease, etc.), systemic lupus erythematosus (SLE), progressive systemic sclerosis (PSS), Sjögren syndrome, polymyositis (PM), dermatomyositis (DM), polyarteritis nodosa (PN), thyroid disease (Basedow disease, etc.), Guillain-Barré syndrome, primary biliary cirrhosis (PBC), sudden thrombocytopenic purpura, autoimmune hemolytic anemia, myasthenia gravis (EAMG), amyotrophic lateral sclerosis (ALS), type 1 diabetes mellitus, transplant rejection, postoperative adhesion, endometriosis, psoriasis, lupus, allergy, asthma, and neutrophil dysfunction; and vascular obstructive diseases or diseases attributed to intimal thickening, such as restenosis after revascularization, coronary vascular obstructive disease, cerebrovascular obstructive disease, renovascular obstructive disease, peripheral vessel obstructive disease, arteriosclerosis, and cerebral infarction. Thus, the present invention also provides a drug for treating or preventing a midkine-related disease, the drug containing the antibody of the present invention as an active principle; and provides a method for treating or preventing a midkine-related disease, including the step of administering an effective amount of the inventive antibody to a mammal including a human.

The antibody of the present invention, as shown in the present Examples, has the excellent activity of suppressing tumor proliferation, and is thus suitable as an anticancer drug. Thus, the present invention, in its preferred embodiments, also provides an anticancer drug containing the antibody of the present invention as an active principle; and provides a method for treating or preventing cancer, including the step of administering an effective amount of the inventive antibody to a patient (e.g., a mammal including a human).

The anticancer drug containing the antibody of the present invention as an active principle can be used in the form of a composition containing the antibody of the present invention and an optional ingredient, for example, physiological saline, an aqueous solution of glucose, or a phosphate buffer solution. The pharmaceutical composition of the present invention may be formulated, if desired, in a liquid or lyophilized form, and may optionally contain a pharmaceutically acceptable carrier or medium, for example, a stabilizer, a preservative, an isotonizing agent or the like.

As the pharmaceutically acceptable carrier, mannitol, lactose, saccharose, and human albumin can be cited as examples in the case of the lyophilized preparation. In the case of the liquid preparation, examples of the carrier are, but not limited to, physiological saline, water for injection, a phosphate buffer solution, and aluminum hydroxide.

The method of administering the anticancer drug of the present invention differs according to the age, body weight, sex, health state, etc. of the subject for administration. However, the anticancer drug can be administered by any of the following routes, oral route and parenteral route (e.g., intravenous administration, intraarterial administration, local administration). The preferred method of administration is the parenteral administration. The dosage of the anticancer drug of the present invention can be varied according to the age, body weight, sex or health condition of the patient, the degree of progression of cancer, and the ingredients of the anticancer drug to be administered. Generally, for intravenous administration, the dosage for an adult is 0.1 to 1000 mg, preferably 1 to 100 mg, daily per kg body weight.

Since the antibody of the present invention has excellent reactivity with human midkine and mouse midkine, it is expected to be applied as an agent for the detection of these midkines (for example, detection in experiments or diagnosis) or for the purification of the midkines. When used for detection of midkine, the antibody of the present invention may be a labeled one. For labeling, a radioactive substance, a fluorescent dye, a chemiluminescent substance, an enzyme, or a coenzyme, for example, can be used. Their examples are radioisotopes, fluorescein, rhodamine, dansyl chloride, luciferase, peroxidase, alkaline phosphatase, lysozyme, and biotin/avidin. In formulating the antibody of the present invention as a drug, an optional means appropriate for the intended purpose can be adopted to obtain the drug in an arbitrary dosage form. For example, it is permissible to measure the purified antibody for the antibody titer, dilute it appropriately with PBS (phosphate buffer solution containing physiological saline) or the like, and then add 0.1% sodium azide or the like as a preservative. It is also possible, for example, to determine the antibody titer of the inventive antibody adsorbed to latex or the like, dilute it at a suitable ratio, and add a preservative before use.

EXAMPLES

The present invention will now be described more specifically based on the following Examples, but is in no way limited to these Examples.

(Example 1) Acquisition of cDNA of MK

Based on the cDNA sequence of human MK (NM_001012333), primers to be shown below were designed in a 5'UTR region and a 3'UTR region. From total RNA extracted from human prostatic cancer cells PC3, cDNA was prepared using SuperScriptIII cells direct cDNA Synthesis System (Invitrogen). Using it as a template, cDNA containing the protein coding region full length of MK was amplified by nested PCR using KOD Plus Ver.2 (TOYOBO). The $1^{st}$ PCR conducted amplification with 25 cycles of [98° C. 20 seconds, 57° C. 20 seconds, 68° C. 45 seconds], and the $2^{nd}$ PCR conducted amplification with 30 cycles of [98° C. 15 seconds, 58° C. 15 seconds, 68° C. 45 seconds]. The amplification product of the $2^{nd}$ PCR was cloned into the cloning vector pT7Blue T-Vector (Novagen) to confirm its nucleotidesequence. Confirmation of the nucleotide sequence used an autosequencer (Applied Biosystems). The cloned cDNA coincided with the sequence of human MK, and was thus designated as hMK-pT7.

```
1stPCR
5' primer:
                                      (SEQ ID NO: 85)
5'-GAGTCGCCTCTTAGCGGATGC-3'

3' primer:
                                      (SEQ ID NO: 86)
5'-GCTCCTTGGCATCCAGGCTTG-3'

2nd PCR
5' primer:
                                      (SEQ ID NO: 87)
5'-CGGATGCAGCACCGAGGCTTC-3'

3' primer:
                                      (SEQ ID NO: 88)
5'-GGCTTGGCGTCTAGTCCTTTCC-3'
```

Similarly, cDNA containing the protein coding region full length of mouse MK was amplified. Mouse fetus visceral tissue-derived cDNA was used as a template. Primers were designed based on the DNA sequence of mouse MK (NM_001012336). The cloned cDNA coincided with the sequence of mouse MK, and was thus designated as mMK-pT7.

```
1st PCR
5' primer:
                                      (SEQ ID NO: 89)
5'-AAGCATCGAGCAGTGAGCGAGATG-3'

3' primer:
                                      (SEQ ID NO: 90)
5'-AACAAGTATCAGGGTGGGGAGAAC-3'

2nd PCR
5' primer:
                                      (SEQ ID NO: 91)
5'-GATGCAGCACCGAGGCTTCTTC-3'

3' primer:
                                      (SEQ ID NO: 92)
5'-TATGGGGAGGCTCACTTTCCAG-3'
```

(Example 2) Production of Cells Secreting and Expressing MK

Animal cells expressing the aa1-aa121 portion of human MK (MKver10) or the aa57-aa121 portion of human MK (MKver50), or aa1-aa119 of mouse MK (mMK) were produced in the following manner:

An MK partial length fragment amplified by PCR using primers indicated below, with hMK-pT7 or mMK-pT7 as a template, was cleaved at the ends with NotI and BamHI, and inserted into the NotI-BamHI site of an expression vector for animal cells. As the expression vector for animal cells, there was used pQCxmhIPG controlled by a CMV promoter and expressing the target gene and Puromycin-EGFP fused protein simultaneously by use of an IRES sequence. The pQCxmhIPG is a vector modified by the inventors from pQCXIP Retroviral Vector of "BD Retro-X Q Vectors" (Clontech). The resulting vectors were designated as MKver10-pQCxmhIPG, MKver50-pQCxmhIPG, and mMK-pQCxmhIPG.

```
MKver10
5' primer:
5'-aataGCGGCCGCACCATGCAGCACCGAGGCTTCCTC-3'
(SEQ ID NO: 93; the underlined portion is NotI
recognition sequence)

3' primer:
5'-cgGGATCCGTCCTTTCCCTTCCCTTTCTTG-3'
(SEQ ID NO: 94; the underlined portion is BamHI
recognition sequence)

MKver50
5' primer:
5'-aataGCGGCCGCGGAGTTTGGAGCCGACTGC-3'
(SEQ ID NO: 95; the underlined portion is NotI
recognition sequence)

3' primer:
5'-cgGGATCCGTCCTTTCCCTTCCCTTTCTTG-3'
(SEQ ID NO: 96; the underlined portion is BamHI
recognition sequence)

mMK
5' primer:
5'-aataGCGGCCGCACCATGCAGCACCGAGGCTTCTTC-3'
(SEQ ID NO: 97; the underlined portion is NotI
recognition sequence)
```

```
-continued
3' primer:
5'-cgGGATCCGTCCTTTCCTTTTCCTTTCTTGGC-3'
(SEQ ID NO: 98; the underlined portion is BamHI
recognition sequence)
```

MK secreting/expressing cell lines were prepared using Pantropic Retroviral Expression System (Clontech: K1063-1). GP2-293 (Clontech: K1063-1) in an 80 to 90% confluent state was readied in a collagen-coated 100 mm dish, and the expression vectors constructed above (MKver10-pQCxm-hIPG, MKver50-pQCxmhIPG, or mMK-pQCxmhIPG) and pVSV-G (Clontech: K1063-1) were cotransduced in an amount of 11.2 µg each using Lipofectamine 2000 (Invitrogen). After a lapse of 48 hours, the supernatant containing viral particles was recovered, and the viral particles were precipitated by ultracentrifugation (18,000 rpm, 1.5 hours, 4° C.). The precipitate was suspended with 30 µL THE (50 mM Tris-HCl [pH=7.8], 130 mM NaCl, 1 mM EDTA) to prepare a retrovirus vector concentrate. The retrovirus vector concentrate (5 µL) was diluted with 150 µL DMEM (SIGMA: D5796)-10% FBS containing 8 µg/mL hexadimethrine bromide (SIGMA: H-9268) to prepare a viral particles-containing culture medium. A culture medium of 293T readied so as to be in an approximately 40% confluent state on a 96-well microplate was replaced by the prepared viral particles-containing culture medium to introduce the desired gene. After introduction, the gene was expansively cultured with DMEM (SIGMA: D5796)-10% FBS containing 5 µg/mL Puromycin (SIGMA: P-8833) to establish antigen expression cell lines (MKver10/st293T, MKver50/st293T, mMK/st293T).

(Example 3) Preparation MK Purified Proteins (Animal Cell-Derived Recombinant Proteins)

The expression cell lines established as above (MKver10/st293T, MKver50/st293T, mMK/st293T) were each cultured with 1 L CD293 (Invitrogen). The culture supernatant was recovered, and recombinant proteins (MKver10, MKver50, mMK) were each purified therefrom using TALON Purification Kit (Clontech: K1253-1), followed by confirming the purified proteins by SDS-PAGE and Western blot. Their protein concentrations were determined using Protein Assay Kit II (BioRad: 500-0002JA).

(Example 4) Production of E. coli Expressing MK

E. coli recombinant proteins of the aa23-aa121 (MKver60) and aa57-aa121 (MKver80) portions of human MK were produced in the following manner: An MK partial length fragment amplified by PCR using primers indicated below, with hMK-pT7 as a template, was cleaved at the ends with BamHI and XhoI, and inserted into the BamHI-XhoI site of pET28a to construct E. coli expression vectors. Using these vectors, BL21 was transformed. The resulting transformants were designated as MKver60/BL21 and MKver80/BL21.

```
MKver60
5' primer:
5'-cgGGATCCAAAAAGAAAGATAAGGTGAAGAAG-3'
(SEQ ID NO: 99; the underlined portion is BamHI
recognition sequence)

3' primer:
5'-ccgCTCGAGGTCCTTTCCCTTCCCTTTCTTG-3'
(SEQ ID NO: 100; the underlined portion is XhoI
recognition sequence)

MKver80
5' primer:
5'-cgGGATCCGAGTTTGGAGCCGACTGCAAG-3'
(SEQ ID NO: 101; the underlined portion is BamHI
recognition sequence)

3' primer:
5'-ccgCTCGAGGTCCTTTCCCTTCCCTTTCTTG-3'
(SEQ ID NO: 102; the underlined portion is XhoI
recognition sequence)
```

(Example 5) Preparation of MK Purified Proteins (E. coli-Derived Recombinant Proteins)

The E. coli strains MKver60/BL21 and MKver80/BL21 established as above were each cultured in a 1 L kanamycin-containing LB medium, and induced expression was performed using 1 mM IPTG. The resulting recombinant proteins were each purified from a PBS soluble fraction with the use of TALON Purification Kit (Clontech: K1253-1). The purified proteins were confirmed by SDS-PAGE and Western blot. Their protein concentrations were determined using Protein Assay Kit II (BioRad: 500-0002JA).

(Example 6) Immunization with Antigen

MKver10, MKver50, MKver60, or MKver80 was mixed with the same amount of a complete adjuvant (SIGMA: F5881) to form an emulsion. Four- to 5-week-old Balb/c mice (Japan SLC, Inc.) were immunized with 5 to 20 µg of the emulsion per mouse 6 times at intervals of 3 to 7 days. Lymphocytes were extracted from the mouse 3 days after final immunization, and fused to mouse myeloma cells P3U1 (P3-X63Ag8U1).

(Example 7) Cell Fusion

Cell fusion was performed basically by the following general method: FBS in all culture media was inactivated, before use, by a treatment involving heat insulation at 56° C. for 30 minutes. P3U1 was cultured in RPMI1640-10% FBS (containing penicillin-streptomycin) and readied. The extracted mouse lymphocytic cells and P3U1 were mixed at a ratio of 10:1 to 2:1, and centrifuged. To the precipitated cells, 50% polyethylene glycol 4000 (Merck: 1.09727.0100) was slowly added with gentle mixing, and then the mixture was centrifuged. Precipitated fused cells were diluted, as appropriate, with a 15% FBS-containing HAT medium (RPMI1640, HAT-supplement (Invitrogen: 11067-030), penicillin-streptomycin), and the dilution was inoculated to a 96-well microplate in an amount of 200 µL/well. The fused cells were cultured in a $CO_2$ incubator (5% $CO_2$, 37° C.) and, when colonies were formed, the culture supernatant was sampled, and screened as described below.

(Example 8) Selection of Anti-MK Monoclonal Antibody Producing Cells

Hybridomas producing anti-MK antibodies were selected by enzyme-linked immunosorbent assay (ELISA). The assay used the aforementioned recombinant human MK (MKver10) which had been dispensed in a 96-well ELISA plate (nunc) in an amount of 0.5 µg/mL (50 µL/well) and left to stand for 2 hours at room temperature or overnight at 40° C. for adsorption. After removal of the resulting solution, 1% BSA (Nacalai: 01863-35)-5% Sucrose (WAKO)-PBS was added in an amount of 150 µL/well, and the system was allowed to stand for 2 hours at room temperature to block the remaining active groups. After standing of the system, the resulting solution was removed, and the hybridoma culture supernatant (50 µL/well) was dispensed as a primary antibody, whereafter the system was allowed to stand for 1 hour. After the plate was washed with 0.05% Tween 20-PBS, HRP-labeled goat anti-mouse IgG (MBL: 330) diluted 1:10000 was added as a secondary antibody in an amount of 50 µL/well, and the system was allowed to stand for 1 hour at room temperature. After the plate was washed with 0.05% Tween 20-PBS, a color developing solution (5 mM sodium citrate, 0.8 mM 3,3',5,5'-tetramethylbenzidine-2HCl, 10% N,N-dimethylformamide, 0.625% polyethylene glycol 4000, 5 mM citric acid monohydrate, 5 mM $H_2O_2$) was added in an amount of 50 µL/well, and the system was allowed to stand for 20 minutes at room temperature to develop a color. 1M phosphoric acid was added in an amount of 50 µL/well to terminate color development, and then the absorbance at 450 nm was measured using a plate reader (Thermo Fisher Scientific).

The cells selected here were expansively cultured in a 15% FBS-containing HT medium (RPMI1640, HT-supplement (Invitrogen: 21060-017), Penicillin-Streptomycin), and then they were subjected to monocloning by the limiting dilution method.

In the above manner, a total of 48 hybridomas producing anti-MK antibodies were obtained (5 clones with MKver10 as an immunogen, 4 clones with MKver50 as an immunogen, 31 clones with MKver60 as an immunogen, and 8 clones with MKver80 as an immunogen).

(Example 9) Reactivity of Obtained Antibodies with MK

From the culture supernatant of each hybridoma clone, antibodies were purified by the general affinity purification method using Protein A-Sepharose. The reactivities of these antibodies with human MK were confirmed by enzyme-linked immunosorbent assay (ELISA) in the same manner as stated earlier. The anti-MK antibody at a maximum concentration of 5 µg/mL was serially diluted with PBS, and used as a primary antibody. As a result, it was confirmed that all the antibodies reacted concentration-dependently with the recombinant human MK (FIGS. 1 to 4).

Figure 1:
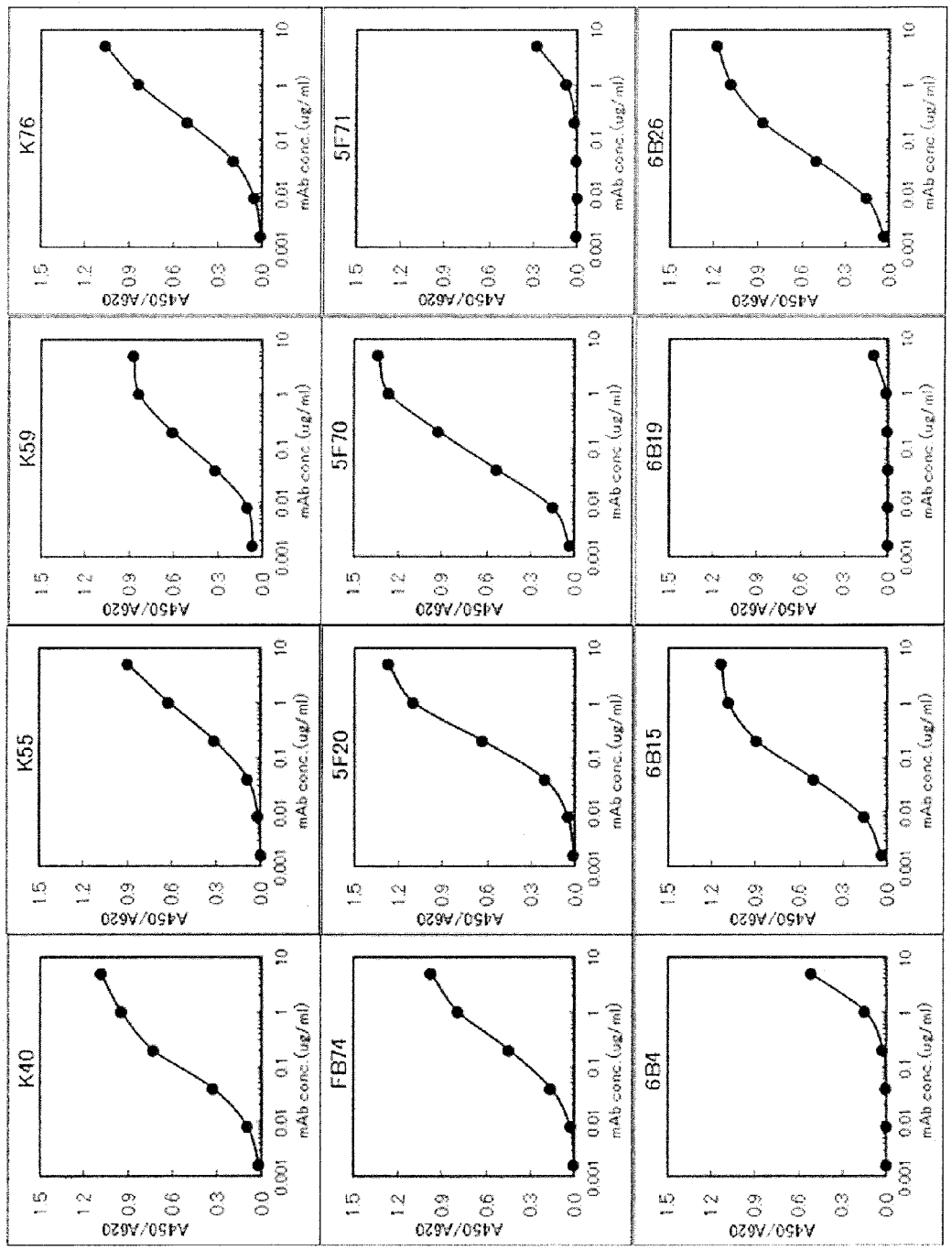
FIG. 1 is graphs showing the results of analyses by ELISA of the reactivities of the acquired anti-midkine monoclonal antibodies with recombinant human midkine.
Figure 2:
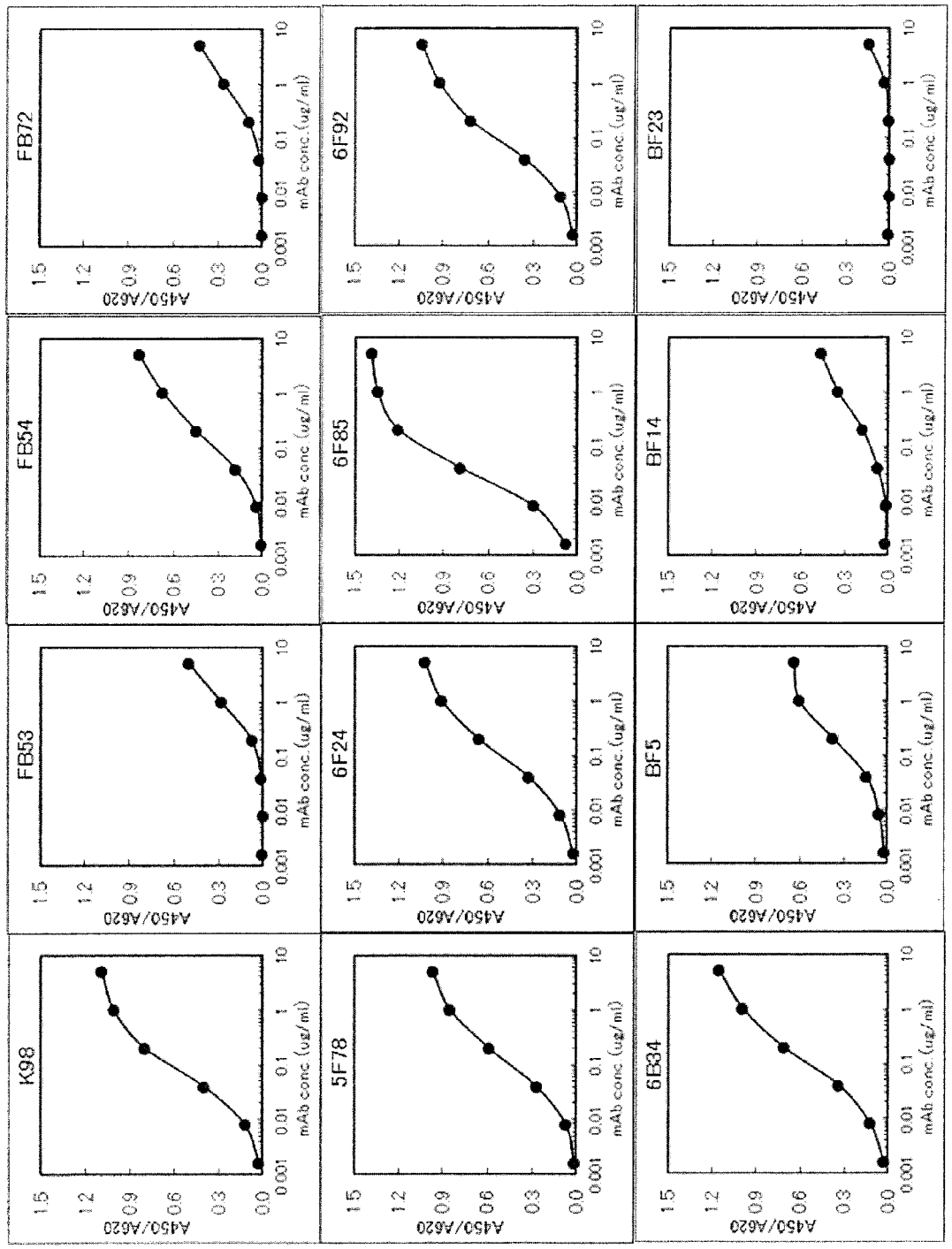
FIG. 2 is graphs showing the results of analyses by ELISA of the reactivities of the acquired anti-midkine monoclonal antibodies with the recombinant human midkine.
Figure 3:
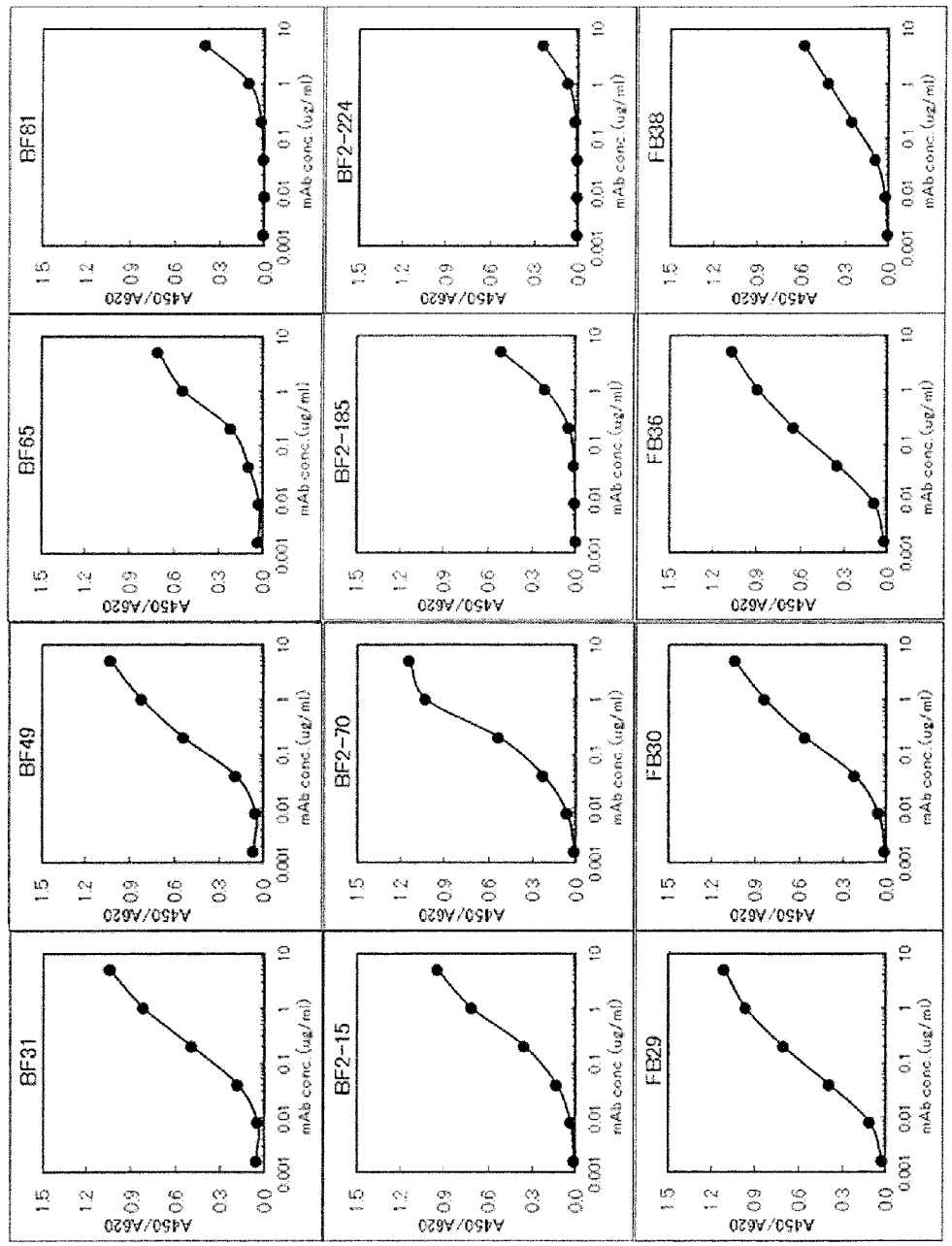
FIG. 3 is graphs showing the results of analyses by ELISA of the reactivities of the acquired anti-midkine monoclonal antibodies with the recombinant human midkine.
Figure 4:
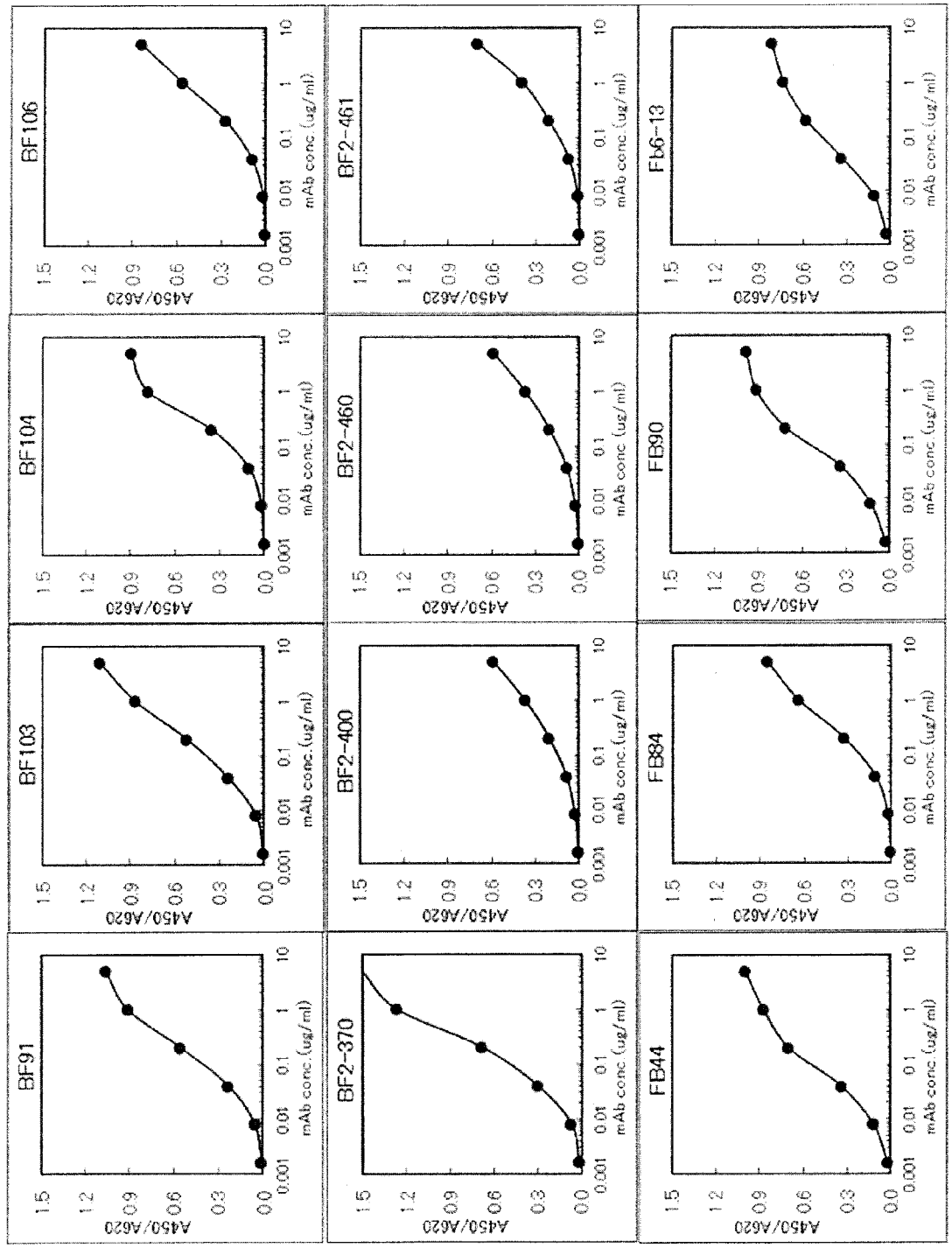
FIG. 4 is graphs showing the results of analyses by ELISA of the reactivities of the acquired anti-midkine monoclonal antibodies with the recombinant human midkine.
Figure 5:
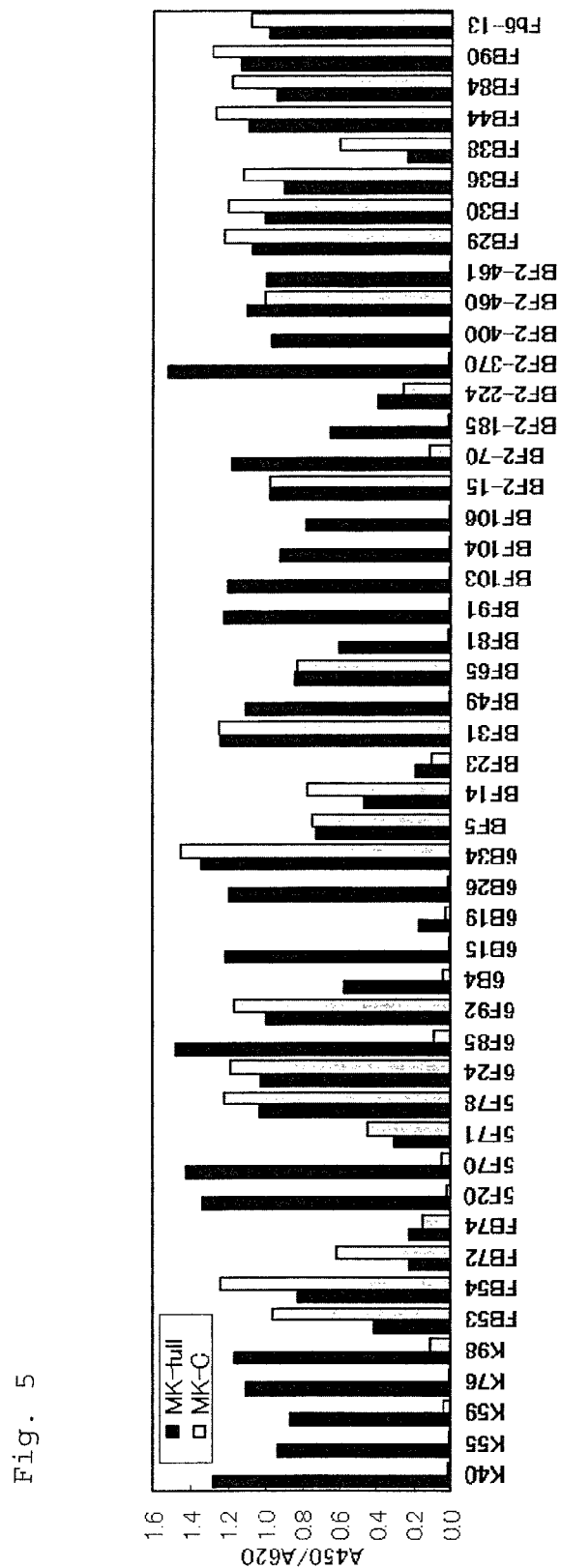
FIG. 5 is a graph showing the results of analyses by ELISA of the recognition sites in human midkine for the acquired anti-midkine monoclonal antibodies. "MK-full" represents the reactivity of each antibody with the human midkine full length, and "MK-C" represents the reactivity of each antibody with the human midkine C-terminal side (polypeptide comprising amino acids at positions 60 to 120).

It was also confirmed by the same ELISA that the antibodies reacted with MK prepared by peptide synthesis (PEPTIDE INSTITUTE, INC.: 4298-v). Based on these findings, the resulting antibodies were confirmed to recognize MK, rather than the tag portion or linker portion of the recombinant protein. Furthermore, their reactivity with the C-terminal side purified peptide of MK (aa60-aa121) (PEPTIDE INSTITUTE, INC.: 4299-s) was also evaluated by ELISA. These assays used the full length or C-terminal side purified peptide of MK (PEPTIDE INSTITUTE, INC.: 4298-v or 4299-s) which had been dispensed in an ELISA plate (nunc) in an amount of 0.5 µg/mL or 50 µL/well and allowed to stand overnight at 4° C. for adsorption. The anti-MK antibody adjusted to 5 µg/mL with PBS was used as a primary antibody. As a result, 25 of the obtained antibodies showed comparable reactivity with the full length and the C-terminal side. Hence, they were judged to be antibodies recognizing the C-terminal site, while the other 23 antibodies were judged to be antibodies recognizing the N-terminal region of MK (FIG. 5). From left to right in the drawing, the 5 clones K40 to K98, the 4 clones FB53 to FB74, the 31 clones 5F20 to BF2-461, and the 8 clones FB29 to Fb6-13 are antibodies obtained with MKver10, ver50, ver60 and ver80 as immunogens.

On the other hand, the reactivity with pleiotrophin, the only factor belonging to the same family as MK, was evaluated similarly by ELISA. For this assay, the full length purified peptide of pleiotrophin (PEPTIDE INSTITUTE, INC.: 4335-v) was used. The antibodies obtained showed no reactivity with pleiotrophin, and were thus judged to recognize MK specifically.

(Example 10) Construction of Expression Vector Expressing AP-Labeled MK

Whether or not the obtained anti-MK antibodies have MK neutralizing activity was evaluated by having them inhibit MK from binding to the receptor on the cell surface (AP-MK binding inhibition assay). A recombinant protein having alkaline phosphatase (AP) fused to the N-terminal of aa23-121 of MK (AP-MK) was prepared as described below.

MK cDNA amplified by PCR using primers indicated below was cleaved at the ends with XhoI and XbaI, and inserted into the XhoI-XbaI site of pAPtag-5 vector (GenHunter, QV5) to construct an expression vector. This vector was designated as MK-APtag5.

Forward primer: 5'-<u>CTCGAG</u>AAAAAGAAAGATAAGGTG-3'

(SEQ ID NO: 103; the underlined portion is XhoI recognition sequence)

Reverse primer: 5'-<u>TCTAGA</u>CTAGTCCTTTCCCTTCCC-3'

(SEQ ID NO: 104; the underlined portion is XbaI recognition sequence)

(Example 11) Preparation of AP-Labeled MK and AP $2.0 \times 10^6$ cells of 293T were inoculated to a 100 mm dish coated with collagen I. After a lapse of 24 hours, the culture medium was replaced by 10 ml OPTI-MEM I (GIBCO: 31985) containing 1% Insulin-Transferrin-Selenium-A (GIBCO: 51300-044) at a concentration of 1%. An Eppendorf tube was charged with 600 µL OPTI-MEM I and 15 µL FuGENE6 (Roche: 1815091), which were blended, and allowed to stand for 5 minutes at room temperature. Then, 7.5 µg of the expression vector (MK-APtag5 or pAPtag-5) was added for mixing, and the mixture was allowed to stand further for 15 minutes. The mixture was added to the culture medium of the 293T cells, and the system was cultured for 5 days at 37° C. The culture medium was recovered into protein low binding PROTEOSAVE SS (SUMITOMO BAKELITE: MS-52150), and centrifuged for 5 minutes at 1500 rpm, whereafter the supernatant was passed through a 0.22 µm filter. The activity of AP-MK or AP in the recovered solution was measured as follows:

To 2 µL of the culture supernatant, 48 µL Milli-Q water and 50 µL AP assay reagent A (GenHunter: Q501) were added, and the mixture was allowed to stand for 10 minutes at 37° C. to develop a color. 0.5N NaOH was added in an amount of 100 µL to terminate color development, and 800 µL Milli-Q water was added. Then, the absorbance at 405 nm was measured using Shimadzu UV 160 Spectrophotometer. The AP activity was calculated from the measured absorbance. For this calculation, the following equation was used:

AP activity [U/ml]=(OD405×54)/(reaction time [min]×liquid amount [µl])

(Example 12) AP-MK Binding Inhibition Assay $1.0 \times 10^5$ cells of TNB1 cells were inoculated to a 6-well plate coated with collagen I. After a lapse of 24 hours, the culture medium was removed, and the system was washed once with HBHA (0.5 mg/mL BSA-20 mM HEPES (pH7.8)-HBSS (GIBCO: 14175)). Then, AP-MK or AP diluted to 0.6 U/ml with OPTI-MEM was added in an amount of 1 mL/well, and the system was allowed to stand for 90 minutes at room temperature. On this occasion, the anti-MK antibody or control antibody for evaluation of the AP-MK binding inhibition activity was added in an amount of 90 µg/mL.

After washing 5 times with HBHA, Cell Lysis Buffer (GenHunter: Q504) was added in an amount of 200 µL/well for cell lysis, and a cell extract was recovered. The cell extract was centrifuged (4° C., 15000 rpm, 2 min), and the supernatant separated was treated for 10 minutes at 65° C. Then, 50 µL of the treated supernatant was aliquoted, 50 µL AP assay reagent A (GenHunter: Q501) was added, and the mixture was allowed to stand for 30 minutes at 37° C. to develop a color. 0.5N NaOH (100 µL) was added to terminate color development, and 800 µL Milli-Q water was added. Then, the absorbance at 405 nm was measured using Shimadzu UV 160 Spectrophotometer. The AP activity was calculated from the measured absorbance by use of the aforementioned equation. With the AP activity in the well containing only AP-MK as 100%, the AP activities in the respective wells were expressed as relative values.

Some of the results are shown in FIG. 6. Each assay was conducted for 3 wells, and the results are indicated by mean values and error bars. The AP activity was lowered to 75.5%, 29.5%, and 61.4%, respectively, in the wells containing FB53, FB54 and FB72, as compared with the wells containing AP-MK alone. No decline in the AP activity was observed in the wells containing the anti-MK antibodies other than FB53, FB54 and FB72, and the control antibody. Of the anti-MK antibodies obtained, therefore, the three antibodies FB53, FB54 and FB72 were found to have the activity of inhibiting AP-MK from binding to the receptor. As shown in FIG. 6, moreover, FB54 among these three antibodies was demonstrated to have the strongest activity of inhibiting the binding of AP-MK to the receptor.

(Example 13) Production of Cells Secreting and Expressing Mutant MKs

Animal cells expressing mutant MKs (MK-W69A, -K79Q, -R81Q, -K102Q) were produced in the following manner:

With MKver10-pQCxmhIPG as a template, the 5' fragment and the 3' fragment, respectively, were amplified by PCR using primer pairs shown below. Approximately equal amounts of the respective amplification products were mixed, and fused together by PCR using a primer pair for fusion of the 5' fragment and the 3' fragment. The amplified fragments were cleaved at the ends with NotI and BamHI, and inserted into the NotI-BamHI site of an expression vector for animal cells. The above-mentioned pQCxmhIPG was used as the expression vector for animal cells. The constructed vectors were designated as MK-W69A-pQCxmhIPG, MK-K79Q-pQCxmhIPG, MK-R81Q-pQCxmhIPG, and MK-K102Q-pQCxmhIPG.

W69A
For 5' fragment:
(SEQ ID NO: 105)
5'-GAGACGCCATCCACGCTGTTTTG-3'
and
(SEQ ID NO: 106)
5'-CACGCACCCGCGTTCTCAAAC-3'

For 3' fragment:
(SEQ ID NO: 107)
5'-GTTTGAGAACGCGGGTGCGTG-3'
and
(SEQ ID NO: 108)
5'-GAGGGGCGGATAAACTCAATGGTG-3'

K79Q
For 5' fragment:
(SEQ ID NO: 105)
5'-GAGACGCCATCCACGCTGTTTTG-3'
and
(SEQ ID NO: 109)
5'-CTTGGCGGACTTGGGTGCCTG-3'

For 3' fragment:
(SEQ ID NO: 110)
5'-CAGGCACCCAAGTCCGCCAAG-3'
and
(SEQ ID NO: 108)
5'-GAGGGGCGGATAAACTCAATGGTG-3'

R81Q
For 5' fragment:
(SEQ ID NO: 105)
5'-GAGACGCCATCCACGCTGTTTTG-3'
and
(SEQ ID NO: 111)
5'-GGTGCCTTGCTGGACTTTGGTG-3'

For 3' fragment:
(SEQ ID NO: 112)
5'-CACCAAAGTCCAGCAAGGCACC-3'
and
(SEQ ID NO: 108)
5'-GAGGGGCGGATAAACTCAATGGTG-3'

K102Q
For 5' fragment:
(SEQ ID NO: 105)
5'-GAGACGCCATCCACGCTGTTTTG-3'
and
(SEQ ID NO: 113)
5'-CAGGGCTGGGTGACGCGGATG-3'

For 3' fragment:
(SEQ ID NO: 114)
5'-CATCCGCGTCACCCAGCCCTG-3'
and
(SEQ ID NO: 108)
5'-GAGGGGCGGATAAACTCAATGGTG-3'

Fusion between 5' fragment and 3' fragment
(SEQ ID NO: 105)
5'-GAGACGCCATCCACGCTGTTTTG-3'
and
(SEQ ID NO: 108)
5'-GAGGGGCGGATAAACTCAATGGTG-3'

Using the underlined nucleotides, amino acids were substituted. Moreover, 5'-GAGACGCCATCCACGCT-GTTTTG-3' (SEQ ID NO: 105) and 5'-GAGGGGCGGA- TAAACTCAATGGTG-3' (SEQ ID NO: 108) are sequences corresponding to the outside of the MK coding region of the expression vector.

Using the so constructed expression vectors, cell lines secreting and expressing mutant MK were established by the same method as the above method (MK-W69A/st293T, MK-K79Q/st293T, MK-R81Q/st293T, MK-K102Q/st293T).

(Example 14) Preparation of Mutant MK Purified Proteins

The established expression cell lines were each cultured with 500 mL CD293 (Invitrogen). The culture supernatant was recovered, and mutant MK recombinant proteins (MK-W69A, MK-K79Q, MK-R81Q, MK-K102Q) were purified by the same method as described above.

(Example 15) Reactivities of Obtained Antibodies with Mutant MKs

The reactivities of the resulting antibodies with the mutant MKs were confirmed by the same enzyme-linked immunosorbent assay (ELISA) as described above. The assays used plates having wild type human MK (MKver10) or the above-mentioned mutant MK (MK-W69A, MK-K79Q, MK-R81Q and MK-K102Q) adsorbed thereto. The anti-MK antibody at a maximum concentration of 5 µg/mL was serially diluted with PBS, and used as a primary antibody. As examples of the antibodies recognizing the N-terminal side or the C-terminal side of midkine, but showing no neutralizing activity, BF106 and FB74 were also evaluated similarly.

Some of the results are shown in FIG. 7. The three antibodies showing neutralizing activity, FB53, FB54 and FB72, had lower reactivity with the mutant MK than reactivity with the wild type MK. The other anti-MK antibodies showing no neutralizing activity reacted with the mutant MK as with the wild type MK.

(Example 16) Isolation of Heavy Chain and Light Chain Variable Region Genes of FB54 Antibody and Identification of their CDRs The hybridoma was cultured, and its total RNA was extracted by a general method. Then, cDNA was obtained by the 5'-RACE method using GeneRacer Kit (Invitrogen). With this cDNA as a template, PCR (35 cycles, each cycle comprising [94° C. 30 seconds, 57° C. 30 seconds, 72° C. 50 seconds]) was performed with Platinum Taq High Fidelity (Invitrogen) using GeneRacer 5' Primer (5'-CGACTGGAG-CACGAGGACACTGA-3' (SEQ ID NO: 115)) and CH1 (mouse IgG1 constant region 1) 3' Primer (5'-AATTTTCT-TGTCCACCTGG-3' (SEQ ID NO: 116)) to amplify the gene of the antibody heavy chain variable region (cDNA). In connection with the antibody light chain, on the other hand, PCR was performed in the same manner using GeneRacer 5' Primer and Cκ (κconstant region) 3' Primer (5'-CTAACACTCATTCCTGTTGAAGCTCT-3 (SEQ ID NO: 117)) to amplify the gene (cDNA). The amplified gene fragments of the heavy chain variable region and the light chain variable region were each cloned into pT7Blue T-Vector (Novagen). The resulting clones were analyzed for sequence by means of an autosequencer (Applied Biosystems). As a result, amino acids encoded by the resulting nucleotide sequences, and the sequences of the respective CDRs were determined. The results are as follows:

```
<FB54 heavy chain variable region>
                                        (SEQ ID NO: 8)
EVMLVESGGGLVKPGGSLKLSCAASGFTFSSYAMSWVRQTPEKRLEWVAT

ISSGGSYTYYPDSVKGRFTISRDNAKNTLYLQMSSLRSEDTAMYFCARHN

YRYDEYYYAMDYWGQGTSVTVSS

CDR1 of FB54 heavy chain variable region
                                        (SEQ ID NO: 4)
SYAMS CDR2 of FB54 heavy chain variable region
                                        (SEQ ID NO: 5)
TISSGGSYTYYPDSVKG CDR3 of FB54 heavy chain variable region
                                        (SEQ ID NO: 6)
HNYRYDEYYYAMDY <FB54 light chain variable region>
                                        (SEQ ID NO: 7)
ETTVTQSPTSLSMAIGEKVTIRCITSTDIDDEMNWYQQKPGEPPKLLISE

GNTLRPGVPSRFSSSGYGTDFVFTIENMLSEDVADYYCLQSDNLPYTFGG

GTKLEIK

CDR1 of FB54 light chain variable region
                                        (SEQ ID NO: 1)
ITSTDIDDEMN CDR2 of FB54 light chain variable region
                                        (SEQ ID NO: 2)
EGNTLRP CDR3 of FB54 light chain variable region
                                        (SEQ ID NO: 3)
LQSDNLPYT
```

(Example 17) Preparation of FB54 Chimerized Antibodies

Based on the determined gene sequences, primers for PCR amplification to be shown below were designed, and antibody variable regions were amplified by 2 rounds of PCR. On this occasion, the secretion signal sequences were converted into sequences recommended by Lonza, and restriction enzyme recognition sequences were added to the ends of the amplified fragments (HindIII recognition sequence and BamHI recognition sequence were added for the heavy chain variable region, while HindIII and BsiWI recognition sequences were added for the light chain variable region).

```
1st PCR for heavy chain
HC-signal-1:
5'-GTTCTTTCTGTCCGTGACCACAGGCGTGCATTCTGAAGTGATGCTGG

TGGAGTCTGG-3' (SEQ ID NO: 118)

HC-reverse:
5'-atataCTCGAGACGGTGACTGAGG-3' (SEQ ID NO: 119;

the underlined portion is BamHI recognition sequence)

2nd PCR for heavy chain
HC-signal-2:
5'-atataAAGCTTACCATGGAATGGAGCTGGGTGTTCCTGTTCTTTCTG TCCGTGACCACAGGCGTGC-3' (SEQ ID NO: 120; the underlined portion is HindIII recognition sequence)
```

-continued

HC-reverse:
5'-atataCTCGAGACGGTGACTGAGG-3' (SEQ ID NO: 119;

the underlined port ion is BamHI recognition sequence)

1st PCR for light chain
LC-signal-1:
5'-GGGACTGCTGCTGCTGTGGCTGACAGACGCCCGCTGTGAAACAACTG

TGACCCAGTCTCC-3' (SEQ ID NO: 121)

LC-reverse:
5'-atataCGTACGTTTGATTTCCAGCTTGGTGCC-3' (SEQ ID NO:

122; the underlined portion is BsiWI recognition sequence)

2nd PCR for light chain
LC-signal-2:
5'-atataAAGCTTACCATGTCTGTGCCTACCCAGGTGCTGGGACTGCTG CTGCTGTGGCTGACAGACGCC-3' (SEQ ID NO: 123; the underlined portion is HindIII recognition sequence)

LC-reverse:
5'-atataCGTACGTTTGATTTCCAGCTTGGTGCC-3' (SEQ ID NO:

122; the underlined portion is BsiWI recognition sequence).

The resulting PCR products were cleaved with the above restriction enzymes, and the cleaved products were inserted by the customary method into Lonza's human IgG1 antibody-producing vectors incorporating the constant region of human IgG1 (FB54-chH and FB54-chK). Based on a protocol recommended by Lonza, a chimeric antibody producing cell line was established. From its culture supernatant, a chimerized FB54 antibody was purified using Protein A. Hereinbelow, this antibody will be described as chFB54.

(Example 18) Evaluation of Reactivity of FB54 Chimerized Antibody

Figure 8:
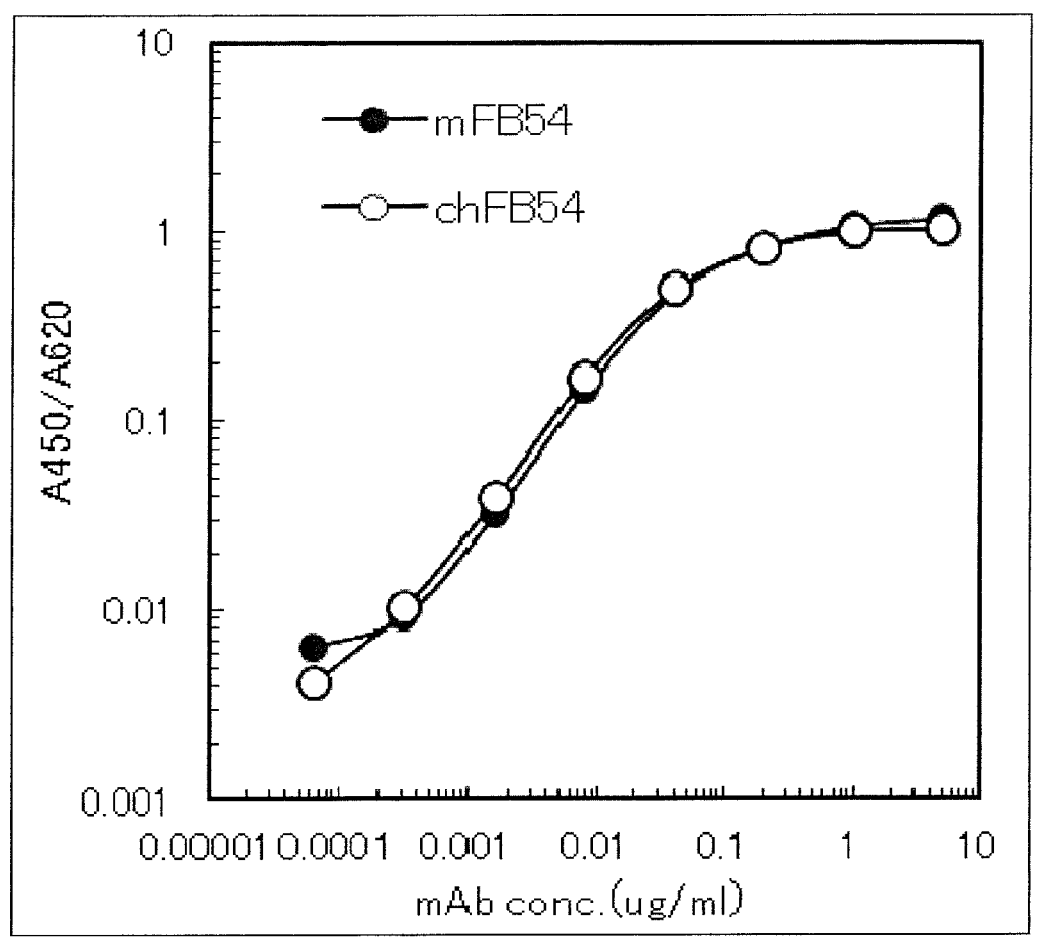
FIG. 8 is a graph showing the results of analyses by ELISA of the reactivities of an anti-human midkine mouse monoclonal antibody (mFB54) and its chimerized antibody (chFB54) with recombinant human midkine.

The reactivity of chFB54 with human MK was confirmed by enzyme-linked immunosorbent assay (ELISA). The assay was performed in the same manner as described above. The chFB54 or mouse FB54 antibody as a control, at a maximum concentration of 5 µg/mL, was serially diluted with PBS, and used as a primary antibody. HRP-labeled goat anti-human IgG (MBL: 206) or HRP-labeled goat antimouse IgG (MBL: 330) was used as a secondary antibody. As a result, chFB54 showed binding activity comparable to that of the original mouse antibody FB54 (FIG. 8)

(Example 19) Preparation of FB54 Humanized Antibodies

In accordance with the CDR-grafting method, human frameworks (hereinafter, FR1 to FR4 regions; collectively called FR regions) were selected, and substituted with CDRs of the mouse monoclonal antibody FB54. Concretely, a homology search was conducted in connection with the heavy chain FR regions versus the light chain FR regions, and the FB54 heavy chain was found to be highly homologous to the FR regions of Accession Number AF471493 of the human antibody. The homology of the FR regions was 73/87=83.9%. A humanized antibody heavy chain variable region was designed so that CDR1 to CDR3 of the FB54 heavy chain would be transplanted appropriately into the FR regions of AF471493. The corresponding humanized antibody heavy chain will be expressed as FB54-rHa. Similarly, the FB54 antibody light chain was found to be highly homologous to the FR regions of Accession Number X70463 of the human antibody. The homology of the FR regions was 55/80=68.8%. A humanized antibody light chain variable region was designed so that CDR1 to CDR3 of the FB54 light chain would be transplanted appropriately into the FR regions of X70463. The corresponding humanized antibody light chain will be expressed as FB54-rKa.

In connection with the light chain, there were further designed a light chain in which the VCI site of the FR region was converted into the amino acids used in the mouse germ line and, in addition, a light chain in which the amino acids at a distance of within 5 Å from the CDR were converted into the amino acids used in the mouse germ line. These light chains will sometimes be referred to hereinafter as FB54-rKb and FB54-rKc.

<AF471493>
(SEQ ID NO: 124)
EVQLVESGGGLVKPGGYLRLSCAASGFTFSLHSMSWVRQAPGKGLDWVAY

ITGSSNTIYYGDSVKGRFTISRDNAKNSLYLQMNSLTDDDTAVYFCARGP

ISAANTFDLWGQGTLVTVSS

FR1 of AF471493
(SEQ ID NO: 125)
EVQLVESGGGLVKPGGYLRLSCAASGFTFS

FR2 of AF471493
(SEQ ID NO: 126)
WVRQAPGKGLDWVA

FR3 of AF471493
(SEQ ID NO: 127)
RFTISRDNAKNSLYLQMNSLTDDDTAVYFCAR

FR4 of AF471493
(SEQ ID NO: 128)
WGQGTLVTVSS

<FB54-rHa (humanized antibody heavy chain variable region a version)>
(SEQ ID NO: 12)
EVQLVESGGGLVKPGGYLRLSCAASGFTFSSYAMSWVRQAPGKGLDWVAT

ISSGGSYTYYPDSVKGRFTISRDNAKNSLYLQMNSLTDDDTAVYFCARHN

YRYDEYYYAMDYWGQGTLVTVSS

<X70463>
(SEQ ID NO: 129)
DIQMTQSPSSLSASVGDRVTITCRASQSIGSFLHWYQQKPGKGPKLLISA

ASSLQSGVPSRFSGSGSGTDFTLTISSLQPEDFATYYCQQSFSTLYTFGQ

GTKLEIK

FR1 of X70463
(SEQ ID NO: 130)
DIQMTQSPSSLSASVGDRVTITC

FR2 of X70463
(SEQ ID NO: 131)
WYQQKPGKGPKLLIS

FR3 of X70463
(SEQ ID NO: 132)
GVPSRFSGSGSGTDFTLTISSLQPEDFATYYC

-continued

FR4 of X70463

FGQGTKLEIK                                    (SEQ ID NO: 133)

<FB54-rKa (humanized antibody light chain
variable region a version)>
                                              (SEQ ID NO: 9)
DIQMTQSPSSLSASVGDRVTITCITSTDIDDEMNWYQQKPGKGPKLLISE

GNTLRPGVPSRFSGSGSGTDFTLTISSLQPEDFATYYCLQSDNLPYTFGQ

GTKLEIK

<FB54-rKb (humanized antibody light chain
variable region b version)>
                                              (SEQ ID NO: 10)
DTQVTQSPSSLSASVGDRVTITCITSTDIDDEMNWYQQKPGKGPKLLISE

GNTLRPGVPSRFSSSGSGTDFTLTISSLQPEDFATYYCLQSDNLPYTFGQ

GTKLEIK

<FB54-rKc (humanized antibody light chain
variable region c version)>
                                              (SEQ ID NO: 11)
ETTVTQSPSSLSASVGDRVTIRCITSTDIDDEMNWYQQKPGKGPKLLISE

GNTLRPGVPSRFSSSGYGTDFTLTISSLQPEDFATYYCLQSDNLPYTFGQ

GTKLEIK

The heavy chain and light chain variable region genes of the humanized antibody were prepared by oligo DNA synthesis. On this occasion, the secretion signal sequences were converted into the sequences recommended by Lonza, and restriction enzyme recognition sequences were added to the ends of the chains (HindIII and BamHI recognition sequences were added for the heavy chain, while HindIII and BsiWI recognition sequences were added for the light chain). After cleavage with the restriction enzymes, the cleaved genes were transduced, respectively, into pEE6.4 vector (Lonza) into which human IgG1 constant region had been cloned, and into pEE14.4 vector (Lonza) into which human κ chain constant region had been cloned.

The constructed heavy chain and light chain expression vectors were cotransfected, in combinations of FB54-rHa and FB54-rKa, FB54-rHa and FB54-rKb and FB54-rHa and FB54-rKc, into 293T cells by the customary method using Lipofectamine 2000 (Invitrogen). As controls, the expression vectors (FB54-chH and FB54-chK) for the chimeric antibody prepared above were also transfected.

At 48 hours after gene transfection, the culture supernatants were recovered, and their IgG concentrations were calculated from a calibration curve for commercially available purified human IgG (Cappel) by Sandwich ELISA using goat anti-human IgG antibody, Fcγ fragment-specific (Stratech Scientific) and goat anti-human kappa light chain peroxidase conjugate (Sigma).

Figure 9:
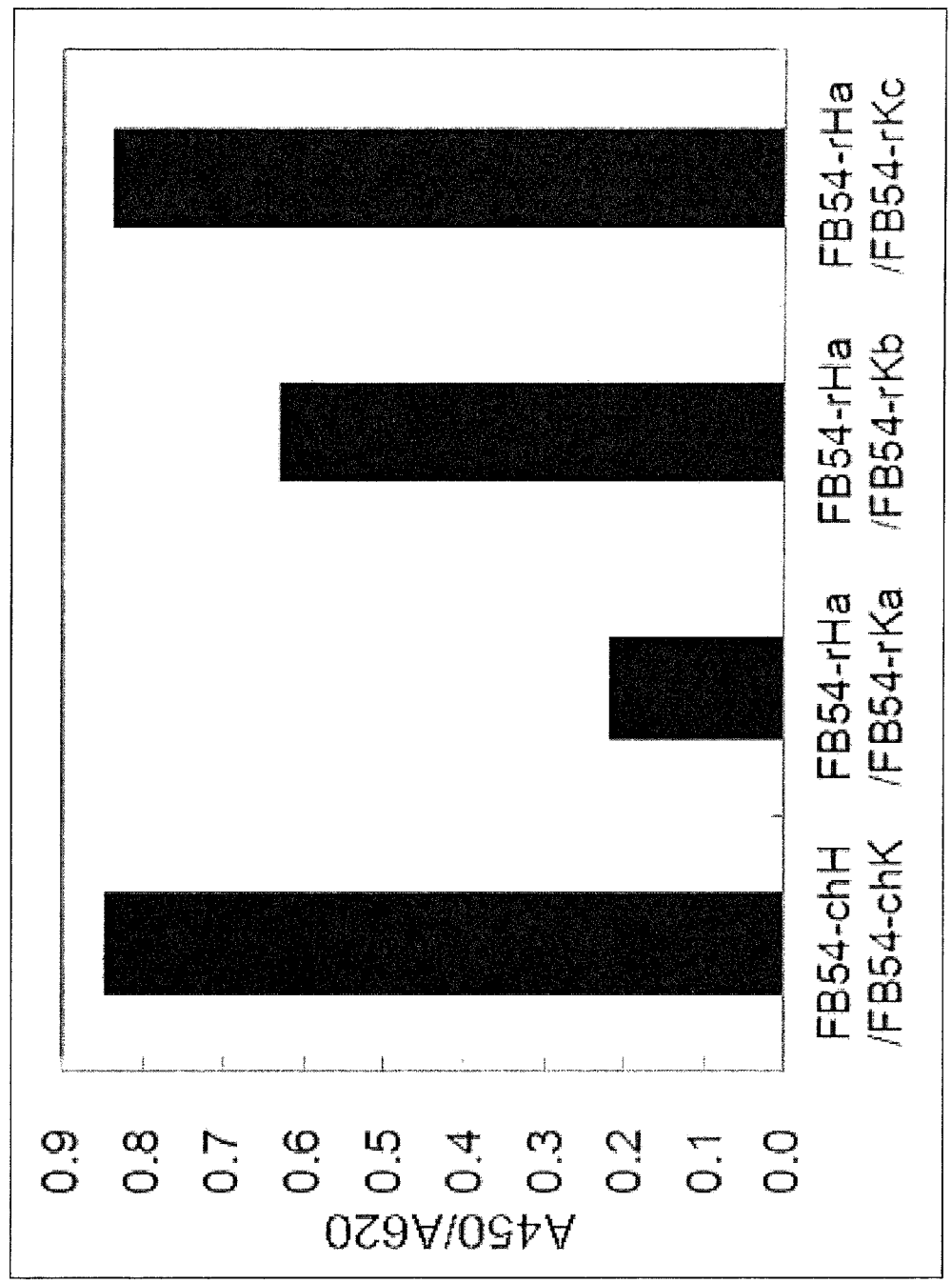
FIG. 9 is a graph showing the results of analyses by ELISA of the reactivities of a chimerized antibody for FB54 (an antibody having FB54-chH as the heavy chain variable region and FB54-chK as the light chain variable region) and humanized antibodies for FB54 (an antibody having FB54-rHa as the heavy chain variable region and FB54-rKa as the light chain variable region, an antibody having FB54-rHa as the heavy chain variable region and FB54-rKb as the light chain variable region, and an antibody having FB54-rHa as the heavy chain variable region and FB54-rKc as the light chain variable region) with recombinant human midkine.

Using these culture supernatants, reactivities with human MK were confirmed by enzyme-linked immunosorbent assay (ELISA). The assays were performed in the same manner as described above. The above culture supernatant was adjusted to a human IgG concentration of 10 µg/mL, and used as a primary antibody. HRP-labeled goat anti-human IgG (MBL: 206) was used as a secondary antibody. As a result, the chimeric antibody (FB54-chH/FB54-chK) and the humanized antibody (FB54-rHa/FB54-rKc) were confirmed to have comparable activity. Thus, success was achieved in designing the humanized FB54 antibodies (FIG. 9). Hereinbelow, the humanized antibody (FB54-rHa/FB54-rKc) will also be described as hFB54.

(Example 20) Evaluation of Reactivity of FB54 Humanized Antibody

Next, the expression vectors for FB54-rHa and FB54-rKc were joined together based on Lonza's protocol, and the joined product was transfected into CHOK1SV cells. A CHOK1SV monoclonal cell line highly expressing hFB54 was established, and an antibody was purified from its culture supernatant with the use of Protein A.

Figure 10:
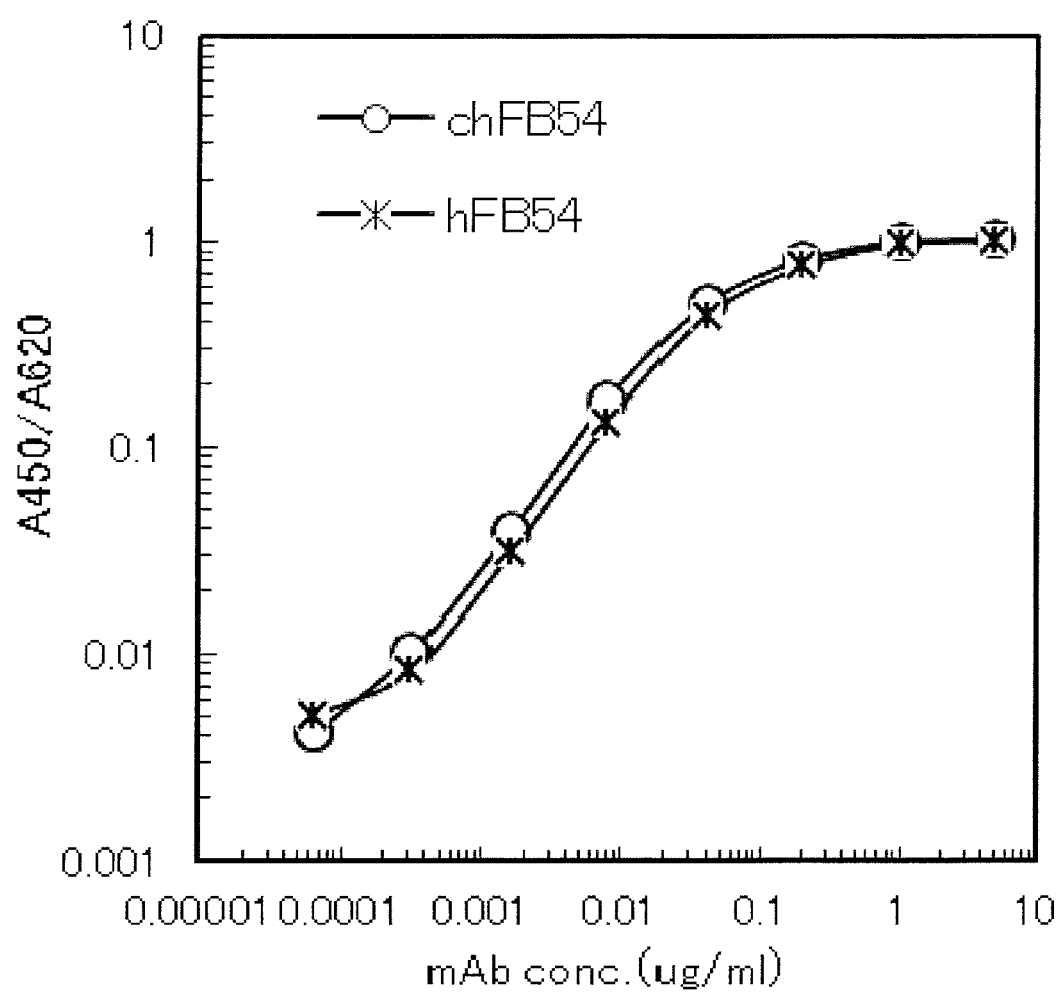
FIG. 10 is a graph showing the results of analyses by ELISA of the reactivities of a purified chimerized FB54 antibody (chFB54) and a purified humanized FB54 antibody (hFB54) with recombinant human midkine.

The reactivity of the resulting humanized antibody with human MK was confirmed by enzyme-linked immunosorbent assay (ELISA). The assay was performed in the same manner as described above. The hFB54 or chFB54 antibody as a control, at a maximum concentration of 5 µg/mL, was serially diluted with PBS, and used as a primary antibody. HRP-labeled goat anti-human IgG (MBL: 206) was used as a secondary antibody. As a result, hFB54 showed binding activity comparable to that of chFB54 (FIG. 10).

(Example 21) Evaluation of Antitumor Activity Using Mouse Xenograft

The antitumor activity of hFB54 was evaluated using a mouse xenograft. The human neuroblastoma cell line TNB1 (Riken BRC: RCB0481) was exfoliated with a solution of collagenase Type I (GIBCO: 17100-017) added in an amount of 2 mg/mL to Cell Dissociation Buffer enzyme free PBS-based (Invitrogen: 13151-014). After washing, the system was suspended in RPMI1640 medium (GIBCO) to a cell count of $5 \times 10^7$ cells/mL. An equal amount of Matrigel (BD: 354230) was added, and the mixture was suspended. Then, the suspension was subcutaneously transplanted to the right ventral part of 6-week-old female nude mice (Japan SLC: BALB/cSlc-nu/nu) in an amount of 200 µL each. From the same day onwards, 300 µL of a solution of the antibody diluted with 0.05% Tween 20-PBS to a concentration of 1 mg/mL, or 300 µL of 0.05% Tween 20-PBS, was intraperitoneally administered (8 mice/group). The antibody solution or the control was administered a total of 7 times, i.e., on the day of transplantation and twice weekly from Day 8. The diameter of a tumor was measured with a vernier caliper, beginning at a time when the tumor was observed. The tumor volume was calculated from the following equation:

Tumor volume (mm$^3$)=major diameter×minor diameter$^2$×0.5

The results are shown in FIG. 11. The tumor volumes in the hFB54-administered group were 54% at 29 days, 51% at 33 days, 50% at 36 days, and 54% at 41 days, compared with the corresponding tumor volumes in the control group. As these findings demonstrate, the anti-MK antibody hFB54 inhibited enlargement of the tumor significantly (P<0.05). In regard to the survival rate, all the animals were dead at about 90 days in the control group. In the hFB54 treatment group, by contrast, as many as 30% of the animals were alive even after 100 days, thus confirming the life-prolonging effect of the antibody. Hence, it has become clear that the anti-MK antibody hFB54 has an antitumor effect in initial cancer models.

(Example 22) FB54 In Vitro Affinity Maturation (Affinity Improvement)

(1) Transformation of IgG Antibodies into Fab Antibodies
With IgG antibody expression vectors for hFB54 and mFB54 as templates, the variable regions of the heavy chain and the light chain were amplified by PCR. The amplification products were cloned into Fab type antibody expression phagemid vectors. The reactivities of the Fab antibodies with MK were confirmed by enzyme-linked immunosorbent assay (ELISA).

(2) Preparation of Fab Antibodies Having Random Mutations Introduced into Antibody Variable Regions (Mutation-Introduced Library)

Mutations were introduced into the variable regions of the heavy chain and the light chain by error-prone PCR, and these mutated regions were cloned into Fab type antibody expression phagemid vectors in the same manner as above. As a result, a mutation-introduced Fab antibody phage library having various mutations introduced only into the antibody variable regions was prepared.

(3) Enrichment (Panning) of Clones with Improved Affinity (i) The antigen (MKver10 for hFB54, mMK for mFB54) was immobilized to ImmunoTube (nunc) tubes.

(ii) The mutation-introduced Fab antibody phage library was added, and bound to the antigen.

(iii) After a washing operation, the antibody phages bound to the antigen were recovered, and transferred to $E.\ coli$ for infection (50 ml culture solution, shake culture for 1 hr at 37° C.).

(iv) $E.\ coli$ holding phagemids was selected using a medication. (A solution from (iii) was added to 600 ml of a culture solution containing 100 μg/ml of ampicillin, and the mixture was shake cultured for 16 hours at 30° C.).

(v) A helper phage was allowed to infect, producing antibody phages.

(vi) The antibody phages were separated and concentrated.

(vii) Using the separated and concentrated antibody phage library, the steps (i) to (vi) were repeated a total of 3 times. The conditions for the hFB54 panning and the mFB54 panning are shown in Tables 1 and 2, respectively.

TABLE 1

|  | Antigen (MKver10) | Number of antibody phages | Amount of reaction liquor | Reaction time | Washing |
|---|---|---|---|---|---|
| 1st | 2.0 [nmole] | $3 \times 10^{13}$ | 4 [ml] | 5 [days] | 3 times → 2 [days] → 3 times |
| 2nd | 0.2 [nmole] | $3 \times 10^{13}$ | 4 [ml] | 5 [days] | 3 times → 7 [days] → 3 times |
| 3rd | 0.2 [nmole] | $3 \times 10^{13}$ | 4 [ml] | 5 [days] | 3 times → 7 [days] → 3 times |

TABLE 2

|  | Antigen (mMK) | Number of antibody phages | Amount of reaction liquor | Reaction time | Washing |
|---|---|---|---|---|---|
| 1st | 2.0 [nmole] | $3 \times 10^{13}$ | 4 [ml] | 6 [days] | 3 times |
| 2nd | 0.2 [nmole] | $3 \times 10^{13}$ | 4 [ml] | 6 [days] | 3 times → 6 [days] → 3 times |
| 3rd | 0.2 [nmole] | $3 \times 10^{13}$ | 4 [ml] | 6 [days] | 3 times → 7 [days] → 3 times |

(4) Evaluation of Affinity of Affinity-Improved Clones (ELISA Using $E.\ coli$ Culture Supernatants)

From the libraries (hFB54: $3.75 \times 10^7$ clones, mFB54: $1.75 \times 10^7$ clones) after panning repeated 3 times, 94 clones of Fab antibody phage-infected $E.\ coli$ were isolated, respectively. The reactivities of the Fab antibodies, secreted by these $E.\ coli$ clones into the culture broth, with MK were confirmed by enzyme-linked immunosorbent assay (ELISA).

For the assays, recombinant human MK (MKver10) or mouse MK (mMK) was dispensed, in an amount of 5 μg/mL or 100 μL/well, into a 96-well ELISA plate (nunc), and the system was allowed to stand overnight at 4° C. for adsorption before the system was used. After the resulting solution was removed, 1% BSA-5% sucrose-0.05% NaN3-PBS was added in an amount of 200 μL/well, and the system was allowed to stand overnight at 4° C. to block the remaining active groups. After the resulting solution was removed, the $E.\ coli$ culture supernatant was dispensed in an amount of 100 μL/well as a primary antibody into the plate, and system was allowed to stand for 2 hours at 37° C. After the plate was washed with PBS, a 1:2000 diluted rabbit anti-cp3 antibody (MBL) as a secondary antibody was added in an amount of 100 μL/well, and the plate was allowed to stand for 1 hour at 37° C. After the plate was washed with PBS, a 1:2500 diluted HRP-labeled goat anti-rabbit antibody (MBL: 458) as a tertiary antibody was added in an amount of 100 μL/well, and the plate was allowed to stand for 1 hour at 37° C. After the plate was washed with PBS, an OPD development solution was added to develop a color, and the absorbance at 492 nm was measured with a plate reader.

As a result, stronger reactivity than that of the original Fab-converted antibody was confirmed in a plurality of the clones. From the clones derived from hFB54, 9 clones with high absorbances (hFB54-matu014, 020, 024, 034, 039, 054, 062, 072, 086) were selected. Similarly, 4 clones with high absorbances (mFB54-matu002, 024, 025, 089) were selected from the mFB54-derived clones (FIGS. 12 to 15).

(5) Affinity Evaluation of Affinity-Improved Clones (ELISA Using Purified Fab Antibodies)

The Fab antibodies of the total 13 clones selected in the preceding step (9 clones derived from hFB54, 4 clones derived from mFB54) and the original antibodies (hFB54, mFB54) were purified. Then, the reactivities of these Fab antibodies with MK were evaluated by enzyme-linked immunosorbent assay (ELISA). The assays were performed in the same manner as described above. For a solid phase of the antigen, the antigen was adjusted to 2 μg/mL and used. The Fab antibody, at a maximum concentration of 5 μg/mL, was serially diluted with PBS, and used.

Figure 16:
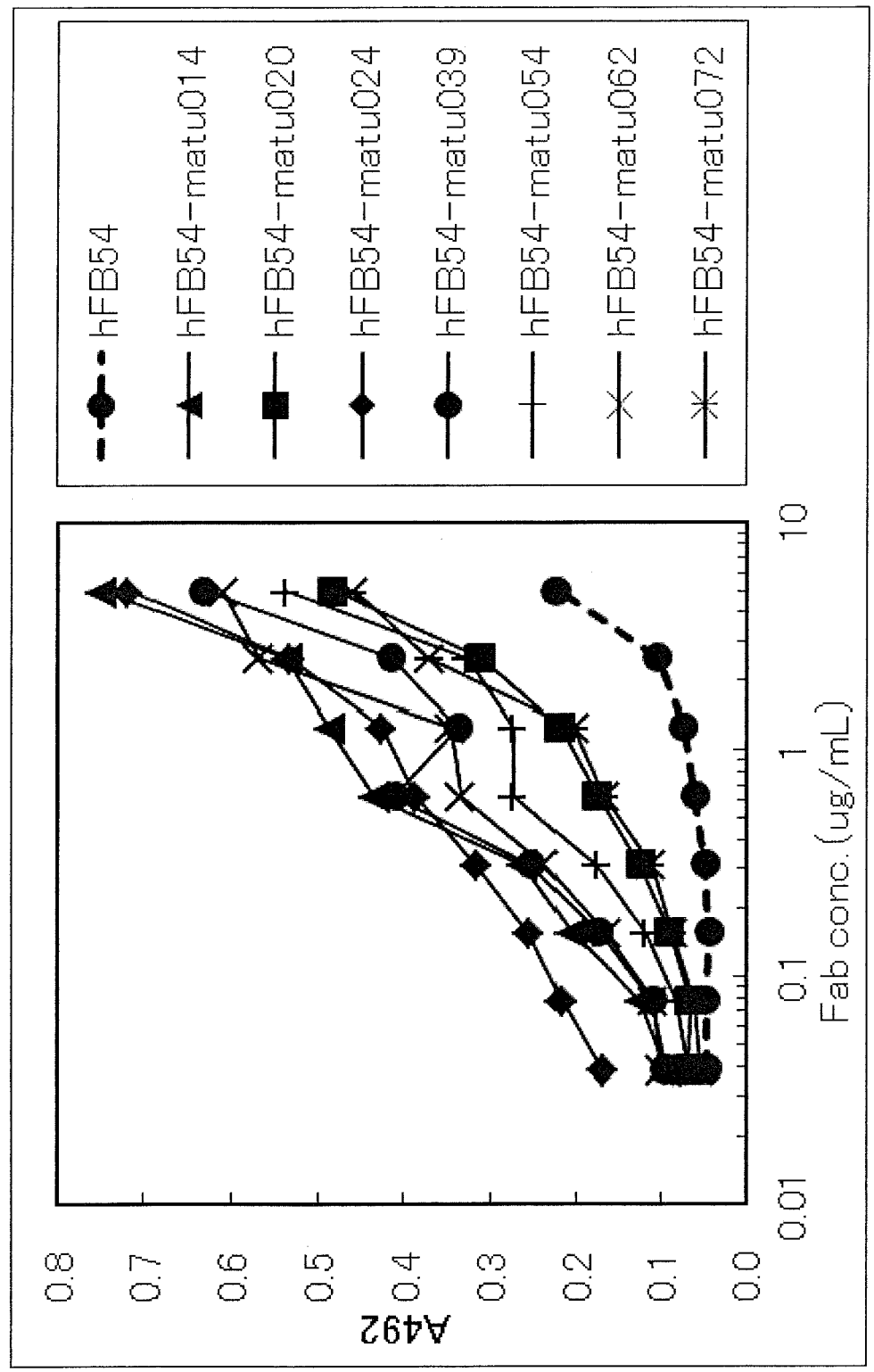
FIG. 16 is a graph showing the results of analyses by ELISA of the reactivities of hFB54 and its affinity-improved antibodies (hFB54-matu014, hFB54-matu020, hFB54-matu024, hFB54-matu039, hFB54-matu054, hFB54-matu062, and hFB54-matu072) with recombinant human midkine (MKver10).
Figure 17:
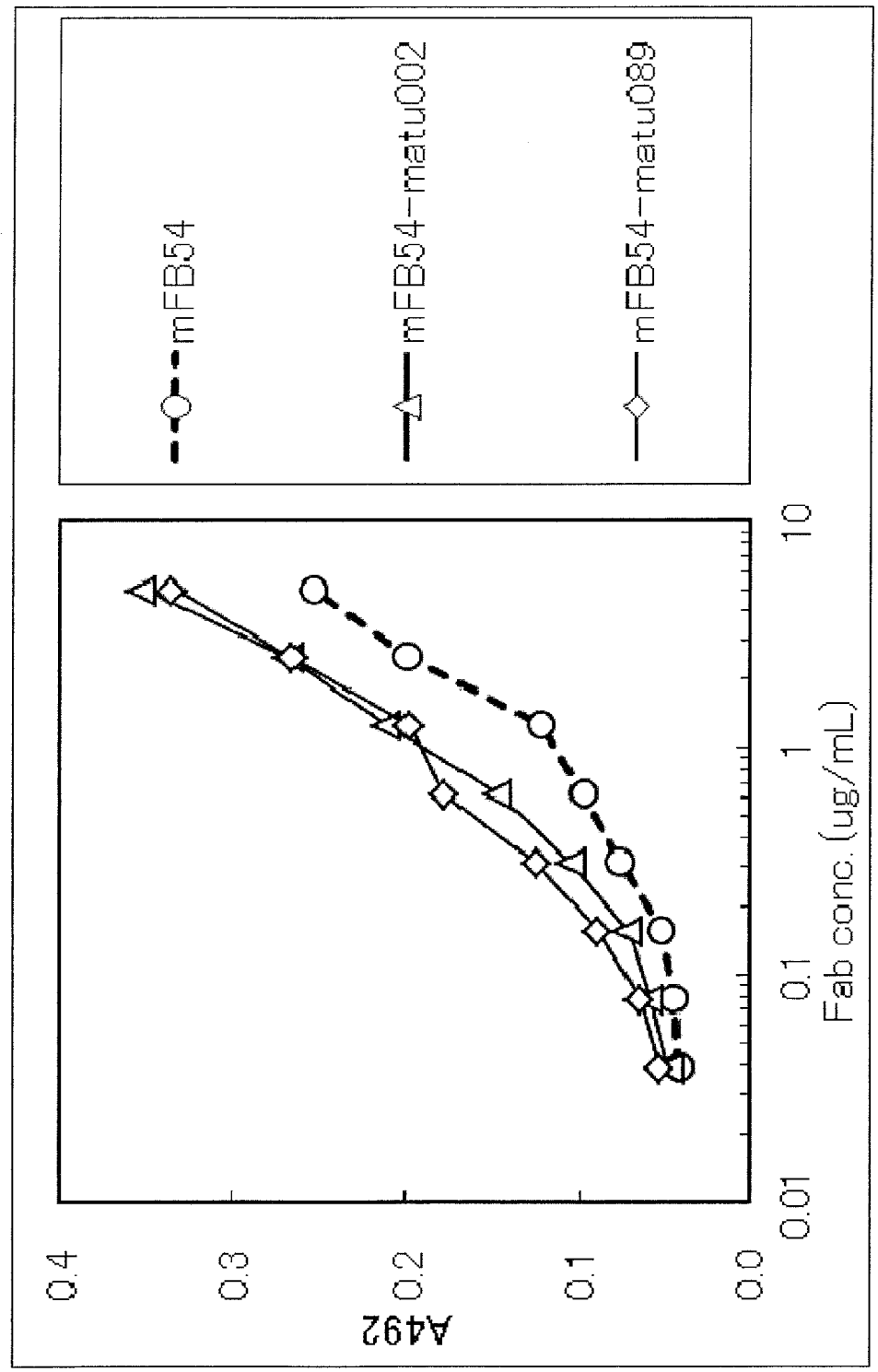
FIG. 17 is a graph showing the results of analyses by ELISA of the reactivities of mFB54 and its affinity-improved antibodies (mFB54-matu002, mFB54-matu089) with mouse midkine (mMK).

As a result, of the hFB54-derived nine clones, 7 clones were confirmed to be improved in reactivity with MKver10 (FIG. 16). In connection with the mFB54-derived four clones, 2 clones were confirmed to be improved in reactivity with mMK (FIG. 17).

The above findings showed that success was achieved in obtaining 7 clones of the Fab antibody with improved reactivity with human MK based on the Fab-converted antibody of humanized FB54, and 2 clones of the Fab antibody with improved reactivity with mouse MK based on the Fab-converted antibody of mouse FB54.

(6) Sequence Analysis of Affinity-Improved Clones

The sequences of the variable regions of the antibody heavy chain and light chain of the total 9 clones selected in the preceding item were analyzed using an autosequencer. The results are shown in FIG. 18 and below. In FIG. 18, the same amino acid residues as those in the original antibody were indicated by "-", whereas different residues were indicated by the substituting amino acids. The surrounding lines represent the CDR regions.

As clear from the results shown in FIG. 18, confirmation of the sequences of the CDRs in the 9 clones showed that in all the clones, the 4-position amino acid of the CDR1 of the light chain variable region was isoleucine. It was suggested, therefore, that the substitution of the amino acid at this site by isoleucine was important for the improvement of affinity and so on.

```
<matu002 heavy chain variable region>
                                               (SEQ ID NO: 20)
EVMLVESGGGLVKPGGSLKLSCAASGFTFSSYAMSWVRQTPEKRLEWVAT

ISSGGSYTYYPDSVKGRFTISRDNAKNTLYLQMSSLRSEDTAMYFCARHN

YRYDEYYYAMDYWGQGTSVTVSS

CDR1 of matu002 heavy chain variable region
                                               (SEQ ID NO: 16)
SYAMS CDR2 of matu002 heavy chain variable region
                                               (SEQ ID NO: 17)
TISSGGSYTYYPDSVKG CDR3 of matu002 heavy chain variable region
                                               (SEQ ID NO: 18)
HNYRYDEYYYAMDY <matu002 light chain variable region>
                                               (SEQ ID NO: 19)
ETTVTQSPTSLSMAIGEKVTIRCTTSIDIDDEMNWYQQMPGEPPKLLISE

GNTLRPGVPSRFSSSGYGTDFVFTIENMLSEDVADYYCLQSDNLPYTFGG

GTKLEIK

CDR1 of matu002 light chain variable region
                                               (SEQ ID NO: 13)
TTSIDIDDEMN CDR2 of matu002 light chain variable region
                                               (SEQ ID NO: 14)
EGNTLRP CDR3 of matu002 light chain variable region
                                               (SEQ ID NO: 15)
LQSDNLPYT <matu089 heavy chain variable region>
                                               (SEQ ID NO: 28)
EVMLVESGGGLVEPGGSLKLSCTVSGFTFSSYAMSWVRQTPEKRLEWVAT

ISSGGSYTYYPDSVKGRFTISRDNAKNTLYLQMSSLRSEDTAMYFCARHN

YRYDEYYYAMDYWGHGTSVTVSS

CDR1 of matu089 heavy chain variable region
                                               (SEQ ID NO: 24)
SYAMS CDR2 of matu089 heavy chain variable region
                                               (SEQ ID NO: 25)
TISSGGSYTYYPDSVKG CDR3 of matu089 heavy chain variable region
                                               (SEQ ID NO: 26)
HNYRYDEYYYAMDY <matu089 light chain variable region>
                                               (SEQ ID NO: 27)
ETTVTQSPTSLSMAIGEKVTIRCITSIDIDDEMNWYQQKPGEPPKLLISE

GNTLRPGVPSRFSSSGYGTDFVFTIENVLSEDVADYYCLQSDNLPYTFGG

GTKLEIK
```

-continued
```
CDR1 of matu089 light chain variable region
                                               (SEQ ID NO: 21)
ITSIDIDDEMN CDR2 of matu089 light chain variable region
                                               (SEQ ID NO: 22)
EGNTLRP CDR3 of matu089 light chain variable region
                                               (SEQ ID NO: 23)
LQSDNLPYT <matu014 heavy chain variable region>
                                               (SEQ ID NO: 36)
EVQLVESGGGLVKPGGYLRLSCAASGFTFSSYAMSWVRQTPGKGLDWVAT

ISSGGSYTYYPDSVKGRFTISRDNVKNSLYLQMNSLTDDDTAVYFCARHN

YRYDEYYYAMDYWGQGTLVTVSS

CDR1 of matu014 heavy chain variable region
                                               (SEQ ID NO: 32)
SYAMS CDR2 of matu014 heavy chain variable region
                                               (SSEQ ID NO: 33)
TISSGGSYTYYPDSVKG CDR3 of matu014 heavy chain variable region
                                               (SEQ ID NO: 34)
HNYRYDEYYYAMDY <matu014 light chain variable region>
                                               (SSEQ ID NO: 35)
ETTVTQSPSSLSASVGDRVTIRCITNIDIDDEMNWYQQKPGKGPKLLISE

GNTLRPGVPSRFSSSGYGTDFTLTISSLQPEDFATYYCLQSDNLPYTFGR

GTKLEIK

CDR1 of matu014 light chain variable region
                                               (SEQ ID NO: 29)
ITNIDIDDEMN CDR2 of matu014 light chain variable region
                                               (SEQ ID NO: 30)
EGNTLRP CDR3 of matu014 light chain variable region
                                               (SEQ ID NO: 31)
LQSDNLPYT <matu020 heavy chain variable region>
                                               (SEQ ID NO: 44)
EVQLVESGGGLVKPGGYQRLSCAASGFTFSSYAMSWVRQAPGKGLDWVAT

ISSGGSYTYYPDSVKGRFTISRDNAKNSLYLQMNNLTDDDTAVYFCARHN

YRYDEYYHAMDYWGQGTLVTVSS

CDR1 of matu020 heavy chain variable region
                                               (SEQ ID NO: 40)
SYAMS CDR2 of matu020 heavy chain variable region
                                               (SEQ ID NO: 41)
TISSGGSYTYYPDSVKG CDR3 of matu020 heavy chain variable region
                                               (SEQ ID NO: 42)
HNYRYDEYYHAMDY <matu020 light chain variable region>
                                               (SEQ ID NO: 43)
ETTVTQSPSSLSASVGDRVTIRCITSIDIDDEMNWYQQKPGKGPKLLISE

GNTLRPGVPSRFSSSGYGTDFTLTISSLQPEDFATYYCLQSDNLPYTFGQ

GTKLEIK
```

CDR1 of matu020 light chain variable region
(SEQ ID NO: 37)
ITSIDIDDEMN

CDR2 of matu020 light chain variable region
(SEQ ID NO: 38)
EGNTLRP

CDR3 of matu020 light chain variable region
(SEQ ID NO: 39)
LQSDNLPYT

<matu024 heavy chain variable region>
(SEQ ID NO: 52)
EVQLVESGGGLVKPGGYLRLSCAASGFTFSSYAMSWVRQAPGKGLDWVAT
ISSGGSYTYYPDSVKGRFTISRDNAKNSLYLQMNSLTDDDTAVYFCARHN
YRYGEYYYAMDYWGQGTLVTVSS CDR1 of matu024 heavy chain variable region
(SEQ ID NO: 48)
SYAMS CDR2 of matu024 heavy chain variable region
(SEQ ID NO: 49)
TISSGGSYTYYPDSVKG CDR3 of matu024 heavy chain variable region
(SEQ ID NO: 50)
HNYRYGEYYYAMDY <matu024 light chain variable region>
(SEQ ID NO: 51)
ETTVTQSPSSLSASVGDRVTIRCITSIDIDDEMNWYQQKSGKGPKLLISE
GNTLRPGVPSRFSSSGYGTDFTLTISSLQPEDFATYYCLQSDNLPYTFGQ
GTKLEIK CDR1 of matu024 light chain variable region
(SEQ ID NO: 45)
ITSIDIDDEMN CDR2 of matu024 light chain variable region
(SEQ ID NO: 46)
EGNTLRP CDR3 of matu024 light chain variable region
(SEQ ID NO: 47)
LQSDNLPYT <matu039 heavy chain variable region>
(SEQ ID NO: 60)
EVRLVESGGGLVKPGGYLRLSCAASGFTFSSYAMSWVRQAPGKGLDWVAT
ISSGGSYTYYPDSVKERFTISRDNAKNSLYLQMNSLTDDDTAVYFCARHN
YRYDEYYYGMDYWGQGTLVTVSS CDR1 of matu039 heavy chain variable region
(SEQ ID NO: 56)
SYAMS CDR2 of matu039 heavy chain variable region
(SEQ ID NO: 57)
TISSGGSYTYYPDSVKE CDR3 of matu039 heavy chain variable region
(SEQ ID NO: 58)
HNYRYDEYYYGMDY <matu039 light chain variable region>
(SEQ ID NO: 59)
ETTVTQSPSSLSASVGDRVTIRCKTSIDIDDEMNWYQQKPGKGPKLLISE
GNTLRPGVPSRFSSSGYGTDFTLTISSLQPEDFATYYCLQSDNLPYTFGQ
GTKLGIK CDR1 of matu039 light chain variable region
(SEQ ID NO: 53)
KTSIDIDDEMN CDR2 of matu039 light chain variable region
(SEQ ID NO: 54)
EGNTLRP CDR3 of matu039 light chain variable region
(SEQ ID NO: 55)
LQSDNLPYT <matu054 heavy chain variable region>
(SEQ ID NO: 68)
EVQLVESGGGLVKPGGYLRLSCAASGFTFSSYAMSWVRQAPGKGLDWVAT
ISSGGSYTYYPDSVKGRFTISRDNTKNTLYLQMNSLTDDDTAVYFCARHN
YRYDEYYYAMDYWGQGTLVTVSS CDR1 of matu054 heavy chain variable region
(SEQ ID NO: 64)
SYAMS CDR2 of matu054 heavy chain variable region
(SEQ ID NO: 65)
TISSGGSYTYYPDSVKG CDR3 of matu054 heavy chain variable region
(SEQ ID NO: 66)
HNYRYDEYYYAMDY <matu054 light chain variable region>
(SSEQ ID NO: 67)
ETTVTQSPSSLSASVGDRVTIRCITSIDIEDEMNWYQQKPGKGPKLLISE
GNTLRPGVPSRFSSSGYGTDFTLTISSLQPEDFATYYCLQSDNLPYTFGQ
GTKLEIK CDR1 of matu054 light chain variable region
(SEQ ID NO: 61)
ITSIDIEDEMN CDR2 of matu054 light chain variable region
(SEQ ID NO: 62)
EGNTLRP CDR3 of matu054 light chain variable region
(SEQ ID NO: 63)
LQSDNLPYT <matu062 heavy chain variable region>
(SEQ ID NO: 76)
EVQLVESGGGLVKPGGYLRLSCAASGFTFSSYAMSWVRQAPGKGLDWVAT
ISSGGSYTYYPDSVKGRFTISRDNAENTLYLQMNSLTNDDTAVYFCARHN
YRYDEYYYAMDYWGQGTLVTVSS CDR1 of matu062 heavy chain variable region
(SEQ ID NO: 72)
SYAMS CDR2 of matu062 heavy chain variable region
(SEQ ID NO: 73)
TISSGGSYTYYPDSVKG CDR3 of matu062 heavy chain variable region
(SEQ ID NO: 74)
HNYRYDEYYYAMDY <matu062 light chain variable region>
(SEQ ID NO: 75)
ETTVTQSPSSLSAFVGGRVAIRCITNIDIDDEMNWYQQKPGKGPKLLISE
GNTLRPGVPSRFSSSGYGTDFTLTISSLQPEDFATYYCMQSDNLPYTFGQ
GTKLEIK

```
CDR1 of matu062 light chain variable region
                                       (SEQ ID NO: 69)
ITNIDIDDEMN CDR2 of matu062 light chain variable region
                                       (SEQ ID NO: 70)
EGNTLRP CDR3 of matu062 light chain variable region
                                       (SEQ ID NO: 71)
MQSDNLPYT <matu072 heavy chain variable region>
                                       (SEQ ID NO: 84)
EVQLVESGGGLVKPGGYLRLSCAASGFTFSSYAMSWVRQAPGKGLDWVAT

ISSGGSYTYYPDNVKGRFTISRDNAKNSLYLQMNSLTDDDTAVYFCARHN

YRYDEYYHAMDYWGQGTLVTVSS

CDR1 of matu072 heavy chain variable region
                                       (SEQ ID NO: 80)
SYAMS CDR2 of matu072 heavy chain variable region
                                       (SEQ ID NO: 81)
TISSGGSYTYYPDNVKG CDR3 of matu072 heavy chain variable region
                                       (SEQ ID NO: 82)
HNYRYDEYYHAMDY <matu072 light chain variable region>
                                       (SEQ ID NO: 83)
ETTVTQSPSSLFASVGDKVTIRCITSIDIDDEMNWYQQKPGKGPKLLISE

GNTLRPGVPSRFSSSGYGTDFTLTISSLQPEDFATYYCLQSDNLPYTFGQ

GTKLEIK

CDR1 of matu072 light chain variable region
                                       (SEQ ID NO: 77)
ITSIDIDDEMN CDR2 of matu072 light chain variable region
                                       (SEQ ID NO: 78)
EGNTLRP CDR3 of matu072 light chain variable region
                                       (SEQ ID NO: 79)
LQSDNLPYT
```

(7) Conversion of Fab Antibodies into IgG Antibodies

The affinity-improved antibodies (Fab) of the aforementioned total 9 clones were converted into human IgG1 or mouse IgG1 in the following manner:

With Fab antibody expression vectors as templates, the heavy chain and light chain variable regions of the antibodies were amplified by PCR using primers to be described below. For both of the heavy chain and the light chain, the signal peptide portion and the variable region portion were separately amplified. Then, the amplification products were mixed, and coupled by PCR.

Like the preparation of the aforementioned chimeric antibodies and humanized antibodies, the coupled products were cleaved with restriction enzymes, and the cleaved products were introduced, respectively, into pEE6.4 vector (Lonza) into which the human IgG1 or mouse IgG1 constant region had been cloned, and pEE14.4 vector (Lonza) into which the human κ chain or mouse κ chain constant region had been cloned.

The expression vectors for the heavy chain and the light chain were bound and introduced into CHOK1SV cells based on Lonza's protocol. CHOK1SV monoclonal cell lines for increased production of the desired antibodies were established, and antibodies were purified from their culture supernatants by use of Protein A.

hFB54-matu014, 020, 024, 054, 062, 072 heavy chain signal peptide portion

```
VH_signal_F_HindIII:
5'-atataAAGCTTACCATGGAATGGAGCTGGG-3' (SEQ ID NO:

134; the underlined portion is HindIII recognition sequence)

hFB54VH_signal_R:
5'-CCAGCTGCACCTCAGAATGCACGCCTGTGGTC-3' (SEQ ID NO:

135)
``` hFB54-matu039 heavy chain signal peptide portion

```
VH_signal_F_HindIII:
5'-atataAAGCTTACCATGGAATGGAGCTGGG-3' (SEQ ID NO:

134; the underlined portion is HindIII recognition sequence)

hFB54VH039_signal_R:
5'-CCAGCcGCACCTCAGAATGCACGCCTGTGGTC-3' (SEQ ID

NO: 136)
``` mFB54-matu002, 089 heavy chain signal peptide portion

```
VH_signal_F_HindIII:
5'-atataAAGCTTACCATGGAATGGAGCTGGG-3' (SEQ ID NO:

134; the underlined portion is HindIII recognition sequence)

mFB54VH_signal_R: 5'-CCAGCATCACTTCAGAATGCACGCCTGTG

GTC-3' (SEQ ID NO: 137)
``` hFB54-matu014, 020, 024, 054, 062, 072 heavy chain variable region portion

```
hFB54VH_F: 5'-CGTGCATTCTGAGGTGCAGCTGGTGGAGTCG-3'

(SEQ ID NO: 138)

hFB54VH_R_XhoI: 5'-atataCTCGAGACGGTGACCAGGG-3'

(SEQ ID NO: 139; the underlined portion is XhoI recognition sequence)
``` hFB54-matu039 heavy chain variable region portion

```
hFB54VH039_F:
5'-CGTGCATTCTGAGGTGCGGCTGGTGGAGTCG-3' (SEQ ID NO:

140)

hFB54VH_R_XhoI:
5'-atataCTCGAGACGGTGACCAGGG-3' (SEQ ID NO: 139;

the underlined portion is XhoI recognition sequence)
``` mFB54-matu002, 089 heavy chain variable region portion mFB54VH_F:
5'-CGTGCATTCTGAAGTGATGCTGGTGGAGTCTGG-3' (SEQ ID NO: 141)

HC-reverse:
5'-atataCTCGAGACGGTGACTGAGG-3' (SEQ ID NO: 142; the underlined portion is XhoI recognition sequence)

Coupling between hFB54-matu014, 020, 024, 039, 054, 062, 072 heavy chain signal peptide portion and variable region portion VH_signal_F_HindIII:
5'-atataAAGCTTACCATGGAATGGAGCTGGG-3' (SEQ ID NO: 134; the underlined portion is HindIII recognition sequence)

hFB54VH_R_XhoI:
5'-atataCTCGAGACGGTGACCAGGG-3' (SEQ ID NO: 139; the underlined portion is XhoI recognition sequence)

Coupling between mFB54-matu002, 089 heavy chain signal peptide portion and variable region portion VH_signal_F_HindIII:
5'-atataAAGCTTACCATGGAATGGAGCTGGG-3' (SEQ ID NO: 134; the underlined portion is HindIII recognition sequence)

HC-reverse:
5'-atataCTCGAGACGGTGACTGAGG-3' (SEQ ID NO: 142; the underlined portion is XhoI recognition sequence)

hFB54-matu014, 020, 024, 039, 054, 062, 072, mFB54-matu002, 089 light chain signal peptide portion VK_signal_F_HindIII:
5'-atataAAGCTTACCATGTCTGTGCCTACCCAGG-3'
(SEQ ID NO: 134; the underlined portion is HindIII recognition sequence)

mhFB54VK_signal_R:
(SEQ ID NO: 143)
5'-CAGTTGTTTCACAGCGGGCGTCTGTCAGCC-3' hFB54-matu014, 020, 024, 054, 062, 072, mFB54-matu002, 089 light chain variable region portion mhFB54VK_F:
5'-ACGCCCGCTGTGAAACAACTGTGACCC-3' (SEQ ID NO: 144)

LC-reverse:
5'-atataCGTACGTTTGATTTCCAGCTTGGTGCC-3' (SEQ ID NO: 122; the underlined portion is BsiWI recognition sequence)

hFB54-matu039 light chain variable region portion mhFB54VKF:
5'-ACGCCCGCTGTGAAACAACTGTGACCC-3' (SEQ ID NO: 143)

hFB54VK039_R_BsiWI:
5'-atataCGTACGTTTGATCCCCAGCTTGGTTCC-3' (SEQ ID NO: 145; the underlined portion is BsiWI recognition sequence)

Coupling between hFB54-matu014, 020, 024, 054, 062, 072, mFB54-matu002, 089 light chain signal peptide portion and variable region portion VK_signal_F_HindIII:
5'-atataAAGCTTACCATGTCTGTGCCTACCCAGG-3' (SEQ ID NO: 134; the underlined portion is HindIII recognition sequence)

LC-reverse:
5'-atataCGTACGTTTGATTTCCAGCTTGGTGCC-3' (SEQ ID NO: 122; the underlined portion is BsiWI recognition sequence)

Coupling between hFB54-matu039 light chain signal peptide portion and variable region portion VK_signal_F_HindIII:
5'-atataAAGCTTACCATGTCTGTGCCTACCCAGG-3' (SEQ ID NO: 134; the underlined portion is HindIII recognition sequence)

hFB54VK039_R_BsiWI:
5'-atataCGTACGTTTGATCCCCAGCTTGGTTCC-3' (SEQ ID NO: 145; the underlined portion is BsiWI recognition sequence)

(Example 23) Affinity Evaluation of FB54 Affinity-Improved Antibodies

The reactivities of the obtained affinity-improved antibodies with MK were confirmed by enzyme-linked immunosorbent assay (ELISA). The assays were performed in the same manner as described above. The affinity-improved antibodies (hFB54-matu014, 020, 024, 039, 054, 062, 072, mFB54-matu002, 089) and the hFB54 or mouse FB54 antibody as a control, at a maximum concentration of 5 μg/mL, were each serially diluted with PBS, and used as a primary antibody. HRP-labeled goat anti-human IgG (MBL: 206) or HRP-labeled goat anti-mouse IgG (MBL: 330) was used as a secondary antibody.

Figure 19:
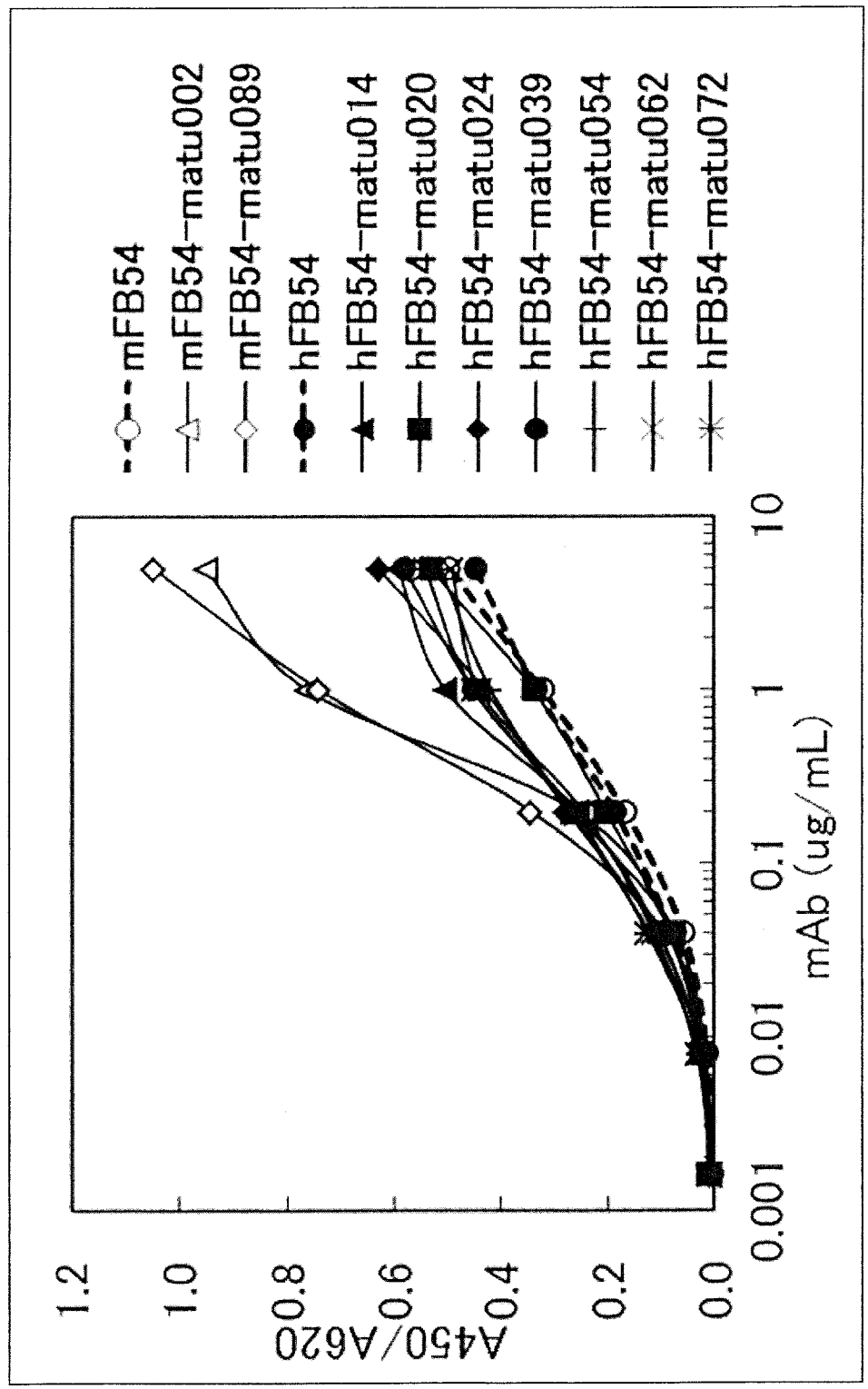
FIG. 19 is a graph showing the results of analyses by ELISA of the reactivities of mFB54, the affinity-improved antibodies of mFB54, hFB54, and the affinity-improved antibodies of hFB54 with recombinant human midkine (MKver10).
Figure 20:
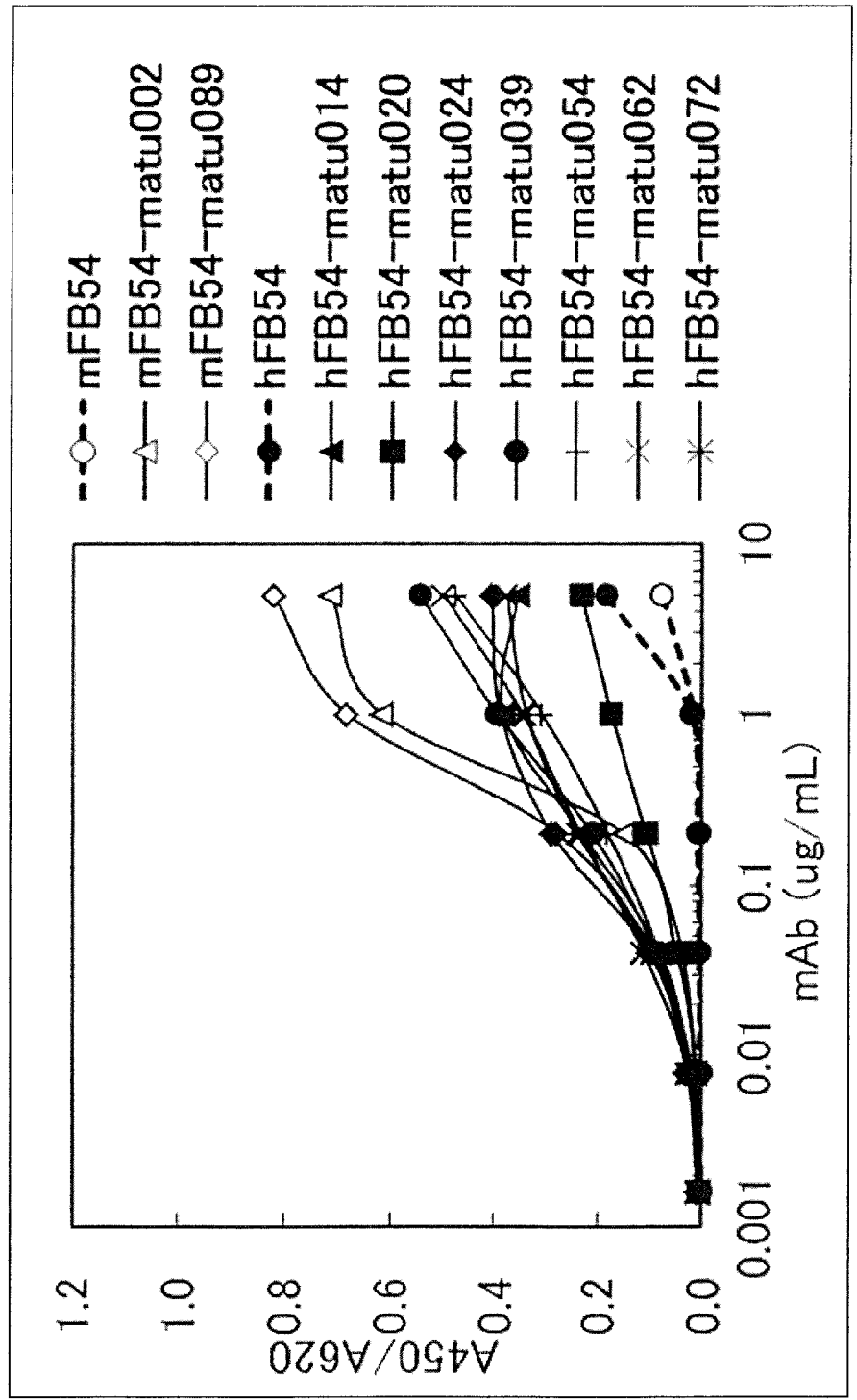
FIG. 20 is a graph showing the results of analyses by ELISA of the reactivities of mFB54, the affinity-improved antibodies of mFB54, hFB54, and the affinity-improved antibodies of hFB54 with mouse midkine (mMK).

As a result, all of the affinity-improved antibodies were confirmed to be improved in reactivities with both of human MK and mouse MK (FIGS. 19, 20).

(Example 24) AP-MK Binding Inhibition Assay (FB54 Affinity-Improved Antibodies)

The MK neutralizing activity of the obtained FB54-derived affinity-improved antibodies was evaluated by the same AP-MK binding inhibition assay as the assay described earlier. However, each antibody was added in an amount of 10 μg/mL. The results obtained are shown in FIG. 21.

As shown in FIG. 21, the activity of AP was lowered to 81.8% in the wells containing humanized FB54 (hFB54), as compared with the wells containing AP-MK alone. In the wells containing the affinity-improved antibodies of FB54, the activities of AP were lowered to 18.9%, 20.0%, 25.6%, 26.8%, 22.7%, 30.1%, 33.5%, 28.3% and 33.0%, respectively, in mFB54-002, mFB54-089, hFB54-014, hFB54-020, hFB54-024, hFB54-039, hFB54-054, hFB54-062, and hFB54-072. No decline in the AP activity was observed in the wells containing the control antibody. Based on these findings, the affinity-improved antibodies were confirmed to have even stronger neutralizing activity than the original antibodies.

INDUSTRIAL APPLICABILITY

The antibody of present invention has neutralizing activity against human midkine, and its tumor proliferation suppressing activity is also observed. Thus, the antibody of present invention can be used for the treatment of cancer. Because of its high reactivity with midkine, moreover, the antibody of present invention can also be applied as an agent for detection or purification of midkine.

SEQUENCE LISTING FREE TEXT

SEQ ID NO: 1
<223> CDR1 of light chain variable region (FB54)
SEQ ID NO: 2
<223> CDR2 of light chain variable region (FB54)
SEQ ID NO: 3
<223> CDR3 of light chain variable region (FB54)
SEQ ID NO: 4
<223> CDR1 of heavy chain variable region (FB54)
SEQ ID NO: 5
<223> CDR2 of heavy chain variable region (FB54)
SEQ ID NO: 6
<223> CDR3 of heavy chain variable region (FB54)
SEQ ID NO: 7
<223> Light chain variable region (FB54)
SEQ ID NO: 8
<223> Heavy chain variable region (FB54)
SEQ ID NO: 9
<223> Artificially humanized light chain variable region
<223> Light chain variable region (FB54-rKa)
SEQ ID NO: 10
<223> Artificially humanized light chain variable region
<223> Light chain variable region (FB54-rKb)
SEQ ID NO: 11
<223> Artificially humanized light chain variable region
<223> Light chain variable region (FB54-rKc)
SEQ ID NO: 12
<223> Artificially humanized heavy chain variable region
<223> Heavy chain variable region (FB54-rHa)
SEQ ID NO: 13
<223> CDR1 of artificially mutated light chain variable region
<223> CDR1 of light chain variable region (matu002)
SEQ ID NO: 14
<223> CDR2 of light chain variable region (matu002)
SEQ ID NO: 15
<223> CDR3 of light chain variable region (matu002)
SEQ ID NO: 16
<223> CDR1 of heavy chain variable region (matu002)
SEQ ID NO: 17
<223> CDR2 of heavy chain variable region (matu002)
SEQ ID NO: 18
<223> CDR3 of heavy chain variable region (matu002)
SEQ ID NO: 19
<223> Artificially mutated light chain variable region
<223> Light chain variable region (matu002)
SEQ ID NO: 20
<223> Heavy chain variable region (matu002)
SEQ ID NO: 21
<223> CDR1 of artificially mutated light chain variable region
<223> CDR1 of light chain variable region (matu089)
SEQ ID NO: 22
<223> CDR2 of light chain variable region (matu089)
SEQ ID NO: 23
<223> CDR3 of light chain variable region (matu089)
SEQ ID NO: 24
<223> CDR1 of heavy chain variable region (matu089)
SEQ ID NO: 25
<223> CDR2 of heavy chain variable region (matu089)
SEQ ID NO: 26
<223> CDR3 of heavy chain variable region (matu089)
SEQ ID NO: 27
<223> Artificially mutated light chain variable region
<223> Light chain variable region (matu089)
SEQ ID NO: 28
<223> Artificially mutated heavy chain variable region
<223> Heavy chain variable region (matu089)
SEQ ID NO: 29
<223> CDR1 of artificially mutated light chain variable region
<223> CDR1 of light chain variable region (matu014)
SEQ ID NO: 30
<223> CDR2 of light chain variable region (matu014)
SEQ ID NO: 31
<223> CDR3 of light chain variable region (matu014)
SEQ ID NO: 32
<223> CDR1 of heavy chain variable region (matu014)
SEQ ID NO: 33
<223> CDR2 of heavy chain variable region (matu014)
SEQ ID NO: 34
<223> CDR3 of heavy chain variable region (matu014)
SEQ ID NO: 35
<223> Artificially mutated light chain variable region
<223> Light chain variable region (matu014)
SEQ ID NO: 36
<223> Artificially mutated heavy chain variable region
<223> Heavy chain variable region (matu014)
SEQ ID NO: 37
<223> CDR1 of artificially mutated light chain variable region
<223> CDR1 of light chain variable region (matu020)
SEQ ID NO: 38
<223> CDR2 of light chain variable region (matu020)
SEQ ID NO: 39
<223> CDR3 of light chain variable region (matu020)
SEQ ID NO: 40
<223> CDR1 of heavy chain variable region (matu020)
SEQ ID NO: 41
<223> CDR2 of heavy chain variable region (matu020)

SEQ ID NO: 42
<223> CDR3 of artificially mutated heavy chain variable region
<223> CDR3 of heavy chain variable region (matu020)
SEQ ID NO: 43
<223> Artificially mutated light chain variable region
<223> Light chain variable region (matu020)
SEQ ID NO: 44
<223> Artificially mutated heavy chain variable region
<223> Heavy chain variable region (matu020)
SEQ ID NO: 45
<223> CDR1 of artificially mutated light chain variable region
<223> CDR1 of light chain variable region (matu024)
SEQ ID NO: 46
<223> CDR2 of light chain variable region (matu024)
SEQ ID NO: 47
<223> CDR3 of light chain variable region (matu024)
SEQ ID NO: 48
<223> CDR1 of heavy chain variable region (matu024)
SEQ ID NO: 49
<223> CDR2 of heavy chain variable region (matu024)
SEQ ID NO: 50
<223> CDR3 of artificially mutated heavy chain variable region
<223> CDR3 of heavy chain variable region (matu024)
SEQ ID NO: 51
<223> Artificially mutated light chain variable region
<223> Light chain variable region (matu024)
SEQ ID NO: 52
<223> Artificially mutated heavy chain variable region
<223> Heavy chain variable region (matu024)
SEQ ID NO: 53
<223> CDR1 of artificially mutated light chain variable region
<223> CDR1 of light chain variable region (matu039)
SEQ ID NO: 54
<223> CDR2 of light chain variable region (matu039)
SEQ ID NO: 55
<223> CDR3 of light chain variable region (matu039)
SEQ ID NO: 56
<223> CDR1 of heavy chain variable region (matu039)
SEQ ID NO: 57
<223> CDR2 of artificially mutated heavy chain variable region
<223> CDR2 of heavy chain variable region (matu039)
SEQ ID NO: 58
<223> CDR3 of artificially mutated heavy chain variable region
<223> CDR3 of heavy chain variable region (matu039)
SEQ ID NO: 59
<223> Artificially mutated light chain variable region
<223> Light chain variable region (matu039)
SEQ ID NO: 60
<223> Artificially mutated heavy chain variable region
<223> Heavy chain variable region (matu039)
SEQ ID NO: 61
<223> CDR1 of artificially mutated light chain variable region
<223> CDR1 of light chain variable region (matu054)
SEQ ID NO: 62
<223> CDR2 of light chain variable region (matu054)
SEQ ID NO: 63
<223> CDR3 of light chain variable region (matu054)
SEQ ID NO: 64
<223> CDR1 of heavy chain variable region (matu054)
SEQ ID NO: 65
<223> CDR2 of heavy chain variable region (matu054)
SEQ ID NO: 66
<223> CDR3 of heavy chain variable region (matu054)
SEQ ID NO: 67
<223> Artificially mutated light chain variable region
<223> Light chain variable region (matu054)
SEQ ID NO: 68
<223> Artificially mutated heavy chain variable region
<223> Heavy chain variable region (matu054)
SEQ ID NO: 69
<223> CDR1 of artificially mutated light chain variable region
<223> CDR1 of light chain variable region (matu062)
SEQ ID NO: 70
<223> CDR2 of light chain variable region (matu062)
SEQ ID NO: 71
<223> CDR3 of artificially mutated light chain variable region
<223> CDR3 of light chain variable region (matu062)
SEQ ID NO: 72
<223> CDR1 of heavy chain variable region (matu062)
SEQ ID NO: 73
<223> CDR2 of heavy chain variable region (matu062)
SEQ ID NO: 74
<223> CDR3 of heavy chain variable region (matu062)
SEQ ID NO: 75
<223> Artificially mutated light chain variable region
<223> Light chain variable region (matu062)
SEQ ID NO: 76
<223> Artificially mutated heavy chain variable region
<223> Heavy chain variable region (matu062)
SEQ ID NO: 77
<223> CDR1 of artificially mutated light chain variable region
<223> CDR1 of light chain variable region (matu072)
SEQ ID NO: 78
<223> CDR2 of light chain variable region (matu072)
SEQ ID NO: 79
<223> CDR3 of artificially mutated light chain variable region
<223> CDR3 of light chain variable region (matu072)
SEQ ID NO: 80
<223> CDR1 of heavy chain variable region (matu072)
SEQ ID NO: 81
<223> CDR2 of artificially mutated heavy chain variable region
<223> CDR2 of heavy chain variable region (matu072)
SEQ ID NO: 82
<223> CDR3 of artificially mutated heavy chain variable region
<223> CDR3 of heavy chain variable region (matu072)
SEQ ID NO: 83
<223> Artificially mutated light chain variable region
<223> Light chain variable region (matu072)
SEQ ID NO: 84
<223> Artificially mutated heavy chain variable region
<223> Heavy chain variable region (matu072)
SEQ ID NO: 85 to 123 and 134 to 145
<223> Artificially synthesized primer sequence
SEQ ID NO: 124
<223> Heavy chain variable region (AF471493)
SEQ ID NO: 125
<223> FR1 of heavy chain variable region (AF471493)
SEQ ID NO: 126
<223> FR2 of heavy chain variable region (AF471493)

SEQ ID NO: 127
<223> FR3 of heavy chain variable region (AF471493)
SEQ ID NO: 128
<223> FR4 of heavy chain variable region (AF471493)
SEQ ID NO: 129
<223> Light chain variable region (X70463)
SEQ ID NO: 130
<223> FR1 of light chain variable region (X70463)
SEQ ID NO: 131
<223> FR2 of light chain variable region (X70463)
SEQ ID NO: 132
<223> FR3 of light chain variable region (X70463)
SEQ ID NO: 133
<223> FR4 of light chain variable region (X70463)

The invention claimed is:

1. A monoclonal antibody comprising
    a light chain variable region including complementarity-determining regions comprising amino acid sequences defined by SEQ ID NOs: 21 to 23, and
    a heavy chain variable region including complementarity-determining regions comprising amino acid sequences defined by SEQ ID NOs: 24 to 26.

2. The monoclonal antibody according to claim 1, comprising
    a light chain variable region including the amino acid sequence defined by SEQ ID NO: 27, and
    a heavy chain variable region including the amino acid sequence defined by SEQ ID NO: 28.

3. A composition comprising the monoclonal antibody according to claim 1 as an active principle and a pharmaceutically acceptable carrier.

4. A method for treating a cancer in which the cancer cells have an increased expression of midkine, comprising administering to a human with said cancer a therapeutically effective amount of the monoclonal antibody according to claim 1, thereby suppressing proliferation of tumors.

5. The method according to claim 4, wherein the cancer is a neuroblastoma.

6. The method according to claim 4, wherein the cancer is selected from the group consisting of esophageal carcinoma, thyroid carcinoma, bladder cancer, stomach cancer, pancreatic cancer, liver cancer, pulmonary cancer, breast cancer, neuroblastoma, glioblastoma, uterine cancer, ovarian cancer, and Wilms tumor.

* * * * *